(12) United States Patent
Saus et al.

(10) Patent No.: US 10,544,083 B2
(45) Date of Patent: Jan. 28, 2020

(54) GPBP INHIBITION USING $Q_2$ PEPTIDOMIMETICS

(71) Applicant: FibroStatin, S.L., Valencia (ES)

(72) Inventors: Juan Saus, Valencia (ES); Santos Fustero, Valencia (ES); Juan F. Sanz-Cervera, Burjassot (ES); Enrique Pérez-Payá, Valencia (ES); Raül Blasco, Valencia (ES); Francisco Revert-Ros, Valencia (ES); Fernando Revert, Valencia (ES)

(73) Assignee: Universitat de València, Valencia (ES)

( * ) Notice: Subject to any disclaimer, the term of this patent is extended or adjusted under 35 U.S.C. 154(b) by 0 days.

(21) Appl. No.: 15/892,317

(22) Filed: Feb. 8, 2018

(65) Prior Publication Data

US 2018/0179139 A1    Jun. 28, 2018

Related U.S. Application Data

(60) Continuation of application No. 14/944,721, filed on Nov. 18, 2015, now abandoned, which is a continuation of application No. 14/063,709, filed on Oct. 25, 2013, now Pat. No. 9,199,936, which is a division of application No. 12/940,598, filed on Nov. 5, 2010, now Pat. No. 8,586,776.

(60) Provisional application No. 61/258,432, filed on Nov. 5, 2009.

(51) Int. Cl.

| C07C 59/52 | (2006.01) |
|---|---|
| C07C 45/68 | (2006.01) |
| C07C 47/565 | (2006.01) |
| C07C 59/56 | (2006.01) |
| C07C 59/64 | (2006.01) |
| C07C 59/70 | (2006.01) |
| C07C 69/732 | (2006.01) |
| C07C 69/734 | (2006.01) |
| C07C 69/738 | (2006.01) |
| C07C 309/65 | (2006.01) |
| C07D 213/26 | (2006.01) |
| C07D 213/34 | (2006.01) |
| C07D 213/48 | (2006.01) |
| C07D 213/55 | (2006.01) |
| C07D 213/58 | (2006.01) |
| C07C 67/313 | (2006.01) |

(52) U.S. Cl.
CPC ............ *C07C 59/52* (2013.01); *C07C 45/68* (2013.01); *C07C 47/565* (2013.01); *C07C 59/56* (2013.01); *C07C 59/64* (2013.01); *C07C 59/70* (2013.01); *C07C 67/313* (2013.01); *C07C 69/732* (2013.01); *C07C 69/734* (2013.01); *C07C 69/738* (2013.01); *C07C 309/65* (2013.01); *C07D 213/26* (2013.01); *C07D 213/34* (2013.01); *C07D 213/48* (2013.01); *C07D 213/55* (2013.01); *C07D 213/58* (2013.01)

(58) Field of Classification Search
None
See application file for complete search history.

(56) References Cited

U.S. PATENT DOCUMENTS

| 5,723,500 A | 3/1998 | Stringer et al. |
|---|---|---|
| 6,103,720 A | 8/2000 | Lubisch et al. |
| 7,326,768 B2 | 2/2008 | Saus et al. |

FOREIGN PATENT DOCUMENTS

| JP | 2006-525346 | 11/2006 |
|---|---|---|
| JP | 2006-342104 | 12/2006 |
| JP | 2008-507498 | 3/2008 |
| JP | 2008-526910 | 7/2008 |
| WO | 1998/004508 | 2/1998 |
| WO | 2000/50607 | 8/2000 |
| WO | 2002/061430 | 8/2002 |
| WO | 2002/089738 | 11/2002 |
| WO | 2004/071426 | 8/2004 |
| WO | 2009/008311 | 1/2009 |
| WO | 2009/043889 | 4/2009 |
| WO | 2009/052126 | 4/2009 |
| WO | 2009/081195 | 7/2009 |

OTHER PUBLICATIONS

Thiemann et al. (Journal of Chemical Research, 2004, 11,723).*

(Continued)

*Primary Examiner* — Sudhakar Katakam
*Assistant Examiner* — Jennifer C Sawyer
(74) *Attorney, Agent, or Firm* — McDonnell Boehnen Hulbert & Berghoff LLP

(57) ABSTRACT

Disclosed are compounds of formula:

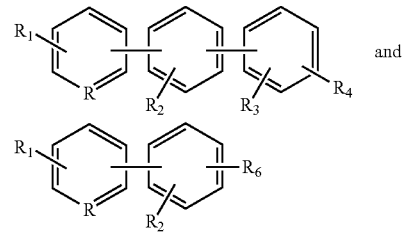

that inhibiting GPBP activity, making them useful as therapeutics in antibody-mediated disorders, drug-resistant cancer, inflammation, protein misfolding and ER stress-mediated disorders, and aberrant apoptosis.

19 Claims, No Drawings
Specification includes a Sequence Listing.

(56) References Cited

OTHER PUBLICATIONS

Ames, G. R. and Davey, W., Journal of the Chemical Society, 1958, p. 1794-1799.
Banerjee, S., Journal of Polymer Materials, 2007, vol. 24, No. 3, p. 247-254.
Bedford, R. B. and Limmert, M. E., Journal of Organic Chemistry, 2003, vol. 68, p. 8669-8682.
Cram, D. J. et al., Journal of the American Chemical Society, 1985, vol. 107, p. 3645-3657.
Freudenmann, R. et al., Synthetic Metals, 2000, vol. 111-112, p. 441-443.
Orner, et al., Toward Proteomimetics: Terphenyl Derivatives As Structural and Functional Mimics of Extended Regions of an α-Helix, Journal of the American Chemical Society, 2001, V123, p. 5382-5383.
Yin, et al., Terphenyl-Based BAK BH3 α-Helicalproteomimetics As Low-Molecular-Weight Antagonists OFBCL-XL, Journal of the American Chemical Society, 2005, V127, p. 10191-10196.
Yin, et al., Angewandte Chemie International Edition, 2005, V44, p. 2704-2707.
Hufnagel, F., Zeitschrift fuer Naturforschung, Teil A: Astrophysik, Physik and Physikalische 1143-1150 Chemie, 1970, p. 1143-1150.
Kissel, P. et al., European Journal of Organic Chemistry, 2009, p. 2953-2955.
Kissel, P. et al., Chemistry—A European Journal, 2009, vol. 15, p. 8955-8960.
Pizzirani, D. et al., Chem Med Chem, 2008, vol. 3, p. 345-355.
Rashidzadeh, B. et al., ARKIVOC (Gainesville, FL, United States), 2008, p. 167-172.
Ronan, D. et al., Organic Letters, 2004, vol. 6, No. 6, p. 885-887.
Schonberger, F. et al., Polymer, 2009, vol. 50, p. 2010-2024.
Fray, et al., (2001) "Dicovery of potent and selective succinyl-hyroxamate inhibitors of matrix metalloprotease-3 (Stromelysin-1)," Bioorganic & Medicinal Chemistry Letters, 11(4): 571-574.
Zheng, et al. (2006) Journal of Organic Chemistry 71: 5274-5281.
Dellagreca, et al. (2000) Journal of Chemical Ecology 26: 587-600.
Colacot, (2004) Organic Letters 6: 3731-3734.
Marx, et al. (1974) Journal of the American Chemical Society, 96:2121-2129.
Macchia, et al. (1998) European Journal of Medicinal Chemistry, 33: 911-919.
Alonso, et al. (1992) Tetrahedron, Elsevier Science Publishers, Amsterdam, NL, 48(13): 2709-2714.
Kuo, et al. (1997) Tetrahedron Letters, 38(19): 3343-3344.
Moore, et al. (1979) Journal of Organic Chemistry, 44: 925-930.
Ernst, et al. (2002) Angew. Chem. Int. Ed., 41: 278-281.
Léo, et al. (2002) Org. Lett., 4: 2711-2714.
Miyaura, et al. (1995) Chem. Rev., 95 : 2457-2483.
Ishiyama, et al. (1995) J. Org. Chem., 60: 7508-7510.
Konishi, et al. (1989) J. Bull. Chem. Soc. Jpn., 62: 591-593.
Tajik, et al. (2003) Synth. Commun., 33: 1319-1323.
ISR for PCT/EP2010/006757, dated Feb. 21, 2011.
Chen et al. (2005) Molecular Cancer Therapeutics, 4(6): 1019.

* cited by examiner

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Ser His Cys Ile Glu
1               5

<210> SEQ ID NO 2
<211> LENGTH: 14
<212> TYPE: PRT
<213> ORGANISM: Artificial Sequence
<220> FEATURE:
<223> OTHER INFORMATION: Synthetic

<400> SEQUENCE: 2

Leu Ala Thr Leu Ser His Cys Ile Glu Leu Met Val Lys Arg
1               5                   10
```

GPBP INHIBITION USING Q$_2$ PEPTIDOMIMETICS

CROSS REFERENCE TO RELATED APPLICATIONS

This application is a continuation of U.S. patent application Ser. No. 14/944,721, filed on Nov. 18, 2015, which is a continuation of U.S. patent application Ser. No. 14/063,709, filed Oct. 25, 2013, which is a divisional of U.S. patent application Ser. No. 12/940,598, filed Nov. 5, 2010, which claims the benefit of priority of U.S. Provisional Application No. 61/258,432, filed Nov. 5, 2009, all incorporated by reference herein in their entirety.

BACKGROUND OF THE INVENTION

The conformation of the non-collagenous (NC1) domain of the α3 chain of the basement membrane collagen IV [α3(IV)NC1] depends in part on phosphorylation. Goodpasture Antigen Binding Protein (GPBP) (WO 00/50607; WO 02/061430) is a non-conventional protein kinase that catalyzes the conformational isomerization of the α3(IV)NC1 domain during its supramolecular assembly, resulting in the production and stabilization of multiple α3(IV)NC1 conformers in basement membranes. Increased expression levels of GPBP have been associated with the production of aberrant non-tolerized α3(IV)NC1 conformers, which conduct the autoimmune response mediating Goodpasture ("GP") syndrome. In GP patients, autoantibodies against the α3(IV)NC1 domain ("Goodpasture antigen" or "GP antigen") cause a rapidly progressive glomerulonephritis and often lung hemorrhage, the two cardinal clinical manifestations of the GP syndrome. Furthermore, it has been proposed that GPBP regulates inflammation, apoptosis and protein folding, and that increased GPBP expression induces antibody-mediated glomerulonephritis (IgA nephropathy, systemic lupus erythematosus and Goodpastute autoimmune syndrome) and resistance of cancer cells to a number of chemotherapeutic agents including those (i.e. paclitaxel) inducing protein misfolding-mediated endoplasmic reticulum (ER) stress Thus, inhibitors of GPBP are useful for the treatment of antibody-mediated disorders, drug-resistant cancer, inflammation, protein misfolding and ER stress-mediated disorders, and aberrant apoptosis.

SUMMARY OF THE INVENTION

A first aspect of the invention provides compounds of formula (I):

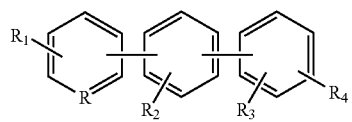

or a pharmaceutically acceptable salt thereof, wherein:
R is selected from N and CR$_5$;
  R$_5$ is selected from the group consisting of hydrogen, halogen, cyano, nitro, hydroxy, C$_1$-C$_6$ alkyl, C$_2$-C$_6$ alkenyl, C$_2$-C$_6$ alkynyl, halo(C$_1$-C$_6$ alkyl), C$_1$-C$_6$ alkoxy, halo(C$_1$-C$_6$ alkoxy), amino, (C$_1$-C$_6$ alkyl)amino, di(C$_1$-C$_6$ alkyl)amino, hydroxy(C$_1$-C$_6$ alkyl), (C$_1$-C$_6$ alkoxy)C$_1$-C$_6$ alkyl, amino(C$_1$-C$_6$ alkyl), sulfanyl(C$_1$-C$_6$ alkyl), (C$_1$-C$_6$ alkyl)sulfanyl(C$_1$-C$_6$ alkyl), —(CH$_2$)$_{1-5}$—C(O)(C$_1$-C$_6$ alkoxy), —(CH$_2$)$_{1-5}$—C(O)NH$_2$, (aryl)C$_2$-C$_6$ alkyl, and (heteroaryl)C$_1$-C$_6$ alkyl;
R$_1$ is hydrogen, halogen, hydroxy, C$_1$-C$_6$ alkyl, halo(C$_1$-C$_6$ alkyl), C$_1$-C$_6$ alkoxy, halo(C$_1$-C$_6$ alkoxy), hydroxy(C$_1$-C$_6$ alkyl), (C$_1$-C$_6$ alkoxy)C$_1$-C$_6$ alkyl, amino(C$_1$-C$_6$ alkyl), sulfanyl(C$_1$-C$_6$ alkyl), or (C$_1$-C$_6$ alkyl)sulfanyl(C$_1$-C$_6$ alkyl);
R$_2$ is C$_1$-C$_6$ alkyl, halo(C$_1$-C$_6$ alkyl), C$_1$-C$_6$ alkoxy, halo(C$_1$-C$_6$ alkoxy), hydroxy(C$_1$-C$_6$ alkyl), (C$_1$-C$_6$ alkoxy)C$_1$-C$_6$ alkyl, formyl(C$_0$-C$_6$ alkyl), amino(C$_1$-C$_6$ alkyl), sulfanyl(C$_1$-C$_6$ alkyl), (C$_1$-C$_6$ alkyl)sulfanyl(C$_1$-C$_6$ alkyl), —(CH$_2$)$_{1-5}$—C(O)OH, —(CH$_2$)$_{1-5}$—C(O)(C$_1$-C$_6$ alkoxy), —(CH$_2$)$_{1-5}$—C(O)NH$_2$, (aryl)C$_1$-C$_6$ alkyl, or (heteroaryl)C$_1$-C$_6$ alkyl;
R$_3$ is C$_1$-C$_6$ alkyl, halo(C$_1$-C$_6$ alkyl), C$_1$-C$_6$ alkoxy, halo(C$_1$-C$_6$ alkoxy), hydroxy(C$_1$-C$_6$ alkyl), (C$_1$-C$_6$ alkoxy)C$_1$-C$_6$ alkyl, formyl(C$_1$-C$_6$ alkyl), amino(C$_1$-C$_6$ alkyl), sulfanyl(C$_1$-C$_6$ alkyl), (C$_1$-C$_6$ alkyl)sulfanyl(C$_1$-C$_6$ alkyl), —(CH$_2$)$_{1-5}$—C(O)OH, —(CH$_2$)$_{1-5}$—C(O)(C$_1$-C$_6$ alkoxy), —(CH$_2$)$_{1-5}$—C(O)NH$_2$, —(CH$_2$)$_{1-5}$—C(O)NH(C$_1$-C$_6$ alkyl), —(CH$_2$)$_{1-5}$—C(O)N(C$_1$-C$_6$ alkyl)$_2$, —CH=CH—C(O)OH, —CH=CH—C(O)(C$_1$-C$_6$ alkoxy), (aryl)C$_1$-C$_6$ alkyl, or (heteroaryl)C$_1$-C$_6$ alkyl; and
R$_4$ is hydroxy, halogen, C$_1$-C$_6$ alkyl, C$_1$-C$_6$ alkoxy, halo(C$_1$-C$_6$ alkoxy), benzyloxy, —(CH$_2$)$_{1-5}$—C(O)OH, —(CH$_2$)$_{1-5}$—C(O)(C$_1$-C$_6$ alkoxy), —(CH$_2$)$_{1-5}$—C(O)NH$_2$, —(CH$_2$)$_{1-5}$—C(O)NH(C$_1$-C$_6$ alkyl), —(CH$_2$)$_{1-5}$—C(O)N(C$_1$-C$_6$ alkyl)$_2$, —CH=CH—C(O)OH, —CH=CH—C(O)(C$_1$-C$_6$ alkoxy), —O(CH$_2$)$_{1-5}$—C(O)OH, —O(CH$_2$)$_{1-5}$—C(O)(C$_1$-C$_6$ alkoxy), (aryl)C$_1$-C$_6$ alkyl, or (heteroaryl)C$_1$-C$_6$ alkyl.

A second aspect of the invention provides compounds of formula (V):

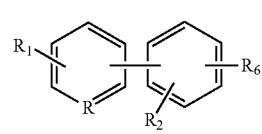

or a pharmaceutically acceptable salt thereof, wherein:
R is selected from N and CR$_5$;
  R$_5$ is selected from the group consisting of hydrogen, halogen, cyano, nitro, hydroxy, C$_1$-C$_6$ alkyl, C$_2$-C$_6$ alkenyl, C$_2$-C$_6$ alkynyl, halo(C$_1$-C$_6$ alkyl), C$_1$-C$_6$ alkoxy, halo(C$_1$-C$_6$ alkoxy), amino, (C$_1$-C$_6$ alkyl)amino, di(C$_1$-C$_6$ alkyl)amino, hydroxy(C$_1$-C$_6$ alkyl), (C$_1$-C$_6$ alkoxy)C$_1$-C$_6$ alkyl, amino(C$_1$-C$_6$ alkyl), sulfanyl(C$_1$-C$_6$ alkyl), (C$_1$-C$_6$ alkyl)sulfanyl(C$_1$-C$_6$ alkyl), —(CH$_2$)$_{1-5}$—C(O)OH, —(CH$_2$)$_{1-5}$—C(O)(C$_1$-C$_6$ alkoxy), —(CH$_2$)$_{1-5}$—C(O)NH$_2$, (aryl)C$_1$-C$_6$ alkyl, and (heteroaryl)C$_1$-C$_6$ alkyl;
R$_1$ is hydrogen, halogen, hydroxy, C$_1$-C$_6$ alkyl, halo(C$_1$-C$_6$ alkyl), C$_1$-C$_6$ alkoxy, halo(C$_1$-C$_6$ alkoxy), hydroxy(C$_1$-C$_6$ alkyl), (C$_1$-C$_6$ alkoxy)C$_1$-C$_6$ alkyl, amino(C$_1$-C$_6$ alkyl), sulfanyl(C$_1$-C$_6$ alkyl), or (C$_1$-C$_6$ alkyl)sulfanyl(C$_1$-C$_6$ alkyl);
R$_2$ is C$_1$-C$_6$ alkyl, halo(C$_1$-C$_6$ alkyl), C$_1$-C$_6$ alkoxy, halo(C$_1$-C$_6$ alkoxy), hydroxy(C$_1$-C$_6$ alkyl), (C$_1$-C$_6$ alkoxy)C$_1$-C$_6$ alkyl, formyl(C$_0$-C$_6$ alkyl), amino(C$_1$-C$_6$ alkyl), sulfanyl(C$_1$-C$_6$ alkyl), (C$_1$-C$_6$ alkyl)sulfanyl(C$_1$-C$_6$ alkyl), —(CH$_2$)$_{1-5}$—C(O)OH, —(CH$_2$)$_{1-5}$—C(O)(C$_1$-C$_6$ alkoxy), —(CH$_2$)$_{1-5}$—C(O)NH$_2$, —(CH$_2$)$_{1-5}$—C(O)NH ($C_1$-$C_6$ alkyl), —($CH_2$)$_{1-5}$—C(O)N($C_1$-$C_6$ alkyl)$_2$, —CH=CH—C(O)OH, —CH=CH—C(O)($C_1$-$C_6$ alkoxy), (aryl)$C_1$-$C_6$ alkyl, or (heteroaryl)$C_1$-$C_6$ alkyl; and $R_6$ is hydroxy, halogen, $C_1$-$C_6$ alkyl, $C_1$-$C_6$ alkoxy, halo($C_1$-$C_6$ alkoxy), benzyloxy, —($CH_2$)$_{1-5}$—C(O)OH, —($CH_2$)$_{1-5}$—C(O)($C_1$-$C_6$ alkoxy), —($CH_2$)$_{1-5}$—C(O)NH$_2$, —($CH_2$)$_{1-5}$—C(O)NH($C_1$-$C_6$ alkyl), —($CH_2$)$_{1-5}$—C(O)N($C_1$-$C_6$ alkyl)$_2$, —CH=CH—C(O)OH, —CH=CH—C(O)($C_1$-$C_6$ alkoxy), —OS(O)$_2$CF$_3$, (aryl)$C_1$-$C_6$ alkyl, or (heteroaryl)$C_1$-$C_6$ alkyl.

The compounds of this first and second aspect of the invention have been identified as novel GPBP inhibitors. We have reported that GPBP self-interacts and that aggregation regulates kinase activity (WO 00/50607). By combining a yeast two-hybrid system and cDNA deletion mutants of GPBP, we have identified a five-residue (SHCIE) (SEQ ID NO:1) motif in the GPBP amino acid sequence that is critical for self-interaction. A synthetic peptide representing the five-residue motif and flanking regions (LATLSHCIELM-VKR) (SEQ ID NO:2), referred to as $Q_2$, efficiently inhibited GPBP autophosphorylation and was shown to reduce α3(IV) NC1 conformer production by GPBP (see U.S. Pat. No. 7,326,768, incorporated by reference herein in its entirety). The compounds of the present invention are peptidomimetics of the core of the self-interaction site of $Q_2$ (SHCIE), and are shown herein to possess GPBP inhibitory activity, making them useful as therapeutics in antibody-mediated disorders, drug-resistant cancer, inflammation, protein misfolding and ER stress-mediated disorders, and aberrant apoptosis.

The invention also provides pharmaceutical compositions comprising a compound of this first or second aspect of the invention and at least one pharmaceutically acceptable carrier, solvent, adjuvant or diluent. The compounds or pharmaceutical compositions of the invention can be provided in a kit with instructions for using the compound or composition.

In a third aspect, the present invention provides methods for treating antibody-mediated disorders, drug-resistant cancer, inflammation, protein misfolding and ER stress-mediated disorders, and aberrant apoptosis comprising administering one or more compounds or pharmaceutical compositions of the invention to a subject in need thereof.

DETAILED DESCRIPTION OF THE INVENTION

In one preferred embodiment, the compounds of formula (I) are of formula (II):

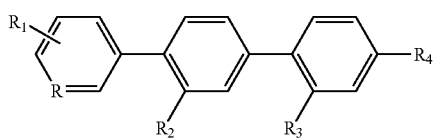

(II)

In another preferred embodiment, the disclosure provides compounds of formulae (I) or (II) wherein:

R is selected from N and CR$_5$;
  $R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), ($C_1$-$C_6$ alkyl)sulfanyl($C_1$-$C_6$ alkyl), —($CH_2$)$_{1-5}$—C(O)($C_1$-$C_6$ alkoxy), and —($CH_2$)$_{1-5}$—C(O)NH$_2$;

$R_1$ is hydrogen, halogen, hydroxy, $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), or ($C_1$-$C_6$ alkyl)sulfanyl($C_1$-$C_6$ alkyl);

$R_2$ is $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), ($C_1$-$C_6$ alkyl)sulfanyl($C_1$-$C_6$ alkyl), —($CH_2$)$_{1-5}$—C(O)OH, —($CH_2$)$_{1-5}$—C(O)($C_1$-$C_6$ alkoxy), or —($CH_2$)$_{1-5}$—C(O)NH$_2$;

$R_3$ is $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, formyl($C_1$-$C_6$ alkyl), amino($C_1$-$C_6$ alkyl), sulfanyl($C_1$-$C_6$ alkyl), ($C_1$-$C_6$ alkyl)sulfanyl($C_1$-$C_6$ alkyl), —($CH_2$)$_{1-5}$—C(O)OH, —($CH_2$)$_{1-5}$—C(O)($C_1$-$C_6$ alkoxy), —($CH_2$)$_{1-5}$—C(O)NH$_2$, —($CH_2$)$_{1-5}$—C(O)NH($C_1$-$C_6$ alkyl), —($CH_2$)$_{1-5}$—C(O)N($C_1$-$C_6$ alkyl)$_2$, —CH=CH—C(O)OH, or —CH=CH—C(O)($C_1$-$C_6$ alkoxy); and $R_4$ is hydroxy, halogen, $C_1$-$C_6$ alkyl, $C_1$-$C_6$ alkoxy, halo($C_1$-$C_6$ alkoxy), benzyloxy, —($CH_2$)$_{1-5}$—C(O)OH, —($CH_2$)$_{1-5}$—C(O)($C_1$-$C_6$ alkoxy), —($CH_2$)$_{1-5}$—C(O)NH$_2$, —($CH_2$)$_{1-5}$—C(O)NH($C_1$-$C_6$ alkyl), —($CH_2$)$_{1-5}$—C(O)N($C_1$-$C_6$ alkyl)$_2$, —CH=CH—C(O)OH, —CH=CH—C(O)($C_1$-$C_6$ alkoxy), —O($CH_2$)$_{1-5}$—C(O)OH, or —O($CH_2$)$_{1-5}$—C(O)($C_1$-$C_6$ alkoxy).

In another preferred embodiment, the disclosure provides compounds of formulae (I) or (II) wherein:

R is selected from N and CR$_5$;
  $R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl) amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);

$R_1$ is hydrogen, halogen, hydroxy, $C_1$-$C_6$ alkyl, halo($C_1$-$C_6$ alkyl), $C_1$-$C_6$ alkoxy, or halo($C_1$-$C_6$ alkoxy);

$R_2$ is $C_1$-$C_6$ alkyl, halo($C_1$-$C_6$ alkyl), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), or ($C_1$-$C_6$ alkyl)sulfanyl($C_1$-$C_6$ alkyl);

$R_3$ is $C_1$-$C_6$ alkyl, —($CH_2$)$_{1-5}$—C(O)OH, —($CH_2$)$_{1-5}$—C(O)($C_1$-$C_6$ alkoxy), —($CH_2$)$_{1-5}$—C(O)NH$_2$, —($CH_2$)$_{1-5}$—C(O)NH($C_1$-$C_6$ alkyl), —($CH_2$)$_{1-5}$—C(O)N($C_1$-$C_6$ alkyl)$_2$, —CH=CH—C(O)OH, or —CH=CH—C(O)($C_1$-$C_6$ alkoxy); and $R_4$ is hydroxy, halogen, $C_1$-$C_6$ alkyl, $C_1$-$C_6$ alkoxy, halo($C_1$-$C_6$ alkoxy), benzyloxy, —($CH_2$)$_{1-5}$—C(O)OH, —($CH_2$)$_{1-5}$—C(O)($C_1$-$C_6$ alkoxy), —($CH_2$)$_{1-5}$—C(O)NH$_2$, —($CH_2$)$_{1-5}$—C(O)NH($C_1$-$C_6$ alkyl), —($CH_2$)$_{1-5}$—C(O)N($C_1$-$C_6$ alkyl)$_2$, —CH=CH—C(O)OH, —CH=CH—C(O)($C_1$-$C_6$ alkoxy), —O($CH_2$)$_{1-5}$—C(O)OH, or —O($CH_2$)$_{1-5}$—C(O)($C_1$-$C_6$ alkoxy).

In another preferred embodiment, the disclosure provides compounds of formula (II), wherein R is N. These compounds can be represented by formula (III):

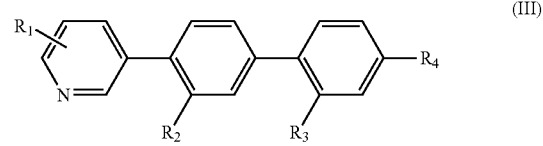

(III)

In yet another preferred embodiment, the disclosure provides compounds of formula (II), wherein R is CR$_5$. These compounds can be represented by formula (IV):

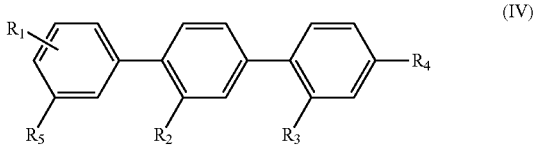

In one preferred embodiment, the disclosure provides compounds as described above with reference to any of formulae (I)-(IV), wherein R$_1$ is hydrogen, hydroxy, or C$_1$-C$_6$ alkoxy.

In one preferred embodiment, the disclosure provides compounds as described above with reference to any of formulae (I)-(IV), wherein R$_1$ is hydrogen.

In another preferred embodiment, the disclosure provides compounds as described above with reference to any of formulae (I)-(IV), wherein R$_2$ is C$_1$-C$_6$ alkyl, halo(C$_1$-C$_6$ alkyl), hydroxy(C$_1$-C$_6$ alkyl), formyl(C$_0$-C$_6$ alkyl), amino(C$_1$-C$_6$ alkyl), or sulfanyl(C$_1$-C$_6$ alkyl).

In yet another preferred embodiment, the disclosure provides compounds as described above with reference to any of formulae (I)-(IV), wherein R$_2$ is C$_1$-C$_6$ alkyl, halo(C$_1$-C$_6$ alkyl), hydroxy(C$_1$-C$_6$ alkyl), or formyl(C$_0$-C$_6$ alkyl).

In yet another preferred embodiment, the disclosure provides compounds as described above with reference to any of formulae (I)-(IV), wherein R$_2$ can be C$_1$-C$_6$ alkyl, halo(C$_1$-C$_6$ alkyl), or hydroxy(C$_1$-C$_6$ alkyl). For example, in certain embodiments R$_2$ can be C$_1$-C$_6$ alkyl such as methyl, ethyl, or isopropyl. In other embodiments, R$_2$ can be halo(C$_1$-C$_6$ alkyl) such as fluoromethyl, difluoromethyl, or trifluoromethyl. R$_2$ can, in certain embodiments, be hydroxy(C$_1$-C$_6$ alkyl). For example, the hydroxy(C$_1$-C$_6$ alkyl) can be hydroxymethyl, 1-hydroxyethyl, or 2-hydroxyethyl.

In another preferred embodiment, the disclosure provides compounds as described above with reference to any of formulae (I)-(IV), wherein R$_2$ is C$_1$-C$_6$ alkyl. In certain preferred embodiments R$_2$ is methyl.

In another preferred embodiment, the disclosure provides compounds as described above with reference to any of formulae (I)-(IV), wherein R$_3$ is C$_1$-C$_6$ alkyl, —(CH$_2$)$_{1-5}$—C(O)OH, —(CH$_2$)$_{1-5}$—C(O)(C$_1$-C$_6$ alkoxy), —CH═CH—C(O)OH, or —CH═CH—C(O)(C$_1$-C$_6$ alkoxy).

In another preferred embodiment, the disclosure provides compounds as described above with reference to any of formulae (I)-(IV), wherein R$_3$ is —(CH$_2$)$_{1-5}$—C(O)OH, —(CH$_2$)$_{1-5}$—C(O)(C$_1$-C$_6$ alkoxy), or —(CH$_2$)$_{1-5}$—C(O)NH$_2$.

In yet another preferred embodiment, the disclosure provides compounds as described above with reference to any of formulae (I)-(IV), wherein R$_3$ is —(CH$_2$)$_{1-2}$—C(O)OH, or —(CH$_2$)$_{1-2}$—C(O)(C$_1$-C$_6$ alkoxy). For example, in certain embodiments R$_3$ can be —(CH$_2$)$_2$—C(O)OH, —(CH$_2$)$_2$—C(O)(OCH$_3$), —(CH$_2$)$_2$—C(O)(OCH$_2$CH$_3$), or —(CH$_2$)$_2$—C(O)(OC(CH$_3$)$_3$). In other embodiments, R$_3$ can be —(CH$_2$)$_2$—C(O)OH, or —(CH$_2$)$_2$—C(O)(OCH$_2$CH$_3$).

In another preferred embodiment, the disclosure provides compounds as described above with reference to any of formulae (I)-(IV), wherein R$_3$ is —(CH$_2$)$_{1-2}$—C(O)OH. Preferably R$_3$ is —(CH$_2$)$_2$—C(O)OH.

In one preferred embodiment, the disclosure provides compounds as described above with reference to any of formulae (I)-(IV), wherein R$_4$ is hydroxy, halogen, C$_1$-C$_6$ alkyl, C$_1$-C$_6$ alkoxy, halo(C$_1$-C$_6$ alkoxy), or benzyloxy.

In another preferred embodiment, the disclosure provides compounds as described above with reference to any of formulae (I)-(IV), wherein R$_4$ is hydroxy or C$_1$-C$_6$ alkoxy (e.g., methoxy). Preferably R$_4$ is C$_1$-C$_6$ alkoxy. In more preferred embodiment, R$_4$ is methoxy.

In one preferred embodiment, the disclosure provides compounds as described above with reference to formulae (I), (II), or (IV), wherein R$_5$ is C$_1$-C$_6$ alkyl, halo(C$_1$-C$_6$ alkyl), C$_1$-C$_6$ alkoxy, or halo(C$_1$-C$_6$ alkoxy).

In another preferred embodiment, the disclosure provides compounds as described above with reference to formulae (I), (II), or (IV), wherein R$_5$ is C$_1$-C$_6$ alkyl, such as methyl.

In yet another preferred embodiment, the disclosure provides compounds as described above with reference to formulae (I), (II), or (IV), wherein R$_5$ is halo(C$_1$-C$_6$ alkyl), such as trifluoromethyl.

In certain preferred embodiments, the disclosure provides compounds of any of formulae (I), (II), or (IV), wherein:
R$_5$ is selected from the group consisting of hydrogen, halogen, cyano, nitro, hydroxy, C$_1$-C$_6$ alkyl, C$_2$-C$_6$ alkenyl, C$_2$-C$_6$ alkynyl, halo(C$_1$-C$_6$ alkyl), C$_1$-C$_6$ alkoxy, halo(C$_1$-C$_6$ alkoxy), amino, (C$_1$-C$_6$ alkyl)amino, di(C$_1$-C$_6$ alkyl)amino, hydroxy(C$_1$-C$_6$ alkyl), (C$_1$-C$_6$ alkoxy)C$_1$-C$_6$ alkyl, and amino(C$_1$-C$_6$ alkyl);
R$_1$ is hydrogen, halogen, hydroxy, C$_1$-C$_6$ alkyl, halo(C$_1$-C$_6$ alkyl), C$_1$-C$_6$ alkoxy, or halo(C$_1$-C$_6$ alkoxy);
R$_2$ is C$_1$-C$_6$ alkyl, halo(C$_1$-C$_6$ alkyl), hydroxy(C$_1$-C$_6$ alkyl), (C$_1$-C$_6$ alkoxy)C$_1$-C$_6$ alkyl, formyl(C$_0$-C$_6$ alkyl), amino(C$_1$-C$_6$ alkyl), sulfanyl(C$_1$-C$_6$ alkyl), or (C$_1$-C$_6$ alkyl)thio(C$_1$-C$_6$ alkyl);
R$_3$ is —(CH$_2$)$_{1-2}$—C(O)OH, —(CH$_2$)$_{1-2}$—C(O)(C$_1$-C$_6$ alkoxy), —(CH$_2$)$_{1-2}$—C(O)NH$_2$, —(CH$_2$)$_{1-2}$—C(O)NH(C$_1$-C$_6$ alkyl), —(CH$_2$)$_{1-2}$—C(O)N(C$_1$-C$_6$ alkyl)$_2$, —CH═CH—C(O)OH, —CH═CH—C(O)(C$_1$-C$_6$ alkoxy); and
R$_4$ is hydroxy, C$_1$-C$_6$ alkoxy, halo(C$_1$-C$_6$ alkoxy), or benzyloxy.

In certain preferred embodiments, the disclosure provides compounds of any of formula (III), wherein:
R$_1$ is hydrogen, halogen, hydroxy, C$_1$-C$_6$ alkyl, halo(C$_1$-C$_6$ alkyl), C$_1$-C$_6$ alkoxy, or halo(C$_1$-C$_6$ alkoxy);
R$_2$ is C$_1$-C$_6$ alkyl, halo(C$_1$-C$_6$ alkyl), hydroxy(C$_1$-C$_6$ alkyl), (C$_1$-C$_6$ alkoxy)C$_1$-C$_6$ alkyl, formyl(C$_0$-C$_6$ alkyl), amino(C$_1$-C$_6$ alkyl), sulfanyl(C$_1$-C$_6$ alkyl), or (C$_1$-C$_6$ alkyl)thio(C$_1$-C$_6$ alkyl);
R$_3$ is —(CH$_2$)$_{1-2}$—C(O)OH, —(CH$_2$)$_{1-2}$—C(O)(C$_1$-C$_6$ alkoxy), —(CH$_2$)$_{1-2}$—C(O)NH$_2$, —(CH$_2$)$_{1-2}$—C(O)NH(C$_1$-C$_6$ alkyl), —(CH$_2$)$_{1-2}$—C(O)N(C$_1$-C$_6$ alkyl)$_2$, —CH═CH—C(O)OH, —CH═CH—C(O)(C$_1$-C$_6$ alkoxy); and
R$_4$ is hydroxy, C$_1$-C$_6$ alkoxy, halo(C$_1$-C$_6$ alkoxy), or benzyloxy.

In certain preferred embodiments, the disclosure provides compounds of any of formulae (I), (II), or (IV), wherein R$_1$ is hydrogen; R$_2$ is C$_1$-C$_6$ alkyl, halo(C$_1$-C$_6$ alkyl), hydroxy(C$_1$-C$_6$ alkyl), or formyl(C$_1$-C$_6$ alkyl); R$_3$ is —(CH$_2$)$_{1-2}$—C(O)OH, —(CH$_2$)$_{1-2}$—C(O)(C$_1$-C$_6$ alkoxy), or —(CH$_2$)$_{1-2}$—C(O)NH$_2$; R$_4$ is hydroxy or C$_1$-C$_6$ alkoxy; and R$_5$ is C$_1$-C$_6$ alkyl, halo(C$_1$-C$_6$ alkyl), C$_1$-C$_6$ alkoxy, or halo(C$_1$-C$_6$ alkoxy).

In certain preferred embodiments, the disclosure provides compounds of any of formula (III), wherein R$_1$ is hydrogen; R$_2$ is C$_1$-C$_6$ alkyl, halo(C$_1$-C$_6$ alkyl), hydroxy(C$_1$-C$_6$ alkyl), or formyl(C$_1$-C$_6$ alkyl); R$_3$ is —(CH$_2$)$_{1-2}$—C(O)OH, —(CH$_2$)$_{1-2}$—C(O)(C$_1$-C$_6$ alkoxy), or —(CH$_2$)$_{1-2}$—C(O)

$NH_2$; $R_4$ is hydroxy or $C_1$-$C_6$ alkoxy; and $R_5$ is $C_1$-$C_6$ alkyl, halo($C_1$-$C_6$ alkyl), $C_1$-$C_6$ alkoxy, or halo($C_1$-$C_6$ alkoxy).

In certain preferred embodiments, the disclosure provides compounds of any of formulae (I)-(IV), wherein:
R, if present, is selected from N and $CR_5$;
  $R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);
$R_1$ is hydrogen;
$R_2$ is $C_1$-$C_6$ alkyl;
$R_3$ is —$(CH_2)_{1-2}$—C(O)OH; and
$R_4$ is $C_1$-$C_6$ alkoxy.

In certain preferred embodiments, the disclosure provides compounds of any of formulae (I)-(IV), wherein:
R, if present, is selected from N and $CR_5$;
  $R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);
$R_1$ is hydrogen;
$R_2$ is methyl;
$R_3$ is —$(CH_2)_2$—C(O)OH; and
$R_4$ is methoxy.

In one preferred embodiment, the compounds of formula (V) are of formula (VI):

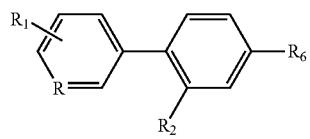

(VI)

In another preferred embodiment, the disclosure provides compounds of formulae (V) or (VI) wherein:
R is selected from N and $CR_5$;
  $R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), ($C_1$-$C_6$ alkyl)sulfanyl($C_1$-$C_6$ alkyl), —$(CH_2)_{1-5}$—C(O)OH, —$(CH_2)_{1-5}$—C(O)($C_1$-$C_6$ alkoxy), and —$(CH_2)_{1-5}$—C(O)$NH_2$;
$R_1$ is hydrogen, halogen, hydroxy, $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), or ($C_1$-$C_6$ alkyl)sulfanyl($C_1$-$C_6$ alkyl);
$R_2$ is $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), ($C_1$-$C_6$ alkyl)sulfanyl($C_1$-$C_6$ alkyl), —$(CH_2)_{1-5}$—C(O)OH, —$(CH_2)_{1-5}$—C(O)($C_1$-$C_6$ alkoxy), —$(CH_2)_{1-5}$—C(O)$NH_2$, —CH=CH—C(O)OH, or —CH=CH—C(O)($C_1$-$C_6$ alkoxy); and
$R_6$ is hydroxy, halogen, $C_1$-$C_6$ alkyl, $C_1$-$C_6$ alkoxy, halo($C_1$-$C_6$ alkoxy), benzyloxy, —$(CH_2)_{1-5}$—C(O)OH, —$(CH_2)_{1-5}$—C(O)($C_1$-$C_6$ alkoxy), —$(CH_2)_{1-5}$—C(O)$NH_2$, —$(CH_2)_{1-5}$—C(O)NH($C_1$-$C_6$ alkyl), —$(CH_2)_{1-5}$—C(O)N($C_1$-$C_6$ alkyl)$_2$, —CH=CH—C(O)OH, —CH=CH—C(O)($C_1$-$C_6$ alkoxy), or —OS(O)$_2$$CF_3$.

In another preferred embodiment, the disclosure provides compounds of formulae (V) or (VI) wherein:
R is selected from N and $CR_5$;
  $R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);
$R_1$ is hydrogen, halogen, hydroxy, $C_1$-$C_6$ alkyl, halo($C_1$-$C_6$ alkyl), $C_1$-$C_6$ alkoxy, or halo($C_1$-$C_6$ alkoxy);
$R_2$ is $C_1$-$C_6$ alkyl, halo($C_1$-$C_6$ alkyl), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), ($C_1$-$C_6$ alkyl)sulfanyl($C_1$-$C_6$ alkyl), —CH=CH—C(O)OH, or —CH=CH—C(O)($C_1$-$C_6$ alkoxy); and
$R_6$ is hydroxy, halogen, $C_1$-$C_6$ alkyl, $C_1$-$C_6$ alkoxy, halo($C_1$-$C_6$ alkoxy), benzyloxy, —$(CH_2)_{1-5}$—C(O)OH, —$(CH_2)_{1-5}$—C(O)($C_1$-$C_6$ alkoxy), —$(CH_2)_{1-5}$—C(O)$NH_2$, —$(CH_2)_{1-5}$—C(O)NH($C_1$-$C_6$ alkyl), —$(CH_2)_{1-5}$—C(O)N($C_1$-$C_6$ alkyl)$_2$, —CH=CH—C(O)OH, —CH=CH—C(O)($C_1$-$C_6$ alkoxy), or —OS(O)$_2$$CF_3$.

In one preferred embodiment, the disclosure provides compounds as described above with reference to any of formulae (V)-(VI), wherein $R_1$ is hydrogen.

In another preferred embodiment, the disclosure provides compounds as described above with reference to any of formulae (V)-(VI), wherein $R_2$ is $C_1$-$C_6$ alkyl, halo($C_1$-$C_6$ alkyl), hydroxy($C_1$-$C_6$ alkyl), formyl($C_0$-$C_6$ alkyl), amino ($C_1$-$C_6$ alkyl), sulfanyl($C_1$-$C_6$ alkyl), —CH=CH—C(O)OH, or —CH=CH—C(O)($C_1$-$C_6$ alkoxy).

In yet another preferred embodiment, the disclosure provides compounds as described above with reference to any of formulae (V)-(VI), wherein $R_2$ is $C_1$-$C_6$ alkyl, halo($C_1$-$C_6$ alkyl), hydroxy($C_1$-$C_6$ alkyl), formyl($C_0$-$C_6$ alkyl), —CH=CH—C(O)OH, or —CH=CH—C(O)($C_1$-$C_6$ alkoxy).

In yet another preferred embodiment, the disclosure provides compounds as described above with reference to any of formulae (V)-(VI), wherein $R_2$ can be $C_1$-$C_6$ alkyl, halo ($C_1$-$C_6$ alkyl), hydroxy($C_1$-$C_6$ alkyl), or —CH=CH—C(O)($C_1$-$C_6$ alkoxy). For example, in certain embodiments $R_2$ can be $C_1$-$C_6$ alkyl such as methyl, ethyl, or isopropyl. In other embodiments, $R_2$ can be halo($C_1$-$C_6$ alkyl) such as fluoromethyl, difluoromethyl, or trifluoromethyl. $R_2$ can, in certain embodiments, be hydroxy($C_1$-$C_6$ alkyl). For example, the hydroxy($C_1$-$C_6$ alkyl) can be hydroxymethyl, 1-hydroxyethyl, or 2-hydroxyethyl.

In another preferred embodiment, the disclosure provides compounds as described above with reference to any of formulae (V)-(VI), wherein $R_2$ is $C_1$-$C_6$ alkyl. In certain preferred embodiments $R_2$ is methyl.

In one preferred embodiment, the disclosure provides compounds as described above with reference to any of formulae (V)-(VI), wherein $R_6$ is hydroxy, halogen, $C_1$-$C_6$ alkyl, $C_1$-$C_6$ alkoxy, halo($C_1$-$C_6$ alkoxy), benzyloxy, or —OS(O)$_2$$CF_3$.

In another preferred embodiment, the disclosure provides compounds as described above with reference to any of formulae (V)-(VI), wherein $R_6$ is hydroxy or $C_1$-$C_6$ alkoxy (e.g., methoxy).

In one preferred embodiment, the disclosure provides compounds as described above with reference to formulae (V)-(VI), wherein $R_5$ is $C_1$-$C_6$ alkyl, halo($C_1$-$C_6$ alkyl), $C_1$-$C_6$ alkoxy, or halo($C_1$-$C_6$ alkoxy).

In another preferred embodiment, the disclosure provides compounds as described above with reference to formulae (V)-(VI), wherein $R_5$ is $C_1$-$C_6$ alkyl, such as methyl.

In yet another preferred embodiment, the disclosure provides compounds as described above with reference to formulae (V)-(VI), wherein $R_5$ is halo($C_1$-$C_6$ alkyl), such as trifluoromethyl.

In certain preferred embodiments, the disclosure provides compounds of any of formulae (V)-(VI), wherein:

$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);

$R_1$ is hydrogen, halogen, hydroxy, $C_1$-$C_6$ alkyl, halo($C_1$-$C_6$ alkyl), $C_1$-$C_6$ alkoxy, or halo($C_1$-$C_6$ alkoxy);

$R_2$ is $C_1$-$C_6$ alkyl, halo($C_1$-$C_6$ alkyl), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), ($C_1$-$C_6$ alkyl)thio($C_1$-$C_6$ alkyl), or —CH=CH—C(O)($C_1$-$C_6$ alkoxy); and $R_6$ is hydroxy, $C_1$-$C_6$ alkoxy, halo($C_1$-$C_6$ alkoxy), or —OS(O)$_2$CF$_3$.

In certain preferred embodiments, the disclosure provides compounds of any of formulae (V)-(VI), wherein $R_1$ is hydrogen; $R_2$ is $C_1$-$C_6$ alkyl, halo($C_1$-$C_6$ alkyl), hydroxy($C_1$-$C_6$ alkyl), formyl($C_0$-$C_6$ alkyl), or —CH=CH—C(O)($C_1$-$C_6$ alkoxy);

$R_6$ is hydroxy, $C_1$-$C_6$ alkoxy, or —OS(O)$_2$CF$_3$; and $R_5$ is $C_1$-$C_6$ alkyl, halo($C_1$-$C_6$ alkyl), $C_1$-$C_6$ alkoxy, or halo($C_1$-$C_6$ alkoxy).

The compounds of the invention include pharmaceutically acceptable salts, esters, amides, and prodrugs thereof, including but not limited to carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," J. Pharm. Sci., 1977; 66:1-19 which is incorporated herein by reference.)

Examples of pharmaceutically acceptable, non-toxic esters of the compounds of this invention include $C_1$-$C_6$ alkyl esters, wherein the alkyl group is a straight or branched, substituted or unsubstituted, $C_5$-$C_7$ cycloalkyl esters, as well as arylalkyl esters such as benzyl and triphenylmethyl. $C_1$-$C_4$ alkyl esters are preferred, such as methyl, ethyl, 2,2,2-trichloroethyl, and tert-butyl. Esters of the compounds of the present invention may be prepared according to conventional methods.

Examples of pharmaceutically acceptable, non-toxic amides of the compounds of this invention include amides derived from ammonia, primary $C_1$-$C_6$ alkyl amines and secondary $C_1$-$C_6$ dialkyl amines, wherein the alkyl groups are straight or branched. In the case of secondary amines, the amine may also be in the form of a 5- or 6-membered heterocycle containing one nitrogen atom. Amides derived from ammonia, $C_1$-$C_3$ alkyl primary amines and $C_1$-$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion of prodrugs is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference.

In one embodiment, the disclosure provides pharmaceutical compositions comprising a compound as described above with reference to any one of formulae (I)-(VI) and at least one pharmaceutically acceptable carrier, solvent, adjuvant or diluent.

For administration, the compounds are ordinarily combined with one or more adjuvants appropriate for the indicated route of administration. The compounds may be mixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The compounds of the invention can be administered as the sole active pharmaceutical agent, or they can be used in combination with one or more other compounds useful for carrying out the methods of the invention. When administered as a combination, the therapeutic agents can be formulated as separate compositions that are given at the same time or different times, or the therapeutic agents can be given as a single composition.

The compounds may be made up in a solid form (including granules, powders or suppositories) or in a liquid form (e.g., solutions, suspensions, or emulsions). The compounds of the invention may be applied in a variety of solutions and may be subjected to conventional pharmaceutical operations such as sterilization and/or may contain conventional adjuvants, such as preservatives, stabilizers, wetting agents, emulsifiers, buffers etc.

The compounds of the invention may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of the invention and a pharmaceutically acceptable carrier. One or more compounds of the invention may be present in association with one or more non-toxic pharmaceutically acceptable carriers and/or diluents and/or adjuvants, and if desired other active ingredients. The pharmaceutical compositions containing compounds of the invention may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative, and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds and pharmaceutical compositions of the present invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds and pharmaceutical compositions of the present invention may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

In a third aspect, the present invention provides methods for treating antibody-mediated disorders, drug-resistant cancer, inflammation, protein misfolding and ER stress-mediated disorders, and aberrant apoptosis comprising administering an amount effective of one or more compounds or pharmaceutical compositions of the invention to a subject in need thereof to treat the antibody-mediated disorder, drug-resistant cancer, inflammation, protein misfolding and ER stress-mediated disorder, or aberrant apoptosis. As used herein, the antibody-mediated disorders may comprise any immune-complex and autoimmune mediated disorder, such as a glomerulonephritis selected from the group consisting of IgA nephropathy, systemic lupus erythematosus and Goodpasture syndrome.

As used herein, "treat" or "treating" means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

Dosage levels of the order of from about 0.01 mg to about 50 mg per kilogram of body weight per day, and more preferably between 0.1 mg to about 50 mg per kilogram of body weight per day, are useful in the treatment of the above-indicated conditions. The amount of active ingredient that may be combined with the carrier materials to produce a single dosage form will vary depending upon the host treated and the particular mode of administration. Dosage unit forms will generally contain between from about 1 mg to about 500 mg of an active ingredient.

Compounds or pharmaceutical compositions containing the compounds described herein are administered to an individual in need thereof. In a preferred embodiment, the subject is a mammal; in a more preferred embodiment, the subject is a human. In therapeutic applications, compositions are administered in an amount sufficient to carry out the methods of the invention. Amounts effective for these uses depend on factors including, but not limited to, the nature of the compound (specific activity, etc.), the route of administration, the stage and severity of the disorder, the weight and general state of health of the subject, and the judgment of the prescribing physician. The active compounds are effective over a wide dosage range. However, it will be understood that the amount of the compound actually administered will be determined by a physician, in the light of the above relevant circumstances. Therefore, the above dosage ranges are not intended to limit the scope of the invention in any way.

Definitions

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term "alkylene" refers to a bivalent alkyl group. An "alkylene chain" is a polymethylene group, i.e., —(CH$_2$)$_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "halo" or "halogen" as used herein, means —Cl, —Br, —I or —F.

The terms "haloalkyl", "haloalkenyl" and "haloalkoxy" refer to an alkyl, alkenyl or alkoxy group, as the case may be, which is substituted with one or more halogen atoms.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a benzo ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

The present invention may be better understood with reference to the accompanying examples that are intended for purposes of illustration only and should not be construed to limit the scope of the invention.

EXAMPLES

Synthesis of $Q_2$ Peptidomimetics

New terphenyl compounds capable of mimicking the peptide $Q_2$ (SEQ ID NO:2)(U.S. Pat. No. 7,326,768) and modulating the kinase activity of GPBP are synthesized. Scheme 1 shows the terphenyl peptidomimetic proposed: every phenyl ring of this scaffold contains a different group that mimics the following amino acids:

a) alanine, serine and glutamic acid in the case of compound 1.

b) serine, glutamic acid and valine in the case of compound 2.

Scheme 1

$Q_2$: $CH_3CO$—L—A—T—L—S—H—C—I—E—L—M—V—K—R—$NH_2$ compound 1  A       S       E compound 2  S       E       V The synthetic strategy lies in a modular synthesis of 3,2',2''-tris-substituted-terphenyl derivatives by means of palladium catalysed cross coupling reactions between the different phenyl synthons (bromoaryls, aryltriflates, boronates and boronic acids).

Synthesis

In order to diversify and modify the solubility/lipophilicity of the terphenyl scaffold 1, the changes in the phenyl ring that mimics the alanine residue are introduced: a nitrogen atom and a trifluoromethyl group increase the family of terphenyl 1 derivates (Scheme 2).

Scheme 2

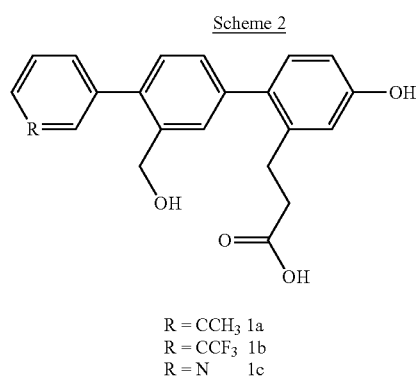

R = CCH₃  1a
R = CCF₃  1b
R = N     1c

The first step of this synthesis consisted of the regioselective bromination of commercial 3-hydroxybenzaldehyde in accordance with a known procedure. The resulting bromoaryl 3 reacted with several different commercial boronic acids or boronates to afford biphenyls 4 (Scheme 3).

Scheme 3

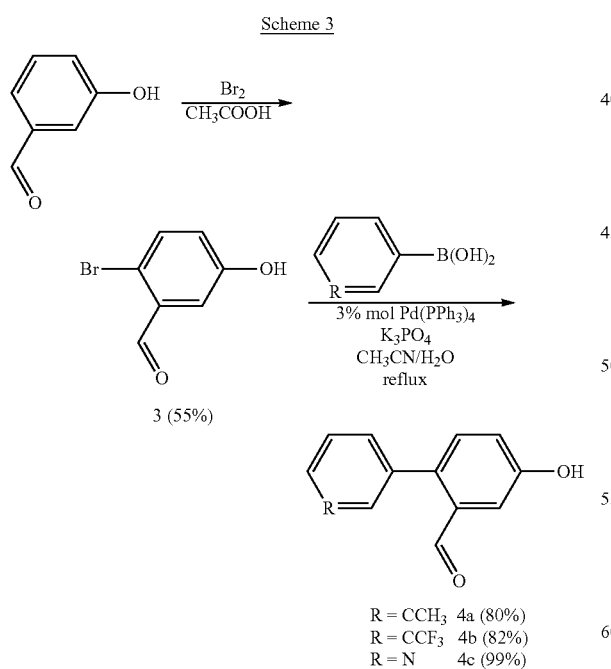

R = CCH₃  4a (80%)
R = CCF₃  4b (82%)
R = N     4c (99%)

In turn, phenols 4 were transformed into triflates 5 with triflic anhydride and pyridine as reagents. Triflates 5 reacted with boronate 6 under Suzuki coupling conditions to give terphenyls 7 (Scheme 4).

Scheme 4

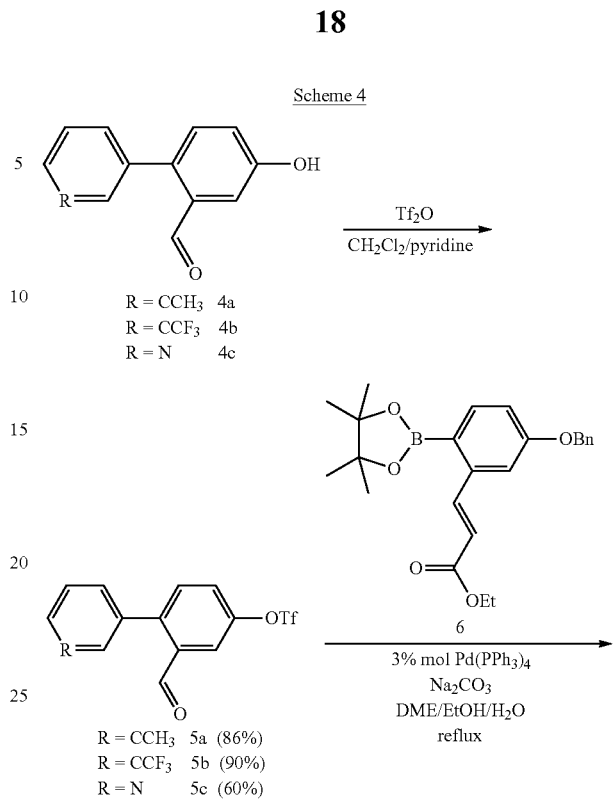

R = CCH₃  4a
R = CCF₃  4b
R = N     4c

R = CCH₃  5a (86%)
R = CCF₃  5b (90%)
R = N     5c (60%)

R = CCH₃  7a (85%)
R = CCF₃  7b (86%)
R = N     7c (82%)

Boronate 6 was previously synthesized from 2-bromo-5-hydroxybenzaldehyde 3 (Scheme 5).

Scheme 5

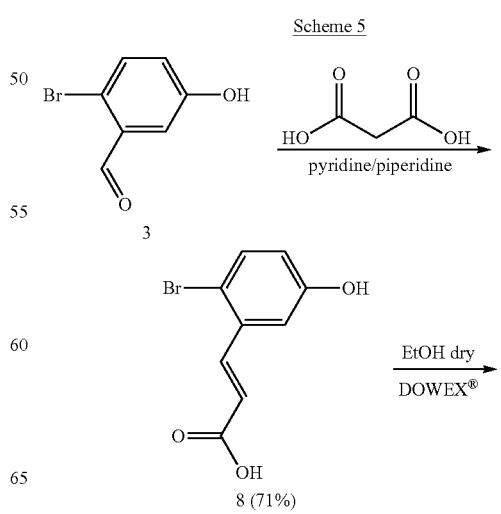

8 (71%)

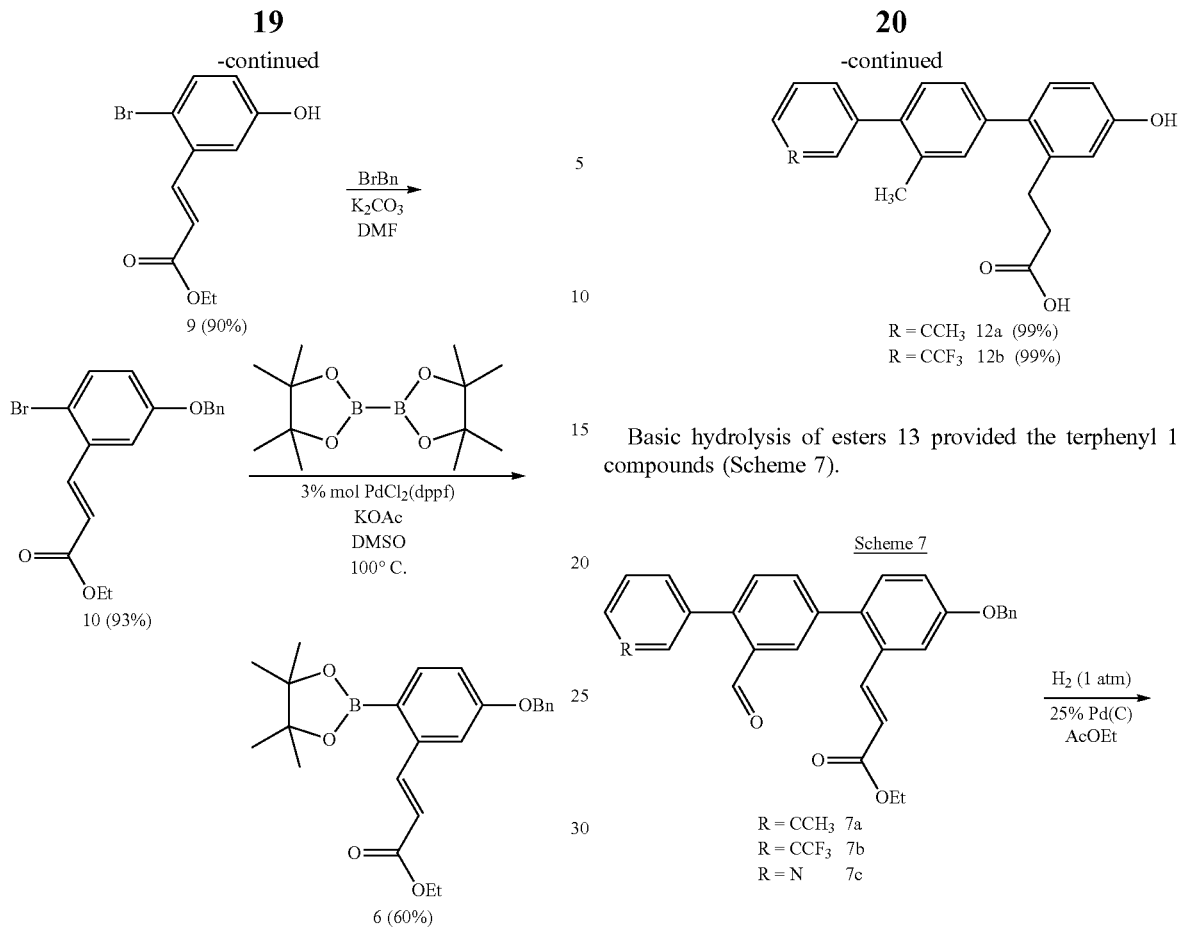

Catalytic hydrogenation of terphenyl intermediates 7 reduced the double bound, cleaved the benzyl group and also reduced the carbonyl group to methyl group to give compounds 11. Basic hydrolysis of ethyl esters provided final terphenylic compounds 12 (Scheme 6).

Basic hydrolysis of esters 13 provided the terphenyl 1 compounds (Scheme 7).

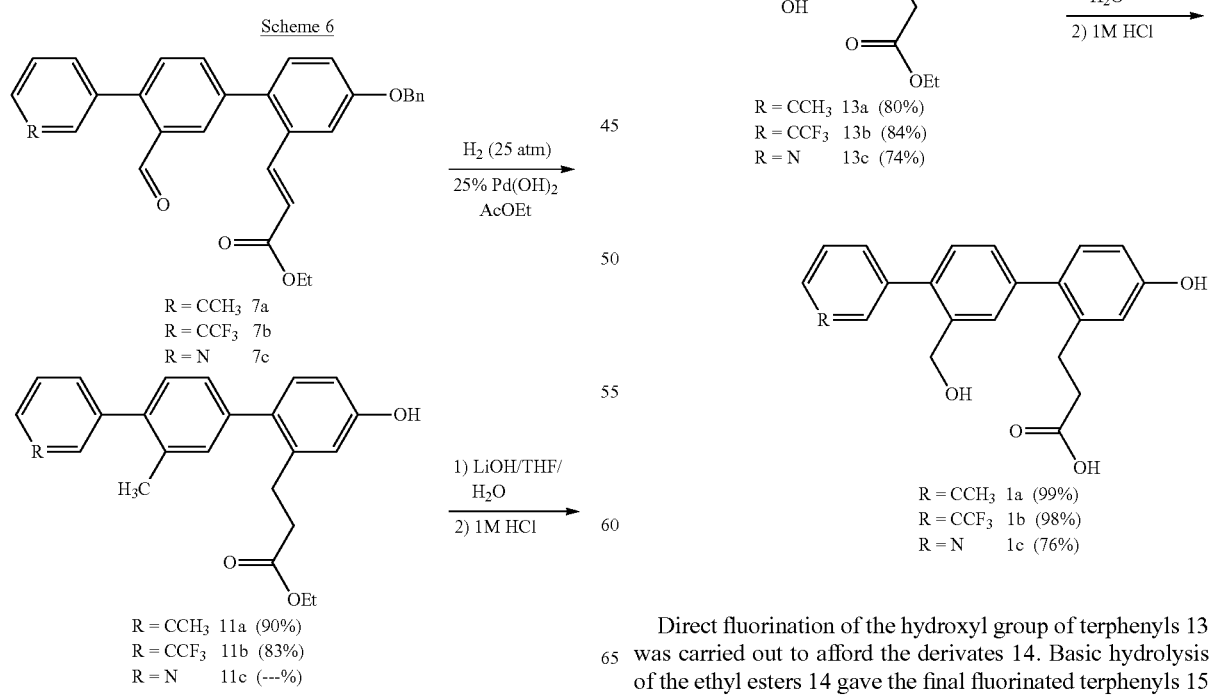

Direct fluorination of the hydroxyl group of terphenyls 13 was carried out to afford the derivates 14. Basic hydrolysis of the ethyl esters 14 gave the final fluorinated terphenyls 15 (Scheme 8).

Scheme 8

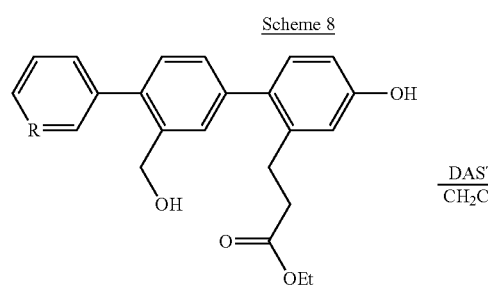

R = CCH₃  13a
R = CCF₃  13b
R = N     13c

DAST / CH₂Cl₂ →

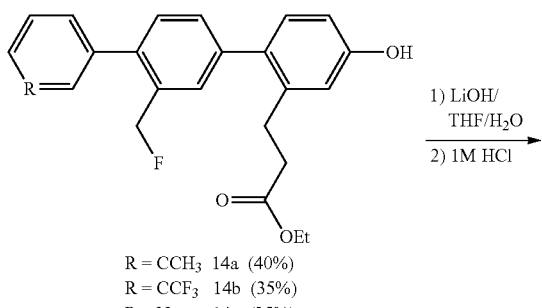

R = CCH₃  14a (40%)
R = CCF₃  14b (35%)
R = N     14c (35%)

1) LiOH/THF/H₂O
2) 1M HCl →

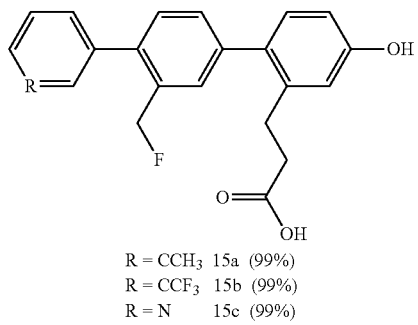

R = CCH₃  15a (99%)
R = CCF₃  15b (99%)
R = N     15c (99%)

Direct fluorination of the aldehyde group of terphenyls 7 was only achieved in compound 7c, so fluorination of the carbonyl group must be carried out with the biphenyls 4a,b. Difluorinated terphenyls 18a,b were obtained. After catalytic hydrogenation, basic hydrolysis of ethyl esters 19 gave the final difluorinated terphenyls 20 (Scheme 9).

Scheme 9

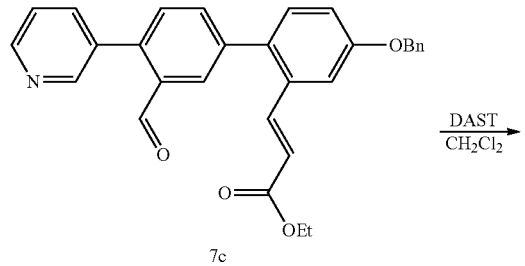

7c

DAST / CH₂Cl₂ →

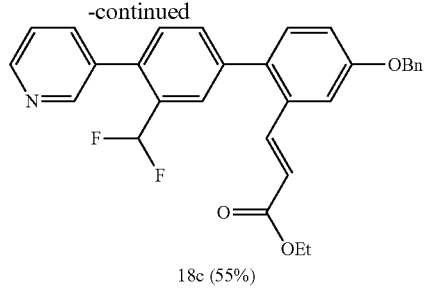

18c (55%)

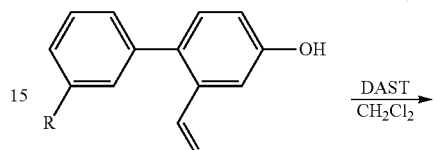

R = CH₃  4a
R = CF₃  4b

DAST / CH₂Cl₂ →

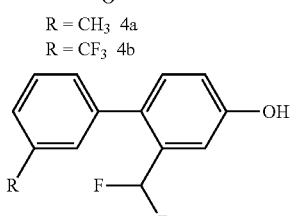

R = CH₃  16a (79%)
R = CF₃  16b (56%)

Tf₂O / CH₂Cl₂/pyridine →

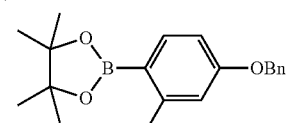

R = CH₃  17a (79%)
R = CF₃  17b (83%)

+ 6, 3% mol Pd(PPh₃)₄, Na₂CO₃, DME/EtOH/H₂O, reflux →

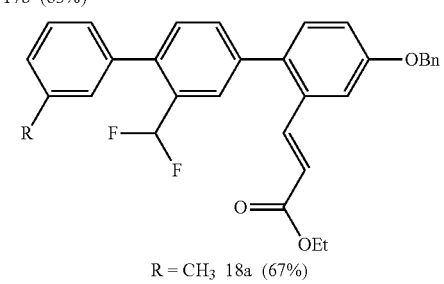

R = CH₃  18a (67%)
R = CF₃  18b (70%)

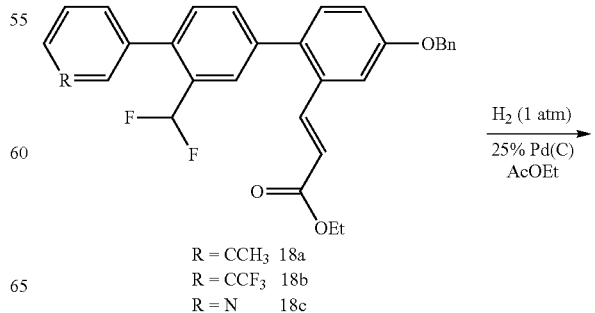

R = CCH₃  18a
R = CCF₃  18b
R = N     18c

H₂ (1 atm) / 25% Pd(C) / AcOEt →

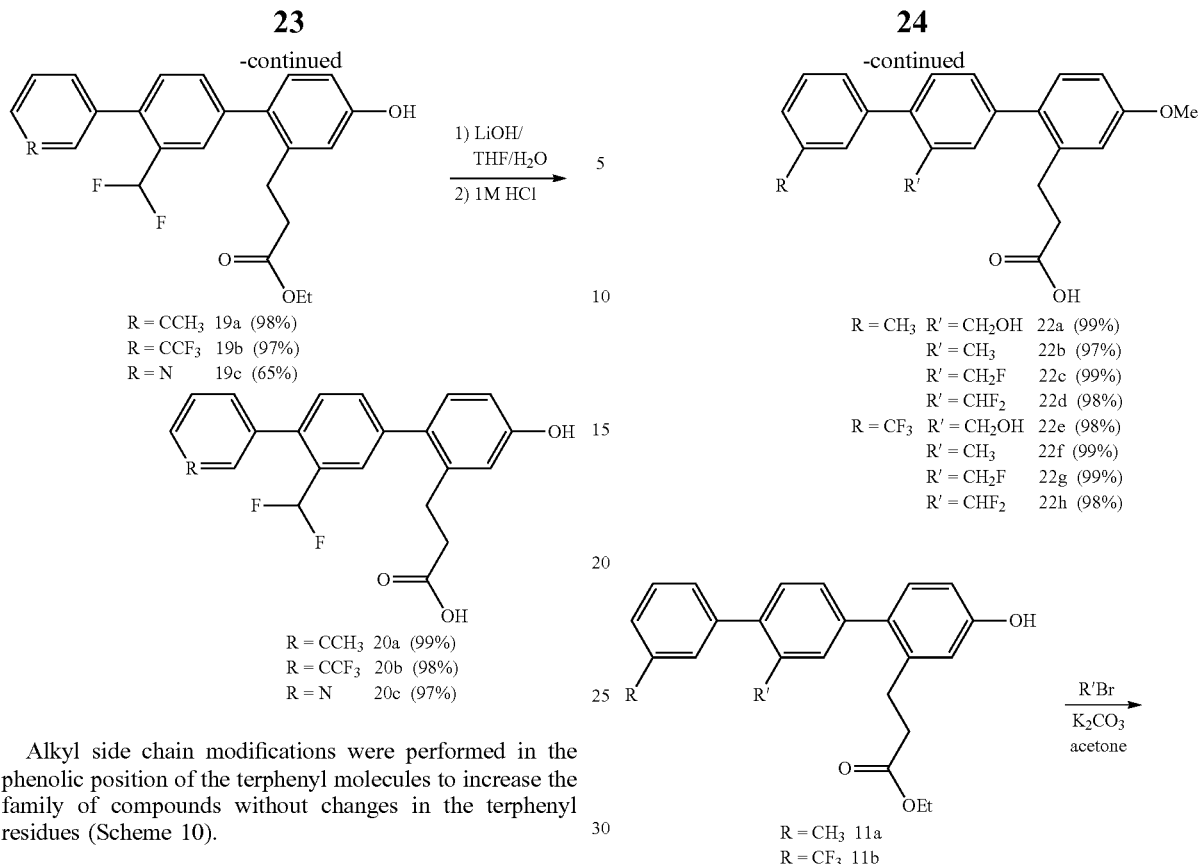
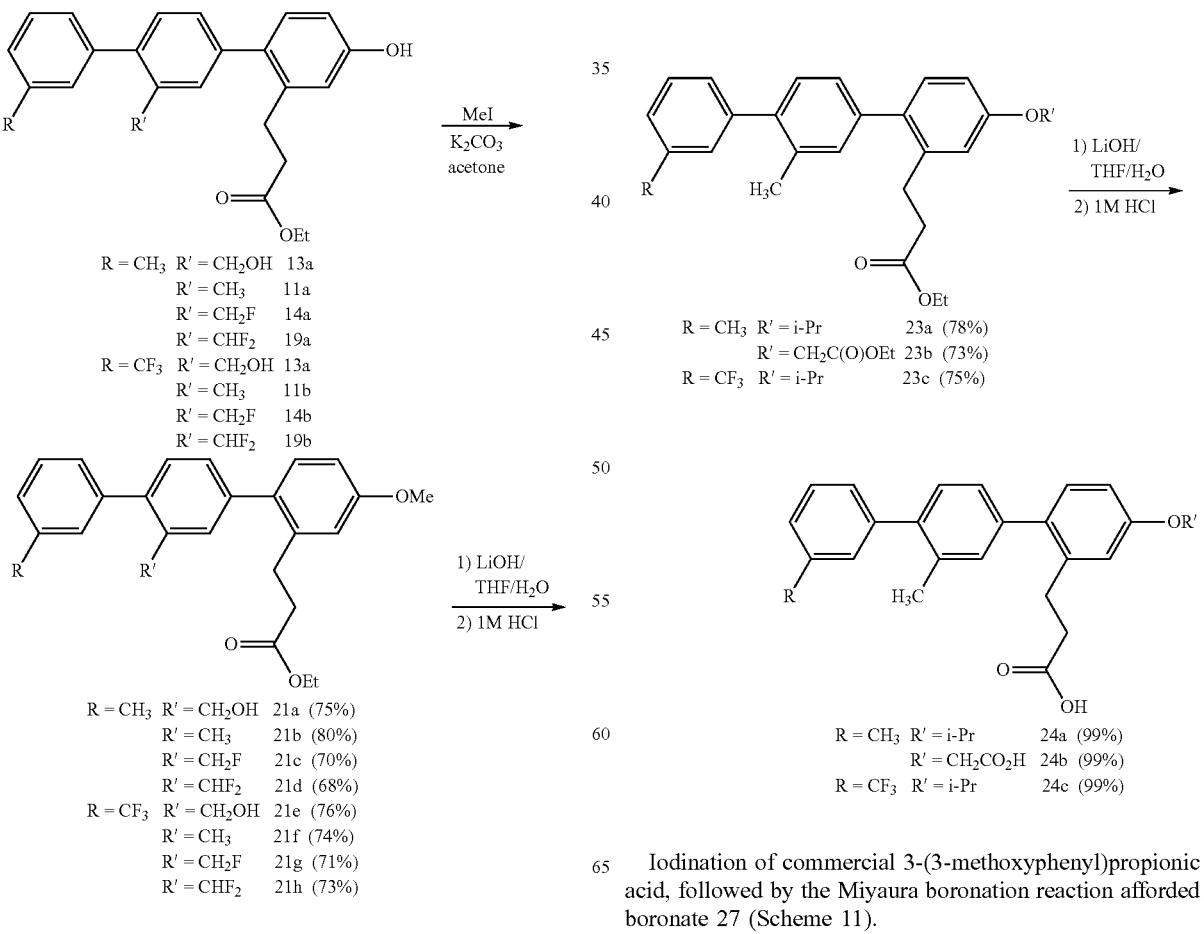
Alkyl side chain modifications were performed in the phenolic position of the terphenyl molecules to increase the family of compounds without changes in the terphenyl residues (Scheme 10).
Iodination of commercial 3-(3-methoxyphenyl)propionic acid, followed by the Miyaura boronation reaction afforded boronate 27 (Scheme 11).

Scheme 11

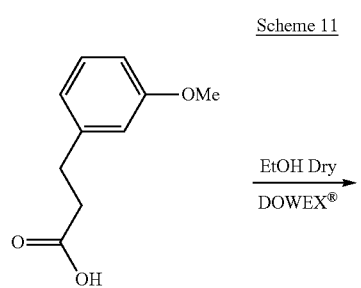

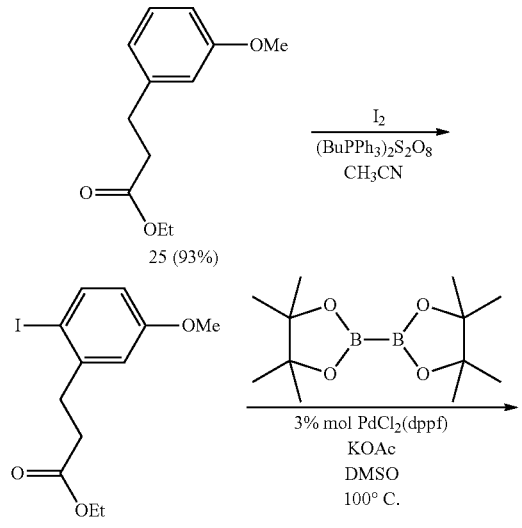

Boronate 27 was coupled with triflate 5c to afford the terphenyl 28 with similar reaction conditions to those described above. After carbonyl reduction and basic hydrolysis of the ethyl ester, compound 22i was obtained (Scheme 12).

Scheme 12

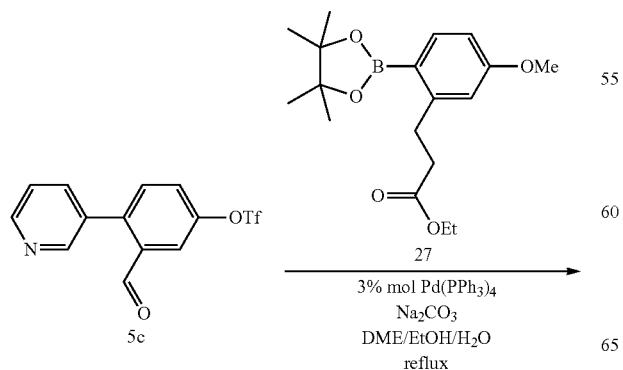

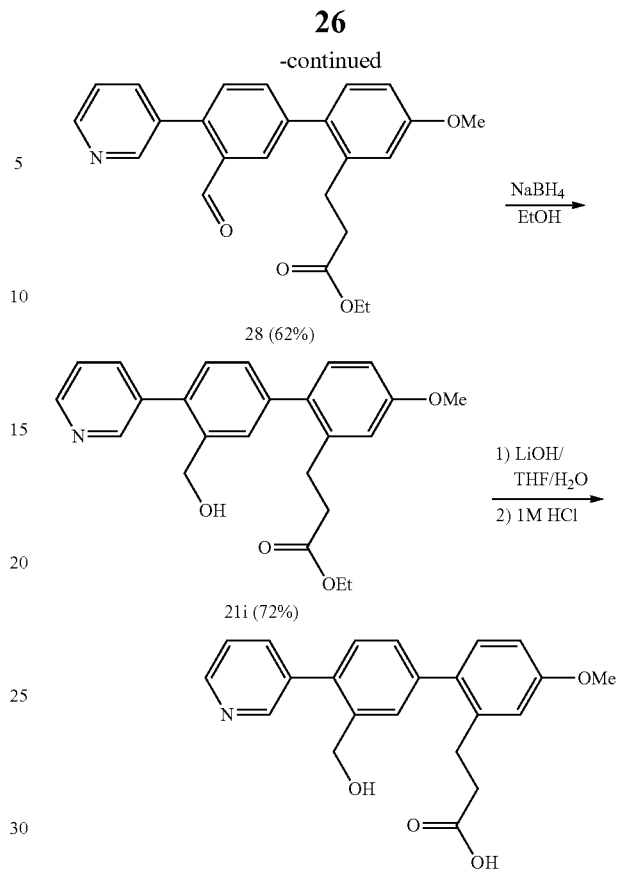

Terphenyl 22k was obtained from compound 21i after hydroxyl group fluorination and basic hydrolysis of the ethyl ester (Scheme 13).

Scheme 13

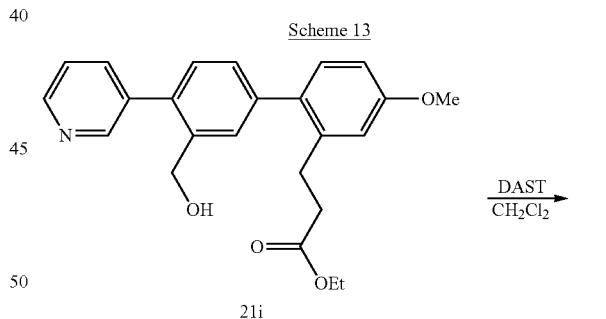

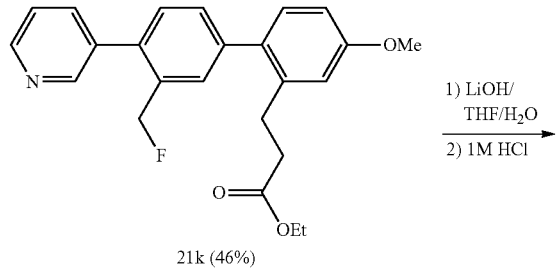

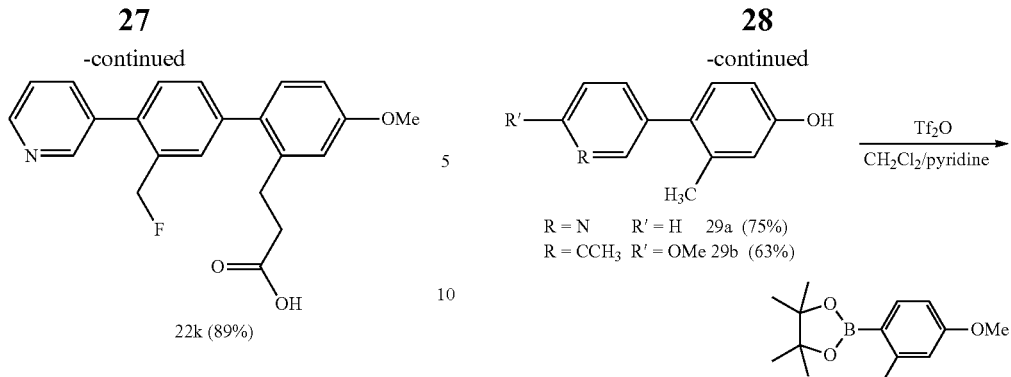
Direct fluorination of terphenyl 28 was achieved to give the compound 22l (Scheme 14).
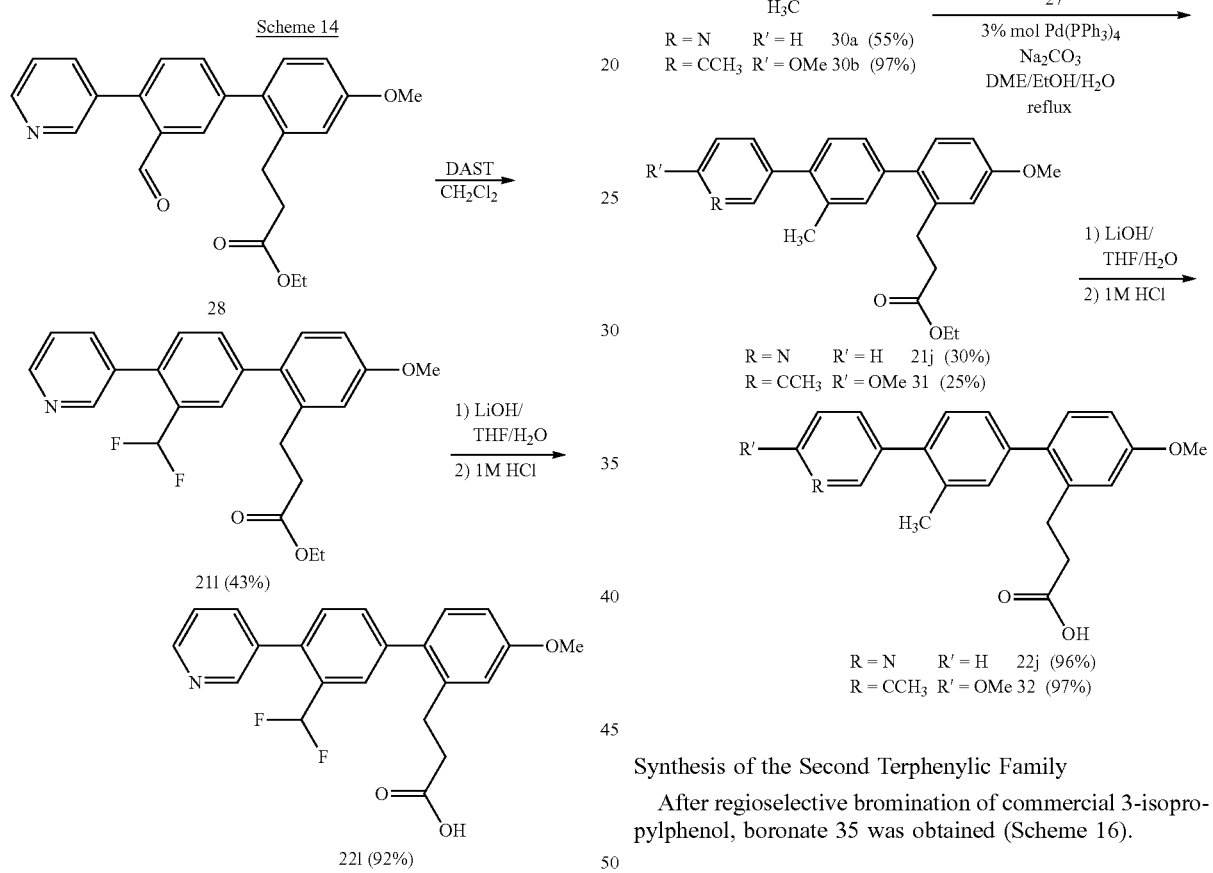
Finally, two more terphenylic compounds (22j and 32) were prepared with the same methodology described above (Scheme 15).
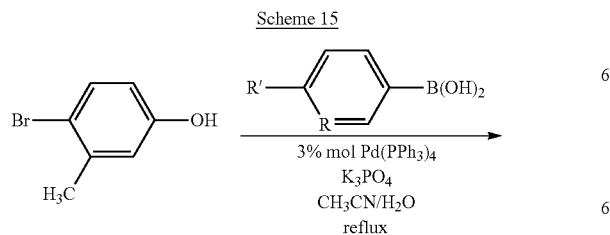
Synthesis of the Second Terphenylic Family
After regioselective bromination of commercial 3-isopropylphenol, boronate 35 was obtained (Scheme 16).
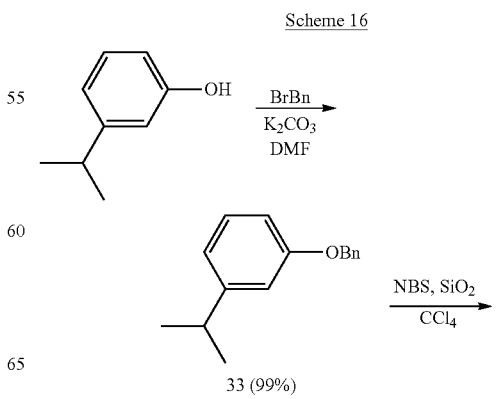

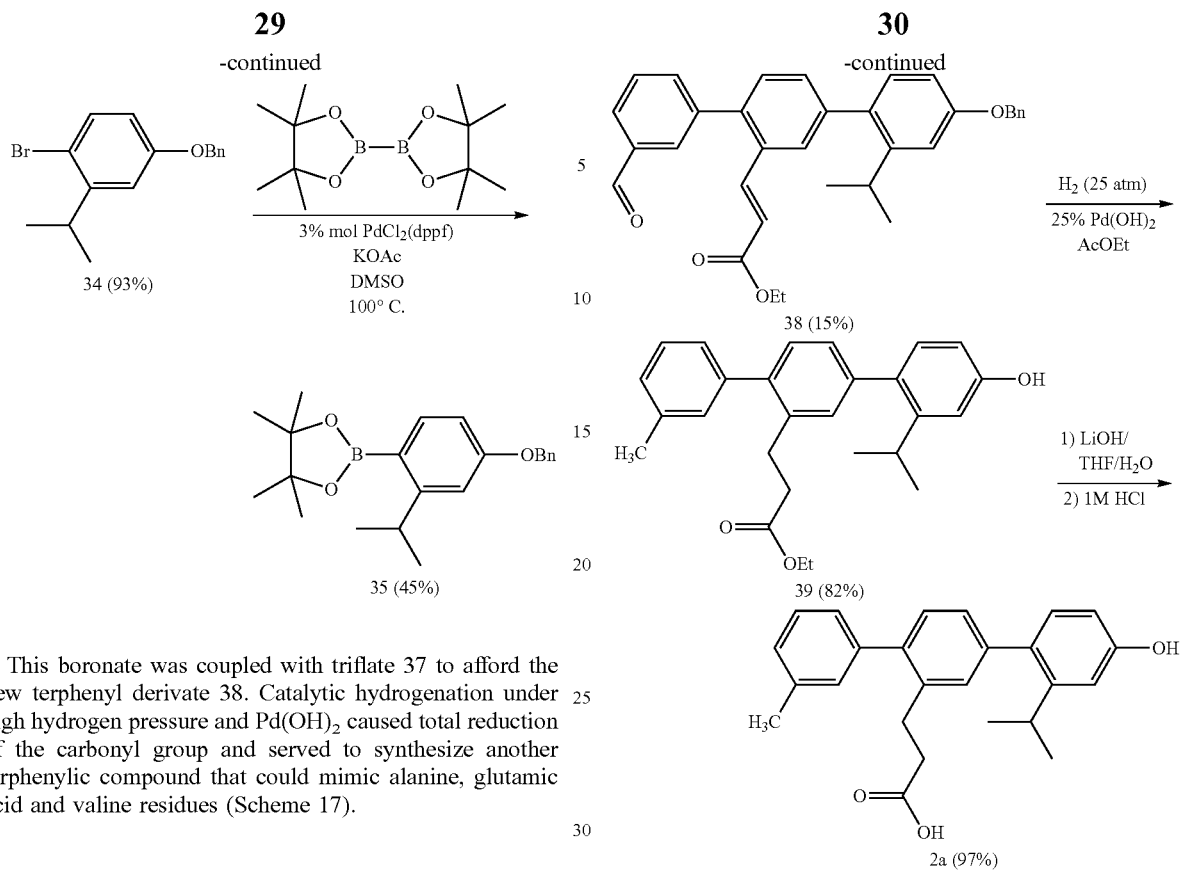

This boronate was coupled with triflate 37 to afford the new terphenyl derivate 38. Catalytic hydrogenation under high hydrogen pressure and Pd(OH)$_2$ caused total reduction of the carbonyl group and served to synthesize another terphenylic compound that could mimic alanine, glutamic acid and valine residues (Scheme 17).

Scheme 17

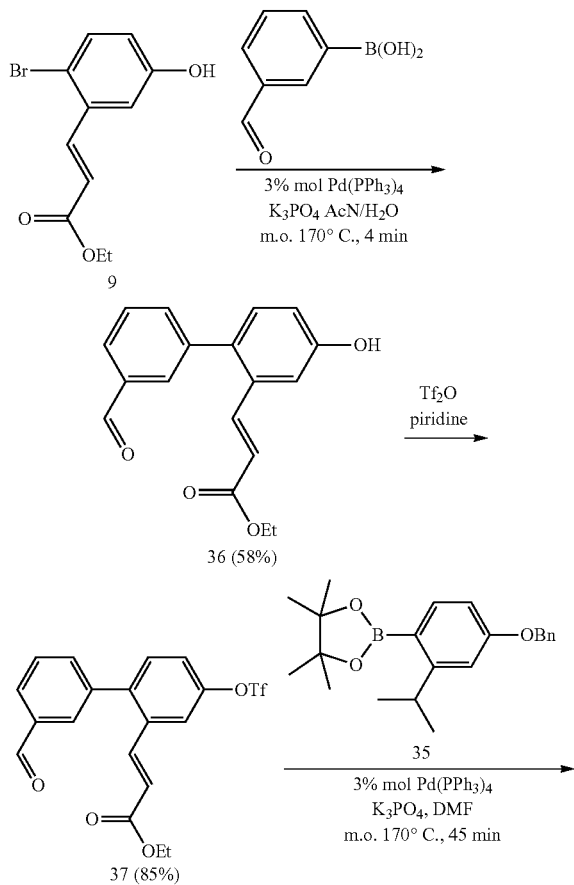

Experimental Procedures

General Method: The reactions were carried out under nitrogen atmosphere unless otherwise indicated. CH$_2$Cl$_2$ was distilled from calcium hydride prior to use. All other solvents and reagents were used as received unless otherwise stated. The reactions were monitored with the aid of thin-layer chromatography (TLC) on 0.25 mm E. Merk precoated silica gel plates. Visualization was carried out with UV light, aqueous ceric ammonium molybdate solution or potassium permanganate stain. Flash column chromatography was performed with the indicated solvents on silica gel 60 (particle size 0.040-0.063 mm). All compounds are colourless oils, if not otherwise stated. Melting points were measured with a "Büchi B-540" apparatus. $^1$H, $^{13}$C, and $^{19}$F NMR spectra were recorded on 300 MHz Bruker Advance spectrometer. Chemical shifts (δ) are given in ppm. Coupling constants (J) are given in Hertz (Hz). The letters m, s, d, t, and q stand for multiplet, singlet, doublet, triplet, and quartet, respectively. The letters br indicate that the signal is broad. High-resolution mass spectra measurements were carried out on a VGmAutospec instrument (VG Analytical, Micromass Instruments) by the Universitat de Valencia Mass Spectrometry Service.

Example 1: 2-bromo-5-hydroxybenzaldehyde (3)

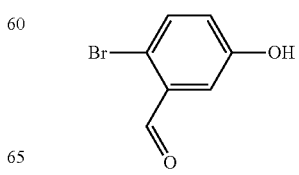

3-hydroxybenzaldehyde (10 g, 81.9 mmol) was dissolved in glacial acetic acid (50 mL) and cooled at 15° C. To the stirred solution, bromine (15.7 g, 98.2 mmol) was added dropwise while keeping the temperature below 22° C. After overnight stirring at room temperature, the volatiles were removed under vacuum without heating; the residue was co-evaporated three times with hexane (15 mL) and taken up in warm chloroform. Upon cooling, 9.05 g of 2-bromo-5-hydroxybenzaldehyde 3 were obtained as a white solid in two crops. Yield 55%. $^1$H NMR (300 MHz, CD$_3$COCD$_3$) δ ppm: 10.24 (s, 1H), 9.05 (s, 1H), 7.58 (d, J=8.7 Hz, 1H), 7.34 (d, J=3.1 Hz, 1H), 7.10 (dd, J$_1$=8.7 Hz, J$_2$=3.1 Hz, 1H); $^{13}$C NMR (75 MHz, CD$_3$COCD$_3$) δ ppm: 192.8, 159.3, 136.7, 136.2, 125.1, 117.3, 117.2; HRMS (EI) m/z: calcd for C$_7$H$_5$BrO$_2$: 199.9472, found: 199.9463; mp: 132-134° C.

General Procedure for the Synthesis of Biphenyls 4, 29 and 36

Bromoaryl (1 equiv), boronic acid or boronate (1.1 equiv), potassium phosphate (3 equiv) and palladium tetrakistriphenylphosfine (0.02 equiv) were dissolved in acetonitrile/water (7:3) and the resulting mixture was refluxed for 4 h under inert atmosphere. The reaction mixture was poured and aqueous layer was extracted with AcOEt. The combined organic layers were dried over Na$_2$SO$_4$, filtered and removed in vacuo. The resulting crude reaction product was purified by means of flash chromatography on silica gel.

Example 2: 4-hydroxy-3'-methylbiphenyl-2-carbaldehyde (4a)

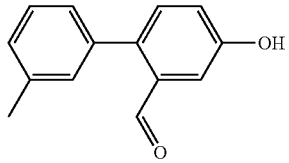 [SMILES: Cc1cccc(-c2ccc(O)cc2C=O)c1]

Yield 80% (hexane/AcOEt 10:1). $^1$H NMR (300 MHz, CDCl$_3$) δ ppm: 9.93 (s, 1H), 7.52 (d, J=2.7 Hz, 1H), 7.63 (t, J=8.1 Hz, 2H), 7.24 (d, J=7.8 Hz, 1H), 7.20-7.13 (m, 3H), 5.73 (s, 1H), 2.42 (s, 3H); $^{13}$C NMR (75 MHz, CDCl$_3$) δ ppm: 192.8, 155.3, 139.3, 138.1, 137.3, 134.5, 132.4, 130.9, 128.6, 128.3, 127.4, 121.4, 112.9, 21.4; HRMS (EI) m/z: calcd for C$_{14}$H$_{12}$O$_2$: 212.0837, found: 212.0827; white solid, mp: 148-150° C.

General Procedure for the Synthesis of Triflates 5, 17, 30 and 37

To a suspension of biphenyl (1 equiv) and pyridine (3 equiv) in dry CH$_2$Cl$_2$ (30 mL), triflic anhydride (1.5 equiv) solved in dry CH$_2$Cl$_2$ (20 mL) was added dropping under nitrogen atmosphere. The mixture was stirred overnight at r.t. and quenched with NaHCO$_3$ saturated solution (10 mL). The aqueous layer was extracted with CH$_2$Cl$_2$ and the combined organic layers were dried over Na$_2$SO$_4$, filtered, concentrated in vacuo and purified by flash chromatography on silica gel.

Example 3: 2-formyl-3'-methylbiphenyl-4-yl trifluoromethanesulfonate (5a)

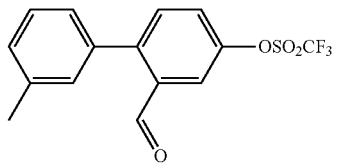

Yield 86% (hexane/AcOEt 10:1). $^1$H NMR (300 MHz, CDCl$_3$) δ ppm: 9.84 (s, 1H), 7.81 (d, J=1.8 Hz, 1H), 7.46 (d, J=3.0 Hz, 2H), 7.31 (t, J=7.5 Hz, 1H), 7.22 (d, J=7.5 Hz, 1H), 7.08 (d, J=8.7 Hz, 2H), 2.35 (s, 3H); $^{19}$F NMR (282 MHz, CDCl$_3$) δ ppm: −73.19 (s, 3F); $^{13}$C NMR (75 MHz, CDCl$_3$) δ ppm: 190.4, 148.9, 146.0, 138.6, 135.7, 135.2, 133.0, 130.7, 129.6, 128.6, 127.1, 126.1, 120.0, 118.7 (q, $^1$J=320.6 Hz), 21.4; HRMS (EI) m/z: calcd for C$_{15}$H$_{11}$F$_3$O$_4$S: 344.0330, found: 344.0325; white solid, mp: 60-62° C.

Example 4: (E)-3-(2-bromo-5-hydroxyphenyl) acrylic acid (8)

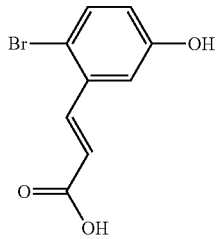 [SMILES: CCOC(=O)/C=C/c1cc(O)ccc1Br]

A mixture of bromoaryl 3 (5.5 g, 27.0 mmol), malonic acid (2.85 g, 27.0 mmol), pyridine (15 mL) and piperidine (0.5 mL) as catalyst were stirred overnight at 100° C. Thereafter, water (5 mL) was added and the mixture was neutralized with concentrated HCl. The resulting precipitate was filtered and crystallized from methanol to give 4.72 g of 7 as a white solid. Yield 71%. $^1$H NMR (300 MHz, CD$_3$COCD$_3$) δ ppm: 7.95 (d, J=15.8 Hz, 1H), 7.49 (d, J=8.4 Hz, 1H), 7.29 (d, J=3.0 Hz, 1H), 6.88 (dd, J$_1$=8.4 Hz, J$_2$=3.0 Hz, 1H), 6.44 (d, J=15.8 Hz, 1H), 2.88 (br s, 1H); $^{13}$C NMR (75 MHz, CD$_3$COCD$_3$) δ ppm: 168.2, 159.1, 144.4, 136.8, 135.9, 123.1, 121.2, 116.2, 104.2; HRMS (EI) m/z: calcd for C$_9$H$_7$BrO$_3$: 241.9579, found: 241.9515; mp: 208-210° C.

Example 5: (E)-ethyl 3-(2-bromo-5-hydroxyphenyl) acrylate (9)

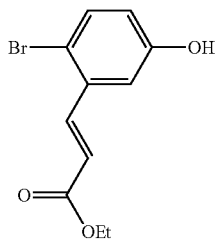

A solution of acrylic acid 8 (4.35 g, 18.0 mmol) in dry ethanol (50 mL) with a small quantity of acid resine DOWEX™ (300 mg) was refluxed for 24 h. The reaction mixture was filtered, the solvent was evaporated in vacuo and the crude reaction product was purificated by means of chromatography on silica gel (hexane/AcOEt 10:1) to give 4.36 g of ester 9 as a white solid. Yield 90%. $^1$H RMN (300 MHz, CD$_3$COCD$_3$) δ ppm: 8.82 (br s, 1H), 7.94 (d, J=16.1 Hz, 1H), 7.49 (d, J=8.7 Hz, 1H), 7.28 (d, J=2.9 Hz, 1H), 6.88 (dd, J$_1$=8.7 Hz, J$_2$=2.9 Hz, 1H), 6.45 (d, J=16.1 Hz, 1H), 4.24 (q, J=7.1 Hz, 2H), 1.30 (t, J=7.1 Hz, 3H); $^{13}$C RMN (75 MHz, CD$_3$COCD$_3$) δ ppm: 167.5, 159.1, 144.0, 136.7, 135.9, 123.0, 121.3, 116.2, 115.8, 62.1, 15.6; HRMS (EI) m/z: calcd for C$_{11}$H$_{11}$BrO$_3$: 269.9892, found: 269.9886; mp: 96-98° C.

Example 6: (E)-ethyl 3-[5-(benzyloxy)-2-bromophenyl]acrylate (10)

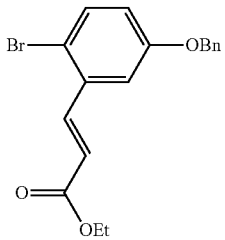 [SMILES: CCOC(=O)/C=C/c1cc(OCc2ccccc2)ccc1Br]

To a solution of ester 9 (4.9 g, 18.0 mmol) in anhydrous DMF (20 mL) was added potassium carbonate (5 g, 36.0 mmol) and benzyl bromide (3.38 g, 19.8 mmol). The reaction mixture was stirred overnight at room temperature, filtered and the solvent was removed under reduced pressure. The resulting crude reaction product was suspended in water and extracted with AcOEt. The combined organic layers were dried over Na$_2$SO$_4$, filtered, and the volatiles were removed in vacuo to give 6.06 g of bromoaryl 10 as a white solid. Yield 93%. $^1$H NMR (300 MHz, CDCl$_3$) δ ppm: 7.94 (d, J=15.9 Hz, 1H), 7.42 (d, J=8.7 Hz, 1H), 7.38-7.25 (m, 5H), 7.14 (d, J=3.0 Hz, 1H), 6.81 (dd, J$_1$=9.0 Hz, J$_2$=3.0 Hz, 1H), 6.29 (d, J=15.9 Hz, 1H), 5.00 (s, 2H), 4.23 (q, J=7.1 Hz, 2H), 1.29 (t, J=7.1 Hz, 3H); $^{13}$C NMR (75 MHz, CDCl$_3$) δ ppm: 166.2, 158.0, 142.8, 136.1, 135.1, 133.9, 128.6, 128.2, 127.4, 121.1, 118.3, 116.1, 113.6, 70.2, 60.6, 14.2; HRMS (EI) m/z: calcd for C$_{18}$H$_{17}$BrO$_3$: 360.0361, found: 360.0361; mp: 72-74° C.

General Procedure for the Synthesis of Boronates 6, 27 and 35

Haloaryl (1 equiv), bis(pinacolato)diboron (1.1 equiv), potassium acetate (3 equiv), and [1,1'-bis(diphenylphosphino)ferrocene]dichloropalladium(II) complex with dichloromethane (0.03 equiv) were dissolved in anhydrous dimethylsulfoxide (15 mL) and the resulting mixture was heated overnight at 110° C. under inert atmosphere. Then, solvent was removed under reduced pressure and the residue was suspended in water and extracted with AcOEt. The organic layers were dried over Na$_2$SO$_4$, filtered, and evaporated. The crude reaction product was purified by means of flash chromatography on silica gel.

Example 7: (E)-ethyl 3-[5-(benzyloxy)-2-(4,4,5,5-tetramethyl-1,3,2-dioxaborolan-2-yl)phenyl]acrylate (6)

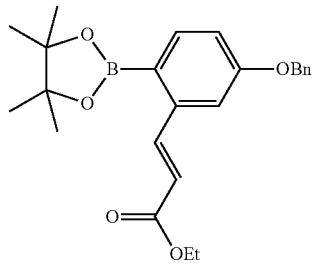 [SMILES: CCOC(=O)/C=C/c1cc(OCc2ccccc2)ccc1B1OC(C)(C)C(C)(C)O1]

Yield 60% (hexane/AcOEt 20:1). $^1$H NMR (300 MHz, CDCl$_3$) δ ppm: 8.54 (d, J=16.2 Hz, 1H), 7.73 (d, J=8.4 Hz, 1H), 7.40-7.24 (m, 5H), 7.21 (d, J=2.4 Hz, 1H), 6.92 (dd, J$_1$=8.4 Hz, J$_2$=2.4 Hz, 1H), 6.28 (d, J=16.2 Hz, 1H), 5.05 (s, 2H), 4.20 (q, J=7.1 Hz, 2H), 1.30 (s, 12H), 1.29 (t, J=7.1 Hz, 3H); $^{13}$C NMR (75 MHz, CDCl$_3$) (ppm: 167.1, 161.0, 145.5, 142.3, 138.1, 136.5, 128.6, 128.1, 127.4, 119.2, 115.8, 111.6, 83.8, 69.8, 60.3, 24.8, 14.3; HRMS (EI) m/z: calcd for C$_{24}$H$_{29}$BO$_5$: 407.2144, found: 407.2103; white solid, mp: 108-110° C.

General Procedure for the Synthesis of Terphenyls 7, 18, 21j, 28, 31 and 38

Triflate (1 equiv), boronate (1.2 equiv) and palladium tetrakistriphenylphosfine (0.03 equiv) were dissolved in DME/EtOH (9:1). Then, a 2 M aq. Na$_2$CO$_3$ solution (2 equiv) was added to this yellow solution and the resulting mixture was refluxed overnight. After concentrating the mixture in vacuo the residue was taken up in water and extracted with AcOEt. The combined organic fractions were dried over Na$_2$SO$_4$, filtered, and evaporated. The crude reaction product was purified by means of flash chromatography on silica gel.

Example 8: ethyl (E)-3-[4"-(benzyloxy)-2'-formyl-3-methyl-(1,1';4',1")terphenyl-2"-yl]acrylate (7a)

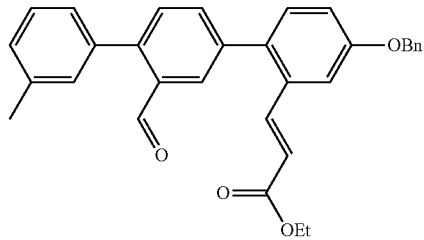 [SMILES: CCOC(=O)/C=C/c1cc(OCc2ccccc2)ccc1-c1ccc(-c2cccc(C)c2)c(C=O)c1]

Yield 85% (hexane/AcOEt 10:1). $^1$H NMR (300 MHz, CDCl$_3$) δ ppm: 10.07 (s, 1H), 8.06-7.97 (m, 1H), 7.74 (d, J=15.9 Hz, 1H), 7.63-7.23 (m, 13H), 7.13 (dd, J$_1$=8.6 Hz, J$_2$=2.3 Hz, 1H), 6.45 (d, J=15.9 Hz, 1H), 5.18 (s, 2H), 4.25 (q, J=7.1 Hz, 2H), 2.48 (s, 3H), 1.33 (t, J=7.2 Hz, 3H); $^{13}$C NMR (75 MHz, CDCl$_3$) δ ppm: 192.3, 166.6, 158.5, 144.9, 143.0, 139.1, 138.2, 137.2, 136.5, 134.9, 134.3, 133.7, 133.6, 131.7, 130.8, 130.6, 128.9, 128.6, 128.4, 128.3, 128.1, 127.5, 127.3, 119.0, 116.9, 112.5, 70.2, 60.4, 21.4, 14.2; HRMS (EI) m/z: calcd for C$_{32}$H$_{28}$O$_4$: 476.1988, found: 476.1985; white solid, mp: 90-92° C.

General Procedure for the Terphenyl Hydrogenation (Compounds 11, 13, 19 and 39)

A solution of terphenyl in AcOEt (15 mL) was hydrogenated overnight at room temperature under the following conditions:
1) 10% palladium hydroxide on carbon as catalyst (25% w/w) and 25 atm of pressure or
2) 10% palladium on carbon as catalyst (25% w/w) and 1 atm of pressure. Thereafter, the mixture was filtered over Celite and the filtrates concentrated in vacuo. The crude reaction product was purified by means of chromatography on silica gel.

Example 9: ethyl 3-[4"-hydroxy-2'-(hydroxymethyl)-3-methyl-(1,1';4',1")terphenyl-2"-yl]propionate (13a)

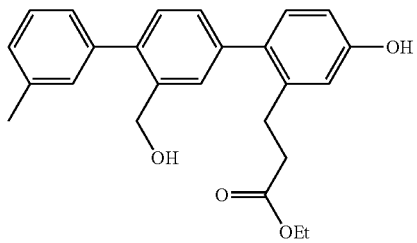 [SMILES: CCOC(=O)CCc1cc(O)ccc1-c1ccc(-c2cccc(C)c2)c(CO)c1]

Yield 80% (hexane/AcOEt 5:1). $^1$H NMR (300 MHz, CDCl$_3$) δ ppm: 7.39 (s, 1H), 7.27-7.07 (m, 6H), 6.99 (dd, $J_1$=8.1 Hz, $J_2$=2.1 Hz, 1H), 6.68 (s, 1H), 6.64 (dd, $J_1$=8.1 Hz, $J_2$=2.4 Hz, 1H), 4.59 (s, 2H), 3.97 (q, J=7.0 Hz, 2H), 2.81 (t, J=7.8 Hz, 2H), 2.36 (t, J=7.8 Hz, 2H), 2.32 (s, 3H), 1.09 (t, J=7.1 Hz, 3H); $^{13}$C NMR (75 MHz, CDCl$_3$) δ ppm: 173.6, 155.6, 140.3, 140.3, 139.6, 139.3, 137.9, 137.7, 133.6, 131.5, 129.9, 129.2, 128.5, 128.1, 128.0, 126.2, 115.9, 113.6, 63.1, 60.7, 35.4, 28.4, 21.5, 14.1; HRMS (EI) m/z: calcd for C$_{25}$H$_{26}$O$_4$: 390.1831, found: 390.1833; white solid, mp: 57-59° C.

General Procedure for the Basic Hydrolysis of Esters (Compounds 1, 2a, 12, 15, 20, 22 and 24)

Ester (1 equiv) was dissolved in a 4:1 tetrahydrofuran/water mixture (5 mL), monohydrated lithium hydroxide (3 equiv) added and the reaction was stirred at room temperature until completion. THF was removed under reduced pressure, the aqueous layer was acidified with 1 M HCl solution, and extracted with AcOEt. The organic layers were combined, dried over Na$_2$SO$_4$, filtered and removed in vacuo under reduced pressure.

Example 10: 3-[4"-hydroxy-2'-(hydroxymethyl)-3-methyl-(1,1';4',1")terphenyl-2"-yl]propionic acid (1a)

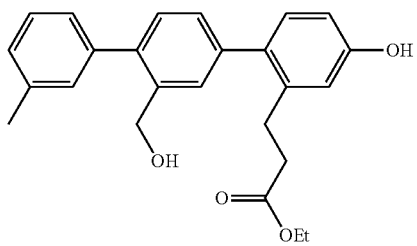 [SMILES: CCOC(=O)CCc1cc(O)ccc1-c1ccc(-c2cccc(C)c2)c(CO)c1]

Yield 99%. $^1$H NMR (300 MHz, CDCl$_3$) δ ppm: 7.50-7.12 (m, 7H), 7.03 (d, J=8.1 Hz, 1H), 6.82-6.62 (m, 2H), 6.08 (brs, 1H), 4.64 (s, 2H), 2.85 (t, J=6.3 Hz, 2H), 2.42 (t, J=6.9 Hz, 2H), 2.37 (s, 3H); $^{13}$C NMR (75 MHz, CDCl$_3$) δ ppm: 177.8, 155.2, 140.4, 140.2, 139.7, 139.0, 137.9, 137.2, 133.8, 131.5, 129.9 (2×), 129.3, 128.5, 128.1, 128.0, 126.2, 115.7, 113.6, 62.9, 35.0, 29.7, 21.4; HRMS (EI) m/z: calcd for C$_{23}$H$_{22}$O$_4$: 362.1518, found: 362.1516.

General Procedure for the Fluorination of Hydroxyls and Aldehydes (Compounds 14, 16, 21k and 21l)

Biphenyl or terphenyl (1 equiv) were dissolved in anhydrous dichloromethane (10 mL), DAST (2 equiv) was added and the reaction was stirred overnight at room temperature under nitrogen atmosphere. Then, the reaction mixture was hydrolyzed by addition of saturated NaHCO$_3$ solution. The aqueous layer was extracted with dichloromethane, the combined organic layers were dried over Na$_2$SO$_4$, filtered, and the solvent removed in vacuo under reduced pressure. The resulting crude reaction product was purified by means of flash chromatography on silica gel.

Example 11: ethyl 3-[2'-(fluoromethyl)-4"-hydroxy-3-methyl-(1,1';4',1")terphenyl-2"-yl]propionate (14a)

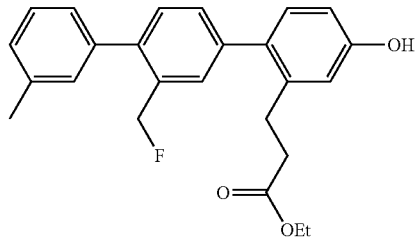 [SMILES: CCOC(=O)CCc1cc(O)ccc1-c1ccc(-c2cccc(C)c2)c(CF)c1]

Yield 40% (hexane/AcOEt 10:1). $^1$H RMN (300 MHz, CDCl$_3$) δ ppm: 7.39 (s, 1H), 7.31-7.10 (m, 6H), 7.05 (d, J=8.4 Hz, 1H), 6.73 (d, J=2.4 Hz, 1H), 6.69 (dd, $J_1$=8.3 Hz, $J_2$=2.3 Hz, 1H), 5.71 (br s, 1H), 5.25 (d, J=48.0 Hz, 2H), 4.01 (q, J=7.1 Hz, 2H), 2.87 (t, J=7.8 Hz, 2H), 2.41 (t, J=7.8 Hz, 2H), 2.34 (s, 3H), 1.12 (t, J=7.1 Hz, 3H); $^{19}$F RMN (282 MHz, CDCl$_3$) δ ppm: −200.6 (t, J=47.9 Hz, 1F); $^{13}$C RMN (75 MHz, CDCl$_3$) δ ppm: 173.3, 155.3, 140.6, 140.5, 139.7, 139.4, 137.9, 133.6, 133.1 (d, $^2$J=15.8 Hz), 131.6, 130.5 (d, $^3$J=6.5 Hz), 130.0 (2×), 129.9, 128.2, 128.1, 126.4, 115.7, 113.4, 82.8 (d, $^1$J=163.9 Hz), 60.6, 35.3, 28.3, 21.5, 14.1; HRMS (EI) m/z: calcd for C$_{25}$H$_{25}$FO$_3$: 392.1788, found: 392.1786.

General Procedure for the Alkylation Reaction (Compounds 21a-h and 23)

A solution of terphenyl (1 equiv), potassium carbonate (2 equiv) and alkyl halide (3 equiv) in acetone (5 mL) was heated at 70° C. in a microwave flask until completion. Then, the solvent was removed in vacuo and the crude reaction product was suspended in water. The aqueous layer was extracted with AcOEt and filtered and the combined organic layers were dried over Na$_2$SO$_4$, filtered and removed in vacuo under reduced pressure. The resulting crude reaction product was purified by means of flash chromatography on silica gel.

Example 12: ethyl 3-[2'-(hydroxymethyl)-4''-methoxy-3-methyl-(1,1';4',1'')terphenyl-2''-yl]propionate (21a)

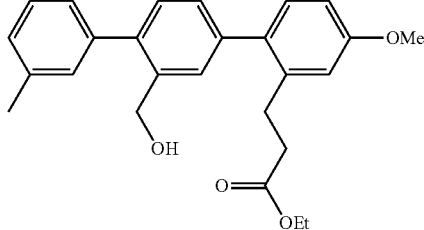

Yield 80% (hexane/AcOEt 10:1). $^1$H NMR (300 MHz, CDCl$_3$) δ ppm: 7.42 (d, J=1.5 Hz, 1H), 7.30-7.22 (m, 2H), 7.21-7.10 (m, 5H), 6.79 (d, J=2.8 Hz, 1H), 6.76 (dd, J$_1$=8.3 Hz, J$_2$=2.8 Hz, 1H), 4.60 (d, J=5.0 Hz, 2H), 4.02 (q, J=7.1 Hz, 2H), 3.78 (s, 3H), 2.90 (t, J=8.0 Hz, 2H), 2.45 (t, J=8.0 Hz, 2H), 2.35 (s, 3H), 1.14 (t, J=7.1 Hz, 3H); $^{13}$C NMR (75 MHz, CDCl$_3$) δ ppm: 173.1, 159.0, 140.4, 140.3, 139.7, 139.4, 137.9, 134.0, 131.3, 130.0, 129.9, 129.2, 128.5, 128.2, 128.0, 126.2, 114.6, 111.6, 63.3, 60.5, 55.3, 35.6, 28.7, 21.5, 14.2; HRMS (EI) m/z: calcd for C$_{26}$H$_{28}$O$_4$: 404.1987, found: 404.1992.

Example 13: 3-[4''-hydroxy-2'-(hydroxymethyl)-3-(trifluoromethyl)-(1,1';4',1'')terphenyl-2''-yl]propionic acid (1 b)

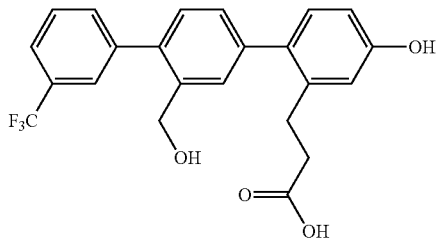

Yield 98%. $^1$H NMR (300 MHz, CD$_3$COCD$_3$) δ ppm: 8.40 (br s, 1H), 7.86 (s, 1H), 7.80 (d, J=6.9 Hz, 1H), 7.77-7.66 (m, 2H), 7.60 (s, 1H), 7.37 (d, J=8.1 Hz, 1H), 7.33 (d, J=7.8 Hz, 1H), 7.10 (d, J=8.4 Hz, 1H), 6.89 (d, J=2.1 Hz, 1H), 6.79 (dd, J$_1$=8.3 Hz, J$_2$=2.6 Hz, 1H), 4.59 (s, 2H), 2.92 (t, J=7.8 Hz, 2H), 2.50 (t, J=7.7 Hz, 2H); $^{19}$F NMR (282 MHz, CD$_3$COCD$_3$) δ ppm: −61.89 (s, 3F); $^{13}$C NMR (75 MHz, CD$_3$COCD$_3$) δ ppm: 175.0, 158.8, 143.6, 143.5, 141.5, 140.9, 139.5, 135.0, 134.7, 133.0, 131.8, 131.6 (q, $^2$J=31.7 Hz), 131.4, 130.9, 130.2, 127.7 (q, $^3$J=3.8 Hz), 126.4 (q, $^1$J=270.1 Hz), 125.6 (q, $^3$J=3.8 Hz), 117.6, 115.1, 63.6, 36.4, 30.0; HRMS (EI) m/z: calcd for C$_{23}$H$_{19}$F$_3$O$_4$: 416.1235, found: 416.1226; white solid, mp: 124-126° C.

Example 14: 3-[4-hydroxy-3'-(hydroxymethyl)-4'-(pyridin-3-yl)biphenyl-2-yl]propionic acid (1c)

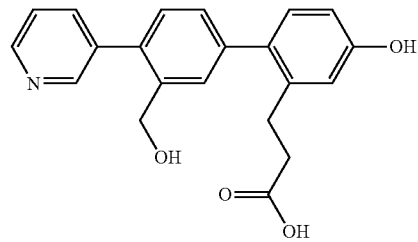 [SMILES: O=C(O)CCc1cc(O)ccc1-c1ccc(-c2cccnc2)c(CO)c1]

Yield 76%. $^1$H NMR (300 MHz, MeOD+drops CDCl$_3$) δ ppm: 8.63 (d, J=1.5 Hz, 1H), 8.54 (dd, J$_1$=4.8 Hz, J$_2$=1.2 Hz, 1H), 7.95 (ddd, J$_1$=7.9 Hz, J$_2$=2.2 Hz, J$_3$=1.7 Hz, 1H), 7.55-7.47 (m, 2H), 7.31 (d, J=1.1 Hz, 1H), 7.05 (d, J=8.3 Hz, 1H), 6.79 (d, J=2.5 Hz, 1H), 6.71 (dd, J$_1$=8.3 Hz, J$_2$=2.6 Hz, 1H), 4.53 (s, 2H), 2.90 (t, J=8.0 Hz, 2H), 2.44 (t, J=8.0 Hz, 2H); $^{13}$C NMR (75 MHz, MeOD+drops CDCl$_3$) δ ppm: 174.7, 155.9, 148.0, 146.4, 141.3, 138.5, 137.5, 136.9, 136.3, 134.6, 131.8, 130.1, 129.3, 128.8, 127.8, 122.7, 114.5, 112.2, 60.8, 34.2, 27.4; HRMS (EI) m/z: calcd for C$_{21}$H$_{19}$NO$_4$: 350.1392 (M+1), found: 350.1393; white solid, mp: 197-199° C.

Example 15: 3-[4''-hydroxy-2''-isopropyl-3-methyl-(1,1';4',1'')terphenyl-2'-yl]propionic acid (2a)

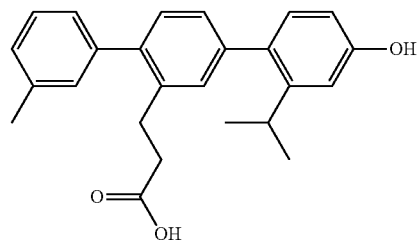

Yield 97%. $^1$H NMR (300 MHz, CDCl$_3$+drops MeOD) δ ppm: 7.18-7.26 (m, 1H), 7.02-7.15 (m, 6H), 6.97 (d, J=8.1 Hz, 1H), 6.78 (d, J=2.7 Hz, 1H), 6.61 (dd, J$_1$=8.1 Hz, J$_2$=2.7 Hz, 1H), 3.00 (sep, J=6.9 Hz, 1H), 2.89 (t, J=8.1 Hz, 2H), 2.38 (t, J=8.1 Hz, 2H), 2.32 (s, 3H), 1.08 (d, J=6.9 Hz, 6H); $^{13}$C NMR (75 MHz, CDCl$_3$+drops MeOD) δ ppm: 175.6, 156.0, 148.0, 141.3, 141.1, 140.1, 137.7, 137.3, 132.7, 131.0, 130.1, 129.9, 129.7, 128.0, 127.6, 127.3, 126.1, 112.4, 112.2, 35.0, 29.4, 28.2, 24.1, 21.3; HRMS (EI) m/z: calcd for C$_{25}$H$_{26}$O$_3$: 374.1882, found: 374.1881; white solid, mp: 183-185° C.

Example 16: 4-hydroxy-3'-(trifluoromethyl)biphenyl-2-carbaldehyde (4b)

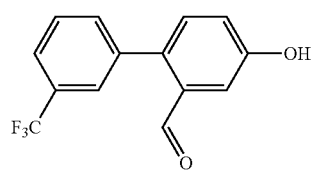 [SMILES: O=Cc1cc(O)ccc1-c1cccc(C(F)(F)F)c1]

Yield 82% (hexane/AcOEt 10:1). $^1$H NMR (300 MHz, CDCl$_3$) δ ppm: 9.89 (s, 1H), 7.69 (d, J=7.8 Hz, 1H), 7.63 (s, 1H), 7.59 (t, J=7.5 Hz, 1H), 7.52 (t, J=3.0 Hz, 2H), 7.35 (d, J=8.3 Hz, 1H), 7.19 (dd, J$_1$=8.3 Hz, J$_2$=2.8 Hz, 1H), 6.38 (br s, 1H); $^{19}$F NMR (282 MHz, CDCl$_3$) δ ppm: −63.11 (s, 3F); $^{13}$C NMR (75 MHz, CDCl$_3$) (ppm: 192.1, 156.2, 138.3, 137.3, 134.5, 133.6, 132.5, 131.0 (q, $^2$J=32.5 Hz), 128.9, 126.6 (q, $^3$J=3.7 Hz), 124.7 (q, $^3$J=3.8 Hz), 122.9 (q, $^1$J=270.9 Hz), 121.8, 113.6; HRMS (EI) m/z: calcd for C$_{14}$H$_9$F$_3$O$_2$: 266.0554, found: 266.0537; yellow solid, mp: 100-102° C.

Example 17:
5-hydroxy-2-(pyridin-3-yl)benzaldehyde (4c)

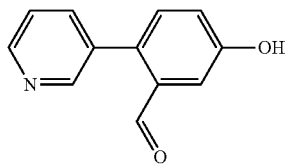 [SMILES: O=Cc1cc(O)ccc1-c1cccnc1]

Yield 99% (CH$_2$Cl$_2$/AcOEt 4:1). $^1$H NMR (300 MHz, DMSO-d$_6$) δ ppm: 10.16 (s, 1H), 9.80 (s, 1H), 8.61 (dd, J$_1$=4.8 Hz, J$_2$=1.5 Hz, 1H), 8.59 (d, J=2.1 Hz, 1H), 7.83 (dt, J$_1$=7.8 Hz, J$_2$=2.0 Hz, 1H), 7.49 (dd, J$_1$=7.2 Hz, J$_2$=4.8 Hz, 1H), 7.38 (d, J=8.1 Hz, 1H), 7.33 (d, J=2.7 Hz, 1H), 7.18 (dd, J$_1$=8.1 Hz, J$_2$=2.4 Hz, 1H); $^{13}$C NMR (75 MHz, DMSO-d$_6$) δ ppm: 191.2, 157.5, 149.8, 148.3, 137.2, 134.3, 133.3, 132.6, 132.3, 123.2, 121.4, 113.6; HRMS (EI) m/z: calcd for C$_{12}$H$_9$NO$_2$: 199.0633, found: 199.0607; white solid, mp: 182-184° C.

Example 18:
2-formyl-3'-(trifluoromethyl)biphenyl-4-yl trifluoromethanesulfonate (5b)

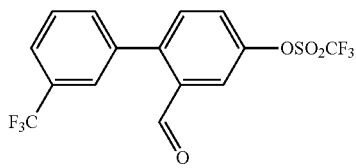

Yield 90% (hexane/AcOEt 10:1). $^1$H NMR (300 MHz, CDCl$_3$) δ ppm: 9.90 (s, 1H), 7.94 (d, J=1.7 Hz, 1H), 7.78 (d, J=7.5 Hz, 1H), 7.68 (d, J=7.2 Hz, 2H), 7.61-7.53 (m, 3H); $^{19}$F NMR (282 MHz, CDCl$_3$) δ ppm: −63.19 (s, 3F), −73.15 (s, 3F); $^{13}$C NMR (75 MHz, CDCl$_3$) δ ppm: 189.3, 149.5, 144.0, 136.8, 135.3, 133.3, 133.1, 131.5 (q, $^2$J=32.6 Hz), 129.3, 126.5, 126.4 (q, $^3$J=3.6 Hz), 125.7 (q, $^3$J=3.6 Hz), 123.7 (q, $^1$J=270.8 Hz), 120.6, 118.7 (q, $^1$J=318.9 Hz); HRMS (EI) m/z: calcd for C$_{15}$H$_8$F$_6$O$_4$S: 398.0047, found: 398.0039.

Example 19: 3-formyl-4-(pyridin-3-yl)phenyl trifluoromethanesulfonate (5c)

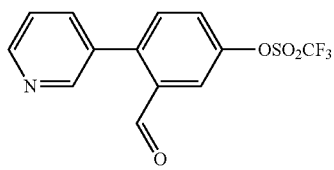

Yield 60% (CH$_2$Cl$_2$/AcOEt 5:1). $^1$H NMR (300 MHz, CDCl$_3$) δ ppm: 9.93 (s, 1H), 8.75 (dt, J$_1$=4.8 Hz, J$_2$=0.9 Hz, 1H), 8.67 (d, J=2.4 Hz, 1H), 7.95 (d, J=2.4 Hz, 1H), 7.73 (dt, J$_1$=7.8 Hz, J$_2$=2.7 Hz, 1H), 7.61 (dd, J$_1$=8.1 Hz, J$_2$=2.4 Hz, 1H), 7.56 (d, J=8.1 Hz, 1H), 7.47 (dd, J$_1$=7.8 Hz, J$_2$=4.8 Hz, 1H); $^{19}$F NMR (282 MHz, CDCl$_3$) δ ppm: −73.13 (s, 3F); $^{13}$C NMR (75 MHz, CDCl$_3$) δ ppm: 189.0, 150.1, 150.0, 149.6, 141.7, 137.1, 135.4, 133.2, 131.8, 126.6, 123.4, 120.8, 118.7 (q, $^1$J=318.9 Hz); HRMS (EI) m/z: calcd for C$_3$H$_8$F$_3$NO$_4$S: 332.0204 (M+1), found: 332.0124.

Example 20: (E)-ethyl 3-[4"-(benzyloxy)-2'-formyl-3-(trifluoromethyl)-(1,1';4',1")terphenyl-2"-yl]acrylate (7b)

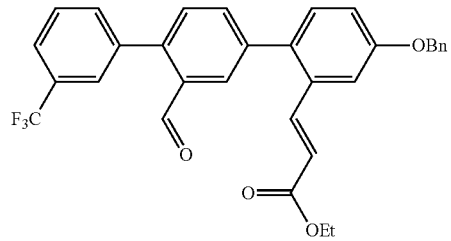 [SMILES: CCOC(=O)/C=C/c1cc(OCc2ccccc2)ccc1-c1ccc(-c2cccc(C(F)(F)F)c2)c(C=O)c1]

Yield 86% (hexane/AcOEt 10:1). $^1$H NMR (300 MHz, CDCl$_3$) δ ppm: 10.00 (s, 1H), 7.99 (d, J=2.1 Hz, 1H), 7.74 (br s, 2H), 7.67 (d, J=16.2 Hz, 2H), 7.63 (d, J=3.0 Hz, 1H), 7.58 (dd, J$_1$=7.8 Hz, J$_2$=1.8 Hz, 1H), 7.51-7.41 (m, 5H), 7.39 (dd, J$_1$=5.7 Hz, J$_2$=1.8 Hz, 1H), 7.35 (d, J=8.7 Hz, 2H), 7.32 (d, J=2.7 Hz, 1H), 7.11 (dd, J$_1$=8.4 Hz, J$_2$=2.7 Hz, 1H), 6.41 (d, J=15.9 Hz, 1H), 5.16 (s, 2H), 4.22 (q, J=7.0 Hz, 2H), 1.29 (t, J=7.2 Hz, 3H); $^{19}$F NMR (282 MHz, CDCl$_3$) δ ppm: −63.16 (s, 3F); $^{13}$C NMR (75 MHz, CDCl$_3$) δ ppm: 191.3, 166.6, 158.7, 142.9, 142.8, 140.2, 138.4, 136.5, 135.2, 133.9, 133.8, 133.6, 133.4, 131.7, 131.1 (q, $^2$J=32.4 Hz), 130.8, 129.2, 129.0, 128.7, 128.2, 127.5, 126.5 (q, $^3$J=3.7 Hz), 125.0 (q, $^3$J=3.9 Hz), 123.9 (q, $^1$J=270.4 Hz), 120.2, 117.0, 112.7, 70.3, 60.5, 14.2; HRMS (EI) m/z: calcd for C$_{32}$H$_{25}$F$_3$O$_4$: 530.1705, found: 530.1681; white solid, mp: 116-118° C.

Example 21: (E)-ethyl 3-[4-(benzyloxy)-3'-formyl-4'-(pyridin-3-yl)biphenyl-2-yl]acrylate (7c)

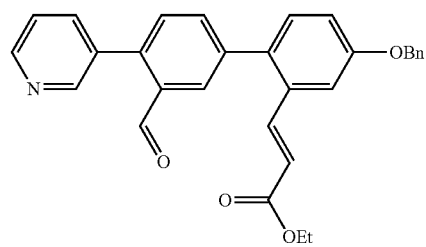 [SMILES: CCOC(=O)/C=C/c1cc(OCc2ccccc2)ccc1-c1ccc(-c2cccnc2)c(C=O)c1]

Yield 82% (CH$_2$Cl$_2$/AcOEt 10:1). $^1$H NMR (300 MHz, CDCl$_3$) δ ppm: 10.02 (s, 1H), 8.71 (dd, J$_1$=6.7 Hz, J$_2$=1.8 Hz, 1H), 7.99 (d, J=2.1 Hz, 1H), 7.77 (ddd, J$_1$=7.8 Hz, J$_2$=2.2 Hz, J$_3$=1.7 Hz, 1H), 7.66 (d, J=15.9 Hz, 1H), 7.58 (dd, J$_1$=7.9 Hz, J$_2$=2.0 Hz, 1H), 7.51-7.28 (m, 10H), 7.09 (dd, J$_1$=8.5 Hz, J$_2$=2.6 Hz, 1H), 6.41 (d, J=15.8 Hz, 1H), 5.14 (s, 2H), 4.20 (q, J=7.1 Hz, 2H), 1.28 (t, J=7.1 Hz, 3H);

¹³C NMR (75 MHz, CDCl₃) δ ppm: 190.9, 166.5, 158.6, 150.0, 149.3, 142.7, 140.4, 140.2, 137.1, 136.4, 135.1, 133.7, 133.7, 133.3, 131.6, 130.9, 129.4, 128.6, 128.1, 127.4, 123.1, 120.2, 116.9, 112.6, 70.1, 60.4, 14.2; HRMS (EI) m/z: calcd for C₃₀H₂₅NO₄: 464.1862 (M+1), found: 464.1869; yellowish solid, mp: 126-128° C.

Example 22: ethyl 3-[4"-hydroxy-2',3-dimethyl-(1,1';4',1")terphenyl-2"-yl]propionate (11a)

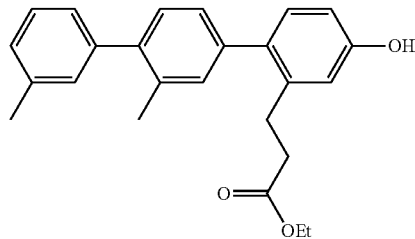 [SMILES: Cc1cccc(-c2ccc(-c3ccc(O)cc3CCC(=O)O)cc2C)c1]

Yield 90% (hexane/AcOEt 5:1). ¹H NMR (300 MHz, CDCl₃) δ ppm: 7.25 (t, J=7.4 Hz, 1H), 7.20-7.01 (m, 7H), 6.72 (d, J=2.1 Hz, 1H), 6.67 (dd, J₁=8.4 Hz, J₂=2.4 Hz, 1H), 5.18 (s, 1H), 4.02 (q, J=7.1 Hz, 2H), 2.88 (t, J=8.0 Hz, 2H), 2.41 (t, J=7.8 Hz, 2H), 2.34 (s, 3H), 2.23 (s, 3H), 1.14 (t, J=7.2 Hz, 3H); ¹³C NMR (75 MHz, CDCl₃) δ ppm: 173.2, 154.9, 141.6, 140.4, 140.0, 139.5, 137.6, 135.1, 134.4, 131.5, 131.3, 130.0, 129.6, 127.9, 127.5, 126.7, 126.3, 115.6, 113.2, 60.5, 35.4, 28.4, 21.5, 20.6, 14.1; HRMS (EI) m/z: calcd for C₂₅H₂₆O₃: 374.1882, found: 374.1881.

Example 23: ethyl 3-[4"-hydroxy-2'-methyl-3-(trifluoromethyl)-(1,1';4',1")terphenyl-2"-yl]propionate (11 b)

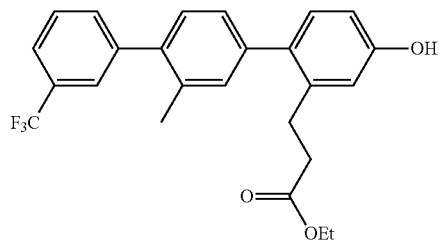 [SMILES: Cc1cc(-c2ccc(O)cc2CCC(=O)O)ccc1-c1cccc(C(F)(F)F)c1]

Yield 83% (hexane/AcOEt 10:1). ¹H NMR (300 MHz, CDCl₃) δ ppm: 7.60 (s, 1H), 7.58-7.52 (m, 1H), 7.50 (d, J=6.0 Hz, 2H), 7.19 (d, J=7.5 Hz, 1H), 7.14 (br s, 1H), 7.12 (dd, J₁=7.5 Hz, J₂=1.5 Hz, 1H), 7.06 (d, J=8.4 Hz, 1H), 6.75 (d, J=2.7 Hz, 1H), 6.70 (dd, J₁=8.4 Hz, J₂=2.7 Hz, 1H), 5.31 (s, 1H), 4.04 (q, J=7.2 Hz, 2H), 2.90 (t, J=8.0 Hz, 2H), 2.43 (t, J=8.0 Hz, 2H), 2.24 (s, 3H), 1.16 (t, J=7.2 Hz, 3H); ¹⁹F NMR (282 MHz, CDCl₃) δ ppm: −63.05 (s, 3F); ¹³C NMR (75 MHz, CDCl₃) δ ppm: 173.2, 155.1, 142.4, 140.9, 139.5, 138.8, 135.1, 134.1, 132.6, 131.6, 131.5, 130.6 (q, ²J=31.9 Hz), 129.5, 128.6, 127.0, 126.0 (q, ³J=3.8 Hz), 124.2 (q, ¹J=270.5 Hz), 123.6 (q, ³J=4.0 Hz), 115.7, 113.3, 60.5, 35.4, 28.4, 20.4, 14.1; HRMS (EI) m/z: calcd for C₂₅H₂₃F₃O₃: 428.1599, found: 428.1606.

Example 24: 3-[4"-hydroxy-2',3-dimethyl-(1,1';4',1")terphenyl-2"-yl]propionic acid (12a)

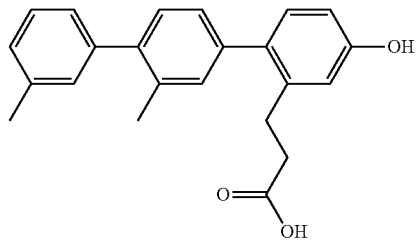

Yield 99%. ¹H NMR (300 MHz, CDCl₃) δ ppm: 7.25 (t, J=7.4 Hz, 1H), 7.21-7.03 (m, 7H), 6.79-6.63 (m, 2H), 2.89 (t, J=7.7 Hz, 2H), 2.45 (t, J=7.7 Hz, 2H), 2.35 (s, 3H), 2.24 (s, 3H); ¹³C NMR (75 MHz, CDCl₃) δ ppm: 178.4, 154.9, 141.6, 140.5, 139.9, 139.1, 137.6, 135.1, 134.5, 131.6, 131.2, 130.0, 129.6, 127.9, 127.5, 126.7, 126.3, 115.6, 113.4, 34.9, 28.1, 21.5, 20.6; HRMS (EI) m/z: calcd for C₂₃H₂₂O₃: 346.1569, found: 346.1562.

Example 25: 3-[4"-hydroxy-2'-methyl-3-(trifluoromethyl)-(1,1';4',1")terphenyl-2"-yl]propionic acid (12b)

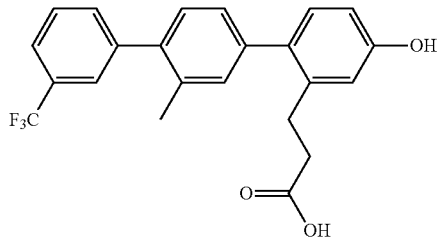

Yield 99%. ¹H NMR (300 MHz, CDCl₃) δ ppm: 7.57 (d, J=11.4 Hz, 2H), 7.49 (d, J=6.6 Hz, 2H), 7.18 (d, J=7.5 Hz, 1H), 7.13 (br s, 1H), 7.10 (dd, J₁=8.1 Hz, J₂=1.5 Hz, 1H), 7.06 (d, J=7.8 Hz, 1H), 6.74 (d, J=2.7 Hz, 1H), 6.70 (dd, J₁=8.3 Hz, J₂=2.6 Hz, 1H), 2.89 (t, J=7.8 Hz, 2H), 2.46 (t, J=8.0 Hz, 2H), 2.23 (s, 3H); ¹⁹F NMR (282 MHz, CDCl₃) δ ppm: −63.03 (s, 3F); ¹³C NMR (75 MHz, CDCl₃) (ppm: 178.4, 155.0, 142.3, 140.7, 139.1, 138.9, 135.1, 134.2, 132.6, 131.6, 131.5, 130.6 (q, ²J=32.0 Hz), 129.6, 128.6, 127.0, 126.0 (q, ³J=3.8), 124.2 (q, ¹J=270.5 Hz), 123.6 (q, ³J=3.9 Hz), 115.6, 113.4, 34.9, 28.0, 20.4; HRMS (EI) m/z: calcd for C₂₃H₁₉F₃O₃: 400.1286, found: 400.1282.

Example 26: ethyl 3-[4"-hydroxy-2'-(hydroxymethyl)-3-(trifluoromethyl)-(1,1';4',1")terphenyl-2"-yl]propionate (13b)

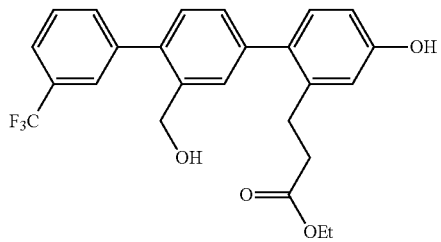

Yield 84% (hexane/AcOEt 4:1). $^1$H NMR (300 MHz, CDCl$_3$) δ ppm: 7.71 (s, 1H), 7.64 (d, J=7.5 Hz, 2H), 7.54 (t, J=8.1 Hz, 2H), 7.31 (d, J=8.1 Hz, 2H), 7.09 (d, J=8.4 Hz, 1H), 6.77 (d, J=2.4 Hz, 1H), 6.73 (dd, J$_1$=8.3 Hz, J$_2$=2.6 Hz, 1H), 6.39 (br s, 1H), 4.63 (s, 2H), 4.07 (q, J=7.2 Hz, 2H), 2.91 (t, J=7.8 Hz, 2H), 2.68 (br s, 1H), 2.47 (t, J=7.8 Hz, 2H), 1.19 (t, J=7.2 Hz, 3H); $^{19}$F NMR (282 MHz, CDCl$_3$) δ ppm: −63.01 (s, 3F); $^{13}$C NMR (75 MHz, CDCl$_3$) δ ppm: 173.6, 155.5, 141.3, 141.1, 139.3, 138.2, 137.7, 133.5, 132.6, 131.4, 130.7 (q, $^2$J=32.0 Hz), 129.9, 129.7, 128.8, 128.7, 126.0 (q, $^3$J=4.1 Hz), 124.1 (q, $^1$J=270.8 Hz), 124.0 (q, $^3$J=3.8 Hz), 115.8, 113.5, 62.9, 60.7, 35.4, 28.4, 14.1; HRMS (EI) m/z: calcd for C$_{25}$H$_{23}$F$_3$O$_4$: 444.1548, found: 444.1535.

Example 27: ethyl 3-[4-hydroxy-3'-(hydroxymethyl)-4'-(pyridin-3-yl)biphenyl-2-yl]propionate (13c)

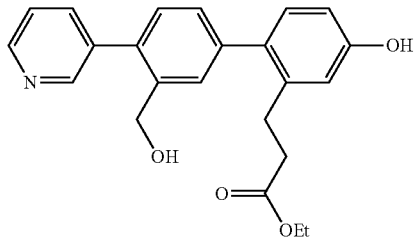 [SMILES: CCOC(=O)CCc1cc(O)ccc1-c1ccc(-c2cccnc2)c(CO)c1]

Yield 74% (CH$_2$Cl$_2$/AcOEt 1:1). $^1$H NMR (300 MHz, CDCl$_3$) δ ppm: 8.56 (d, J=1.5 Hz, 1H), 8.45 (dd, J$_1$=4.9 Hz, J$_2$=1.5 Hz, 1H), 7.80 (td, J$_1$=7.9 Hz, J$_2$=1.7 Hz, J$_3$=1.7 Hz, 1H), 7.46 (s, 1H), 7.31 (dd, J$_1$=7.8 Hz, J$_2$=5.1 Hz, 1H), 7.23-7.14 (m, 2H), 6.93 (d, J=8.4 Hz, 1H), 6.74 (d, J=2.1 Hz, 1H), 6.67 (dd, J$_1$=8.4 Hz, J$_2$=2.4 Hz, 1H), 4.54 (s, 2H), 3.93 (q, J=7.2 Hz, 2H), 2.81 (t, J=7.8 Hz, 2H), 2.36 (t, J=7.8 Hz, 2H), 1.06 (t, J=7.2 Hz, 3H); $^{13}$C NMR (75 MHz, CDCl$_3$) b ppm: 173.3, 156.5, 148.8, 147.3, 141.8, 139.0, 138.1, 137.6, 136.7, 135.2, 132.6, 131.3, 130.1, 129.8, 128.8, 123.5, 115.9, 113.6, 62.4, 60.5, 35.3, 28.3, 14.0; HRMS (EI) m/z: calcd for C$_{23}$H$_{23}$NO$_4$: 378.1705 (M+1), found: 378.1700; white solid, mp: 46-48° C.

Example 28: ethyl 3-[2'-(fluoromethyl)-4"-hydroxy-3-(trifluoromethyl)-(1,1';4',1")terphenyl-2"-yl]propionate (14b)

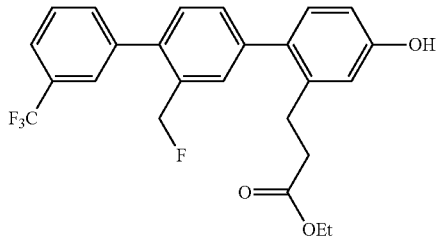 [SMILES: CCOC(=O)CCc1cc(O)ccc1-c1ccc(-c2cccc(C(F)(F)F)c2)c(CF)c1]

Yield 35% (hexane/AcOEt 10:1). $^1$H RMN (300 MHz, CDCl$_3$) δ ppm: 7.73-7.48 (m, 5H), 7.41-7.37 (m, 2H), 7.13 (d, J=8.2 Hz, 1H), 6.84 (d, J=2.4 Hz, 1H), 6.79 (dd, J$_1$=8.2 Hz, J$_2$=2.6 Hz, 1H), 5.29 (d, J=48.0 Hz, 2H), 4.11 (q, J=7.1 Hz, 2H), 2.96 (t, J=7.8 Hz, 2H), 2.51 (t, J=7.8 Hz, 2H), 1.21 (t, J=7.1 Hz, 3H); $^{19}$F RMN (282 MHz, CDCl$_3$) δ ppm: −63.04 (s, 3F), −199.0 (t, J=48.2 Hz, 1F); $^{13}$C RMN (75 MHz, CDCl$_3$) δ ppm: 173.4, 155.6, 141.5, 140.5, 139.3, 139.2, 133.2, 133.1 (d, $^2$J=15.6 Hz), 132.7, 131.5, 131.2 (d, $^3$J=6.3 Hz), 130.8 (q, $^2$J=32.4 Hz), 130.3, 130.0, 128.8, 126.0 (q, $^3$J=3.4 Hz), 124.3 (q, $^3$J=3.4 Hz), 124.0 (q, $^1$J=272.5 Hz), 115.8, 113.5, 82.6 (d, $^1$J=165.6 Hz), 60.7, 35.3, 28.3, 14.1.

Example 29: ethyl 3-[3'-(fluoromethyl)-4-hydroxy-4'-(pyridin-3-yl)biphenyl-2-yl]propionate (14c)

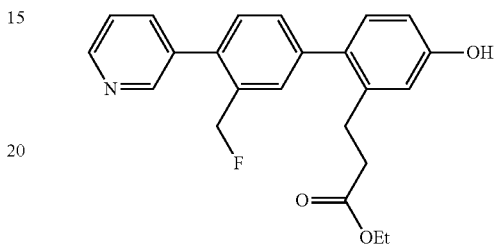

Yield 35% (CH$_2$Cl$_2$/AcOEt 5:1). $^1$H NMR (300 MHz, CDCl$_3$) δ ppm: 8.72 (d, J=1.6 Hz, 1H), 8.68 (dd, J$_1$=4.9 Hz, J$_2$=1.6 Hz, 1H), 7.87 (ddd, J$_1$=7.8 Hz, J$_2$=2.1 Hz, J$_3$=1.8 Hz, 1H), 7.51 (t, J=1.6 Hz, 1H), 7.50-7.36 (m, 3H), 7.11 (d, J=8.2 Hz, 1H), 6.86 (d, J=2.4 Hz, 1H), 6.81 (dd, J$_1$=8.2 Hz, J$_2$=2.6 Hz, 1H), 5.29 (d, J=48.0 Hz, 2H), 4.07 (q, J=7.1 Hz, 2H), 2.94 (t, J=8.0 Hz, 2H), 2.48 (t, J=8.0 Hz, 2H), 1.19 (t, J=7.1 Hz, 3H); $^{19}$F RMN (282 MHz, CDCl$_3$) δ ppm: −197.7 (t, J=48.0 Hz, 1F); $^{13}$C NMR (75 MHz, CDCl$_3$) δ ppm: 172.9, 156.4, 149.2, 148.1, 142.0, 139.4, 137.4, 136.6, 136.0, 133.3 (d, $^2$J=15.9 Hz), 132.5, 131.6 (d, $^3$J=6.1 Hz), 131.4, 130.5, 130.2, 123.5, 116.0, 113.6, 82.6 (d, $^1$J=166.1 Hz), 60.5, 35.3, 28.3, 14.1.

Example 30: 3-[2'-(fluoromethyl)-4"-hydroxy-3-methyl-(1,1';4',1")terphenyl-2"-yl]propionic acid (15a)

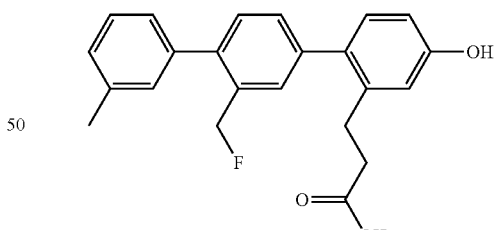

Yield 99%. $^1$H RMN (300 MHz, CDCl$_3$) δ ppm: 7.37 (s, 1H), 7.31-7.09 (m, 6H), 7.05 (d, J=8.4 Hz, 1H), 6.73 (d, J=2.4 Hz, 1H), 6.68 (dd, J$_1$=8.3 Hz, J$_2$=2.3 Hz, 1H), 5.24 (d, J=47.7 Hz, 2H), 2.86 (t, J=7.7 Hz, 2H), 2.44 (t, J=7.7 Hz, 2H), 2.34 (s, 3H); $^{19}$F RMN (282 MHz, CDCl$_3$) δ ppm: −200.7 (t, J=47.9 Hz, 1F); $^{13}$C RMN (75 MHz, CDCl$_3$) δ ppm: 178.5, 155.1, 140.7, 140.4, 139.6, 139.1, 137.9, 133.8, 133.2 (d, $^2$J=15.3 Hz), 131.7, 130.5 (d, $^3$J=6.6 Hz), 130.0 (2×), 129.8, 128.2 (2×), 126.4, 115.7, 113.5, 82.8 (d, $^1$J=163.9 Hz), 34.9, 28.0, 21.5; HRMS (EI) m/z: calcd for C$_{23}$H$_{21}$FO$_3$: 364.1475, found: 364.1471.

Example 31: 3-[2'-(fluoromethyl)-4"-hydroxy-3-(trifluoromethyl)-(1,1';4',1")terphenyl-2"-yl]propionic acid (15b)

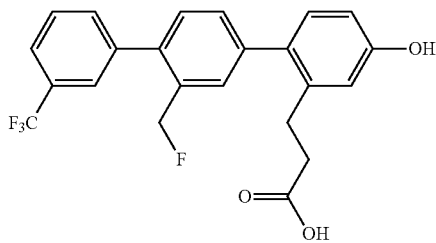 [SMILES: O=C(O)CCc1cc(O)ccc1-c1ccc(-c2cccc(C(F)(F)F)c2)c(CF)c1]

Yield 99%. $^1$H RMN (300 MHz, CDCl$_3$) δ ppm: 7.72-7.53 (m, 5H), 7.48 (d, J=0.9 Hz, 1H), 7.36 (d, J=0.9 Hz, 2H), 7.12 (d, J=8.2 Hz, 1H), 6.84 (d, J=2.3 Hz, 1H), 6.78 (dd, J$_1$=8.2 Hz, J$_2$=2.4 Hz, 1H), 5.28 (d, J=47.9 Hz, 2H), 2.94 (t, J=7.6 Hz, 2H), 2.53 (t, J=7.6 Hz, 2H); $^{19}$F RMN (282 MHz, CDCl$_3$) δ ppm: −63.04 (s, 3F), −199.0 (t, J=47.9 Hz, 1F); $^{13}$C RMN (75 MHz, CDCl$_3$) δ ppm: 178.7, 155.4, 141.3, 140.5, 139.3, 139.0, 133.3, 133.1 (d, $^2$J=15.9 Hz), 132.7, 131.6, 131.1 (d, $^3$J=6.1 Hz), 130.8 (q, $^2$J=32.4 Hz), 130.2, 130.0, 128.8, 126.0 (q, $^3$J=3.1 Hz), 124.3 (q, $^3$J=3.1 Hz), 124.0 (q, $^1$J=272.5 Hz), 115.7, 113.6, 82.6 (d, $^1$J=165.6 Hz), 34.9, 27.9.

Example 32: 3-[3'-(fluoromethyl)-4-hydroxy-4'-(pyridin-3-yl)biphenyl-2-yl]propionic acid (15c)

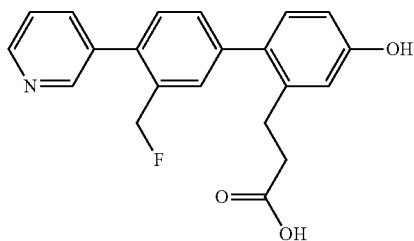 [SMILES: O=C(O)CCc1cc(O)ccc1-c1ccc(-c2cccnc2)c(CF)c1]

Yield 99%. $^1$H NMR (300 MHz, CDCl$_3$+drops MeOD) δ ppm: 8.55 (s, 1H), 8.51 (d, J=3.4 Hz, 1H), 7.87 (dt, J$_1$=7.8 Hz, J$_2$=1.8 Hz, 1H), 7.41 (t, J=1.5 Hz, 1H), 7.40-7.27 (m, 3H), 7.00 (d, J=8.2 Hz, 1H), 6.73 (d, J=2.4 Hz, 1H), 6.68 (dd, J$_1$=8.2 Hz, J$_2$=2.5 Hz, 1H), 5.18 (d, J=48.1 Hz, 2H), 2.83 (t, J=8.0 Hz, 2H), 2.39 (t, J=8.0 Hz, 2H); $^{19}$F RMN (282 MHz, CDCl$_3$+drops MeOD) δ ppm: −197.4 (t, J=48.1 Hz, 1F); $^{13}$C NMR (75 MHz, CDCl$_3$+drops MeOD) δ ppm: 175.4, 156.4, 148.8, 147.7, 142.0, 139.1, 137.4, 136.3, 136.0, 133.1 (d, $^2$J=15.7 Hz), 132.0, 131.4 (d, $^3$J=5.9 Hz), 131.1, 130.4, 129.9, 123.4, 115.5, 113.3, 82.4 (d, $^1$J=165.5 Hz), 35.0, 28.1; white solid, mp: 200-202° C.

Example 33: 2-(difluoromethyl)-3'-methylbiphenyl-4-ol (16a)

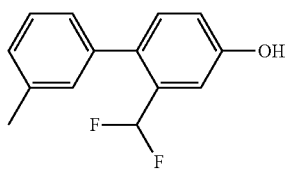 [SMILES: Cc1cccc(-c2ccc(O)cc2C(F)F)c1]

Yield 79% (hexane/AcOEt 10:1). $^1$H NMR (300 MHz, CDCl$_3$) δ ppm: 7.23 (t, J=7.5 Hz, 1H), 7.13 (t, J=8.1 Hz, 3H), 7.03 (d, J=8.4 Hz, 2H), 6.91 (dt, J$_1$=8.1 Hz, J$_2$=1.4 Hz, 1H), 6.42 (t, J=54.9 Hz, 1H), 2.33 (s, 3H); $^{19}$F NMR (282 MHz, CDCl$_3$) δ ppm: −108.38 (d, J=54.7 Hz, 2F); $^{13}$C NMR (75 MHz, CDCl$_3$) δ ppm: 155.1, 138.3, 138.1, 134.3 (t, $^3$J=6.7 Hz), 133.0 (t, $^2$J=21.8 Hz), 131.7, 130.3, 128.3, 128.2, 126.6, 117.6 (t, $^4$J=1.9 Hz), 112.9 (t, $^1$J=234.9 Hz), 111.0 (t, $^3$J=5.3 Hz), 21.4; HRMS (EI) m/z: calcd for C$_{14}$H$_{12}$F$_{20}$: 234.0856, found: 234.0844; yellowish oil.

Example 34: 2-(difluoromethyl)-3'-(trifluoromethyl)biphenyl-4-ol (16b)

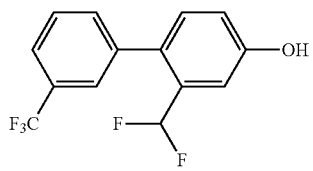

Yield 56% (hexane/AcOEt 10:1). $^1$H NMR (300 MHz, CDCl$_3$) δ ppm: 7.59 (d, J=7.7 Hz, 1H), 7.53 (br s, 1H), 7.48 (d, J=8.1 Hz, 1H), 7.45 (d, J=7.7 Hz, 1H), 7.19 (d, J=4.7 Hz, 1H), 7.16 (d, J=5.1 Hz, 1H), 6.96 (dt, J$_1$=8.4 Hz, J$_2$=1.3 Hz, 1H), 6.36 (t, J=54.8 Hz, 1H), 5.23 (s, 1H); $^{19}$F NMR (282 MHz, CDCl$_3$) δ ppm: −63.19 (s, 3F), −108.56 (d, J=54.8 Hz, 2F); 13C NMR (75 MHz, CDCl$_3$) δ ppm: 155.7, 139.2, 133.2 (t, $^2$J=21.9 Hz), 132.9, 132.4 (t, $^3$J=6.4 Hz), 131.9, 131.0 (q, $^2$J=32.2 Hz), 128.9, 126.2 (q, $^3$J=3.8 Hz), 124.5 (q, $^3$J=3.7 Hz), 124.0 (q, $^1$J=270.7 Hz), 118.0, 112.6 (t, $^1$J=235.7 Hz), 112.4 (t, $^3$J=5.7 Hz); HRMS (EI) m/z: calcd for C$_{14}$H$_9$F$_5$O: 288.0574, found: 288.0548; yellowish oil.

Example 35: 2-(difluoromethyl)-3'-methylbiphenyl-4-yl trifluoromethanesulfonate (17a)

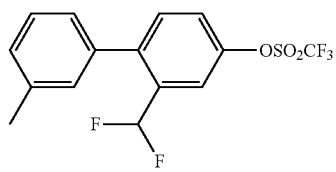

Yield 79% (hexane/AcOEt 10:1). $^1$H NMR (300 MHz, CDCl$_3$) δ ppm: 7.59 (br s, 1H), 7.36 (br s, 2H), 7.28 (t, J=7.5 Hz, 1H), 7.19 (d, J=7.5 Hz, 1H), 7.05 (d, J=8.4 Hz, 2H), 6.43 (t, J=51.2 Hz, 1H), 2.34 (s, 3H); $^{19}$F NMR (282 MHz, CDCl$_3$) δ ppm: −73.22 (s, 3F), −108.83 (d, J=51.2 Hz, 2F); 13C NMR (75 MHz, CDCl$_3$) δ ppm: 155.1, 138.3, 138.1, 134.3 (t, $^3$J=6.6 Hz), 133.0 (t, $^2$J=21.8 Hz), 131.7, 130.3, 128.3, 128.2, 126.7, 118.7 (q, $^1$J=318.9 Hz), 117.8 (t, $^4$J=1.9 Hz), 112.9 (t, $^1$J=234.9 Hz), 112.0 (t, $^3$J=5.3 Hz), 21.4; HRMS (EI) m/z: calcd for C$_{15}$H$_{11}$F$_5$O$_3$S: 366.0349, found: 366.0315.

Example 36: 2-(difluoromethyl)-3'-(trifluoromethyl)biphenyl-4-yl trifluoromethanesulfonate (17b)

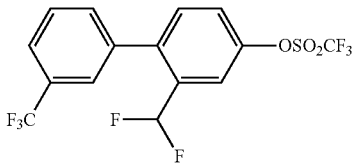

Yield 83% (hexane/AcOEt 10:1). $^1$H NMR (300 MHz, CDCl$_3$) δ ppm: 7.66 (d, J=7.8 Hz, 1H), 7.62 (br s, 1H), 7.55 (t, J=7.8 Hz, 2H), 7.47 (d, J=7.5 Hz, 1H), 7.39 (t, J=9.3 Hz, 2H), 6.36 (t, J=54.3 Hz, 1H); $^{19}$F NMR (282 MHz, CDCl$_3$) δ ppm: −63.29 (s, 3F), −73.18 (s, 3F), −109.22 (d, J=54.1 Hz, 2F); $^{13}$C NMR (75 MHz, CDCl$_3$) δ ppm: 149.3, 140.0 (t, $^3$J=6.1 Hz), 137.6, 134.3 (t, $^2$J=22.6 Hz), 132.6 (t, $^4$J=1.2 Hz), 132.5, 131.4 (q, $^2$J=32.5 Hz), 129.3, 126.1, 126.0 (q, $^3$J=3.8 Hz), 125.5 (q, $^3$J=3.7 Hz), 123.7 (q, $^1$J=270.7 Hz), 119.2 (t, $^3$J=6.0 Hz), 118.8 (q, $^1$J=318.8 Hz), 111.6 (t, $^1$J=237.4 Hz); HRMS (EI) m/z: calcd for C$_{15}$H$_8$F$_8$O$_3$S: 420.0066, found: 420.0030.

Example 37: ethyl (E)-3-[4''-(benzyloxy)-2'-(difluoromethyl)-3-methyl-(1,1';4',1'')terphenyl-2''-yl]acrylate (18a)

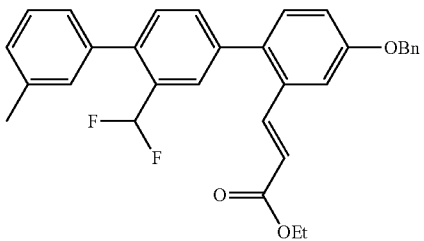 [SMILES: CCOC(=O)/C=C/c1cc(OCc2ccccc2)ccc1-c1ccc(-c2cccc(C)c2)c(C(F)F)c1]

Yield 67% (hexane/AcOEt 20:1). $^1$H RMN (300 MHz, CDCl$_3$) δ ppm: 7.66 (d, J=15.9 Hz, 2H), 7.43-7.19 (m, 10H), 7.19-7.08 (m, 3H), 7.01 (dd, J$_1$=8.3 Hz, J$_2$=2.3 Hz, 1H), 6.51 (t, J=54.9 Hz, 1H), 6.32 (d, J=15.9 Hz, 1H), 5.06 (s, 2H), 4.13 (q, J=7.1 Hz, 2H), 2.34 (s, 3H), 1.20 (t, J=7.2 Hz, 3H); $^{19}$F RMN (282 MHz, CDCl$_3$) δ ppm: −107.9 (d, J=54.7 Hz, 2F); $^{13}$C RMN (75 MHz, CDCl$_3$) b ppm: 166.6, 158.4, 143.2, 140.3, 139.1, 138.2, 136.5, 134.6, 133.8, 131.9, 131.7 (t, $^2$J=22.1 Hz), 131.7, 130.2, 130.1, 128.7 (2×), 128.3, 128.1, 127.5 (2×), 126.9 (t, $^3$J=4.8 Hz), 126.5, 119.9, 117.0, 113.0 (t, $^1$J=234.7 Hz), 112.5, 70.2, 60.5, 21.4, 14.2; HRMS (EI) m/z: calcd for C$_{32}$H$_{28}$F$_2$O$_3$: 498.2007, found: 498.1991; white solid, mp: 124-126° C.

Example 38: ethyl (E)-3-[4''-(benzyloxy)-2'-(difluoromethyl)-3-(trifluoromethyl)-(1,1';4',1'')terphenyl-2''-yl]acrylate (18b)

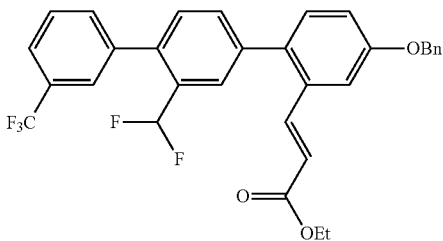 [SMILES: CCOC(=O)/C=C/c1cc(OCc2ccccc2)ccc1-c1ccc(-c2cccc(C(F)(F)F)c2)c(C(F)F)c1]

Yield 70% (hexane/AcOEt 20:1). $^1$H RMN (300 MHz, CDCl$_3$) δ ppm: 7.65 (d, J=13.2 Hz, 4H), 7.59-7.50 (m, 2H), 7.44-7.23 (m, 8H), 7.19 (d, J=2.4 Hz, 1H), 7.04 (dd, J$_1$=8.4 Hz, J$_2$=2.4 Hz, 1H), 6.45 (t, J=54.8 Hz, 1H), 6.34 (d, J=15.6 Hz, 1H), 5.09 (s, 2H), 4.16 (q, J=7.1 Hz, 2H), 1.23 (t, J=7.1 Hz, 3H); $^{19}$F RMN (282 MHz, CDCl$_3$) δ ppm: −63.16 (s, 3F), −108.1 (d, J=54.7 Hz, 2F); $^{13}$C RMN (75 MHz, CDCl$_3$) δ ppm: 166.6, 158.6, 143.0, 140.1, 139.1, 138.5 (t, $^3$J=5.5 Hz), 136.5, 134.3, 133.8, 132.8, 132.2, 131.8 (t, $^2$J=22.3 Hz), 131.7, 131.0 (q, $^2$J=32.6 Hz), 130.2, 129.0, 128.7 (2×), 128.2, 127.5 (2×), 127.2 (t, $^3$J=5.2 Hz), 126.2 (q, $^3$J=3.8 Hz), 124.8 (q, $^3$J=3.8 Hz), 123.9 (q, $^1$J=272.4 Hz), 120.1, 117.0, 112.8 (t, $^1$J=237.2 Hz), 112.6, 70.3, 60.5, 14.2; HRMS (EI) m/z: calcd for C$_{32}$H$_{25}$F$_5$O$_3$: 552.1724, found: 552.1725.

Example 39: (E)-ethyl 3-[4-(benzyloxy)-3'-(difluoromethyl)-4'-(pyridin-3-yl)biphenyl-2-yl]acrylate (18c)

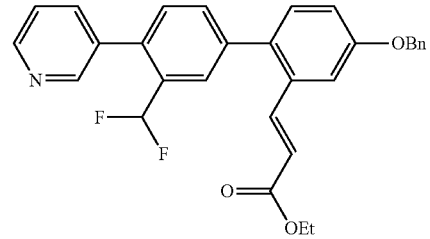 [SMILES: CCOC(=O)/C=C/c1cc(OCc2ccccc2)ccc1-c1ccc(-c2cccnc2)c(C(F)F)c1]

Yield 55% (CH$_2$Cl$_2$/AcOEt 10:1). $^1$H RMN (300 MHz, CDCl$_3$) δ ppm: 8.70 (dd, J=4.7 Hz, 1.6 Hz, 2H), 7.77 (ddd, J$_1$=7.8 Hz, J$_2$=2.1 Hz, J$_3$=1.8 Hz, 2H), 7.72 (d, J=15.9 Hz, 1H), 7.51-7.34 (m, 9H), 7.32 (d, J=2.6 Hz, 1H), 7.11 (dd, J$_1$=8.5 Hz, J$_2$=2.6 Hz, 1H), 6.54 (t, J=54.7 Hz, 1H), 6.42 (d, J=15.9 Hz, 1H), 5.16 (s, 2H), 4.22 (q, J=7.1 Hz, 2H), 1.30 (t, J=7.1 Hz, 3H); $^{19}$F RMN (282 MHz, CDCl$_3$) δ ppm: −107.99 (d, J=54.7 Hz, 2F); $^{13}$C RMN (75 MHz, CDCl$_3$) δ ppm: 166.6, 158.6, 149.8, 149.2, 143.0, 140.2, 139.2, 136.8, 136.5, 136.3 (t, $^3$J=5.7 Hz), 134.2, 133.8, 132.2, 132.1 (t, $^2$J=21.9 Hz), 131.7, 130.4, 128.7, 128.2, 127.5, 127.3 (t, $^3$J=5.6 Hz), 123.2, 120.2, 117.0, 114.0, 112.8 (t, $^1$J=237.5 Hz), 112.6, 70.2, 60.5, 14.2; HRMS (EI) m/z: calcd for C$_{30}$H$_{25}$F$_2$NO$_3$: found: yellowish solid, mp: 93-95° C.

Example 40: ethyl 3-[2'-(difluoromethyl)-4''-hydroxy-3-methyl-(1,1';4',1'')terphenyl-2''-yl]propionate (19a)

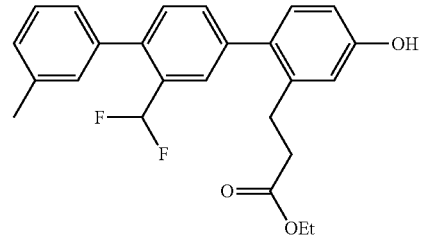 [SMILES: Cc1cccc(-c2ccc(-c3ccc(O)cc3CCC(=O)O)cc2C(F)F)c1]

Yield 98%. $^1$H RMN (300 MHz, CDCl$_3$) δ ppm: 7.61 (s, 1H), 7.34 (d, J=8.1 Hz, 1H), 7.25 (t, J=7.4 Hz, 2H), 7.20-7.08 (m, 3H), 7.05 (d, J=8.4 Hz, 1H), 6.75 (d, J=1.8 Hz, 1H), 6.70 (dd, J$_1$=7.7 Hz, J$_2$=2.0 Hz, 1H), 6.51 (t, J=54.9 Hz, 1H), 6.10 (s, 1H), 4.01 (q, J=7.3 Hz, 2H), 2.84 (t, J=7.8 Hz, 2H), 2.42 (t, J=7.8 Hz, 2H), 2.34 (s, 3H), 1.12 (t, J=7.1 Hz, 3H); $^{19}$F RMN (282 MHz, CDCl$_3$) δ ppm: −107.8 (d, J=54.7 Hz, 2F); $^{13}$C RMN (75 MHz, CDCl$_3$) δ ppm: 173.4, 155.6, 140.8, 139.9 (t, $^3$J=6.2 Hz), 139.4, 138.3, 138.1, 133.2, 131.6, 131.5 (t, $^2$J=21.7 Hz), 131.4, 130.2, 130.1, 128.6, 128.3, 126.5, 126.4 (t, $^2$J=5.0 Hz), 115.8, 113.5 (t, $^1$J=234.6 Hz), 113.1, 60.7, 35.3, 28.3, 21.4, 14.0; HRMS (EI) m/z: calcd for C$_{25}$H$_{24}$F$_2$O$_3$: 410.1694, found: 410.1706.

Example 41: ethyl 3-[2'-(difluoromethyl)-4''-hydroxy-3-(trifluoromethyl)-(1,1';4',1'')terphenyl-2''-yl]propionate (19b)

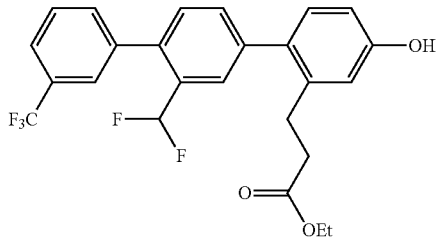

Yield 97%. H RMN (300 MHz, CDCl$_3$) δ ppm: 7.62 (d, J=5.6 Hz, 3H), 7.52 (d, J=4.4 Hz, 2H), 7.34 (dd, J$_1$=30.1 Hz, J$_2$=7.9 Hz, 2H), 7.04 (d, J=8.1 Hz, 1H), 6.75 (d, J=1.8 Hz, 1H), 6.71 (dd, J$_1$=8.3 Hz, J$_2$=1.8 Hz, 1H), 6.43 (t, J=54.9 Hz, 1H), 4.01 (q, J=7.1 Hz, 2H), 2.86 (t, J=7.7 Hz, 2H), 2.42 (t, J=7.7 Hz, 2H), 1.12 (t, J=7.1 Hz, 3H); $^{19}$F RMN (282 MHz, CDCl$_3$) δ ppm: −63.1 (s, 3F), −107.9 (d, J=54.8 Hz, 2F); $^{13}$C RMN (75 MHz, CDCl$_3$) δ ppm: 173.4, 155.8, 141.7, 139.3, 139.2, 138.1 (t, $^3$J=6.0 Hz), 132.8, 131.7, 131.6 (t, $^2$J=22.0 Hz), 131.5, 131.0 (q, $^2$J=32.4 Hz), 130.2, 128.9, 126.8 (t, $^3$J=5.1 Hz), 126.2 (q, $^3$J=3.8 Hz), 124.7 (q, $^3$J=3.8 Hz), 123.9 (q, $^1$J=272.6 Hz), 115.8, 113.6, 112.9 (t, $^1$J=236.9 Hz), 60.8, 35.3, 28.3, 14.0; HRMS (EI) m/z: calcd for C$_{25}$H$_{21}$F$_5$O$_3$: 464.1411, found: 464.1424.

Example 42: ethyl 3-[3'-(difluoromethyl)-4-hydroxy-4'-(pyridin-3-yl)biphenyl-2-yl]propionate (19c)

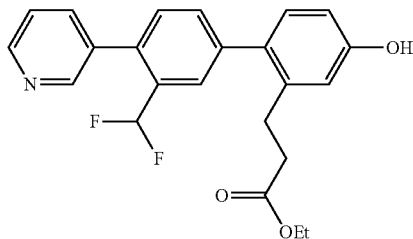

Yield 65% (CH$_2$Cl$_2$/AcOEt 4:1). $^1$H RMN (300 MHz, CDCl$_3$) δ ppm: 8.70 (dd, J$_1$=4.9 Hz, J$_2$=1.6 Hz, 2H), 7.83 (ddd, J$_1$=7.8 Hz, J$_2$=2.1 Hz, J$_3$=1.8 Hz, 2H), 7.72 (br s, 1H), 7.53-7.45 (m, 2H), 7.37 (d, J=7.9 Hz, 1H), 7.12 (d, J=8.2 Hz, 1H), 6.87 (d, J=2.5 Hz, 1H), 6.82 (dd, J$_1$=8.2 Hz, J$_2$=2.6 Hz, 1H), 6.53 (t, J=54.8 Hz, 1H), 4.07 (q, J=7.1 Hz, 2H), 2.93 (t, J=7.8 Hz, 2H), 2.49 (t, J=7.8 Hz, 2H), 1.19 (t, J=7.1 Hz, 3H); $^{19}$F RMN (282 MHz, CDCl$_3$) δ ppm: −107.7 (d, J=54.8 Hz, 2F); $^{13}$C RMN (75 MHz, CDCl$_3$) δ ppm: 172.9, 156.6, 149.2, 148.5, 142.2, 139.4, 137.5, 135.3 (t, $^3$J=5.7 Hz), 134.9, 132.2, 131.9 (t, $^2$J=23.1 Hz), 131.5, 130.4, 127.1 (t, $^3$J=5.4 Hz), 123.5, 116.0, 113.7, 113.0 (t, $^1$J=236.1 Hz), 60.5, 35.3, 28.2, 14.1.

Example 43: 3-[2'-(difluoromethyl)-4''-hydroxy-3-methyl-(1,1';4',1'')terphenyl-2''-yl]propionic acid (20a)

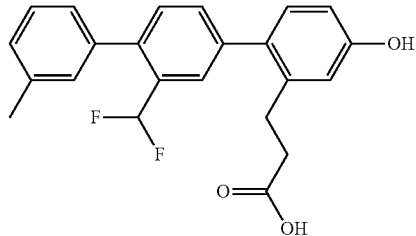

Yield 99%. $^1$H RMN (300 MHz, CDCl$_3$) δ ppm: 7.60 (s, 1H), 7.32 (t, J=8.1 Hz, 2H), 7.26 (d, J=7.2 Hz, 1H), 7.20-7.08 (m, 3H), 7.06 (d, J=8.1 Hz, 1H), 6.74 (s, 1H), 6.70 (d, J=8.1 Hz, 1H), 6.51 (t, J=54.9 Hz, 1H), 2.86 (t, J=7.5 Hz, 2H), 2.45 (t, J=7.7 Hz, 2H), 2.34 (s, 3H); $^{19}$F RMN (282 MHz, CDCl$_3$) δ ppm: −107.81 (d, J=55.0 Hz, 2F); $^{13}$C RMN (75 MHz, CDCl$_3$) δ ppm: 178.4, 155.3, 140.7, 140.0 (t, $^3$J=6.2 Hz), 139.1, 138.3, 138.2, 133.4, 131.7, 131.6 (t, $^2$J=21.6 Hz), 131.4, 130.2, 130.1, 128.6, 128.3, 126.6, 126.4 (t, $^2$J=4.9 Hz), 115.7, 113.6, 113.1 (t, $^1$J=234.6 Hz), 34.9, 27.9, 21.4; HRMS (EI) m/z: calcd for C$_{23}$H$_{20}$F$_2$O$_3$: 382.1381, found: 382.1377; white solid, mp: 40-42° C.

Example 44: 3-[2'-(difluoromethyl)-4''-hydroxy-3-(trifluoromethyl)-(1,1';4',1'')terphenyl-2''-yl]propionic acid (20b)

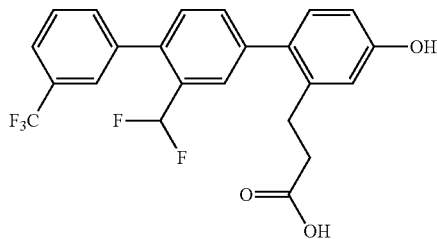 [SMILES: O=C(O)CCc1cc(O)ccc1-c1ccc(-c2cccc(C(F)(F)F)c2)c(C(F)F)c1]

Yield 98%. $^1$H RMN (300 MHz, CDCl$_3$) δ ppm: 7.76-7.57 (m, 5H), 7.41 (dd, J$_1$=27.2 Hz, J$_2$=7.9 Hz, 2H), 7.13 (d, J=8.2 Hz, 1H), 6.84 (d, J=2.5 Hz, 1H), 6.79 (dd, J$_1$=8.2 Hz, J$_2$=2.6 Hz, 1H), 6.51 (t, J=54.8 Hz, 1H), 2.94 (t, J=7.6 Hz, 2H), 2.54 (t, J=7.6 Hz, 2H); $^{19}$F RMN (282 MHz, CDCl$_3$) δ ppm: −63.1 (s, 3F), −108.0 (d, J=54.8 Hz, 2F); $^{13}$C RMN (75 MHz, CDCl$_3$) δ ppm: 178.5, 155.5, 141.6, 139.2, 139.1, 138.2 (t, $^3$J=6.2 Hz), 133.1, 132.8, 131.6 (t, $^2$J=22.0 Hz), 131.6, 131.0 (q, $^2$J=32.5 Hz), 130.3, 128.9, 126.8 (t, $^3$J=5.3 Hz), 126.2 (q, $^3$J=3.3 Hz), 124.7 (q, $^3$J=3.3 Hz), 123.9 (q, $^1$J=272.3 Hz), 115.8, 113.7, 112.9 (t, $^1$J=237.0 Hz), 34.8, 27.9; HRMS (EI) m/z: calcd for C$_{23}$H$_{17}$F$_5$O$_3$: 435.1020 (M−1), found: 435.1029; white solid, mp: 131-133° C.

Example 45: 3-[3'-(difluoromethyl)-4-hydroxy-4'-(pyridin-3-yl)biphenyl-2-yl]propionic acid (20c)

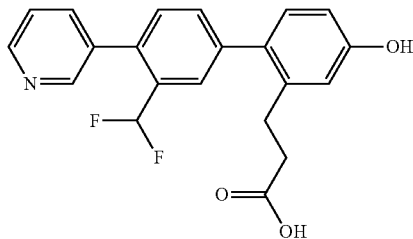 [SMILES: O=C(O)CCc1cc(O)ccc1-c1ccc(-c2cccnc2)c(C(F)F)c1]

Yield 97%. $^1$H RMN (300 MHz, MeOD) δ ppm: 8.60 (dd, $J_1$=4.7 Hz, $J_2$=1.3 Hz, 1H), 7.90 (ddd, $J_1$=8.1 Hz, $J_2$=2.1 Hz, $J_3$=1.8 Hz, 2H), 7.65 (br s, 1H), 7.58-7.50 (m, 2H), 7.43 (d, J=7.8 Hz, 1H), 7.06 (d, J=8.3 Hz, 1H), 6.81 (d, J=2.4 Hz, 1H), 6.73 (dd, $J_1$=8.3, $J_2$=2.6 Hz, 1H), 6.66 (t, J=54.8 Hz, 1H), 2.87 (t, J=8.0 Hz, 2H), 2.44 (t, J=7.8 Hz, 2H); $^{19}$F RMN (282 MHz, MeOD) δ ppm: −107.9 (d, J=54.8 Hz, 2F); $^{13}$C RMN (75 MHz, MeOD) δ ppm: 176.5, 158.6, 150.2, 149.5, 143.9, 140.7, 139.1, 136.9 (t, $^3J$=5.0 Hz), 133.4 (t, $^2J$=21.7 Hz), 133.2, 133.1, 132.3, 132.0, 128.3 (t, $^3J$=6.1 Hz), 125.0, 116.8, 115.1 (t, $^1J$=236.5 Hz), 114.6, 36.2, 29.5; white solid, mp: 211-213° C.

Example 46: ethyl 3-[4"-methoxy-3,2'-dimethyl-(1,1';4',1")terphenyl-2"-yl]propionate (21b)

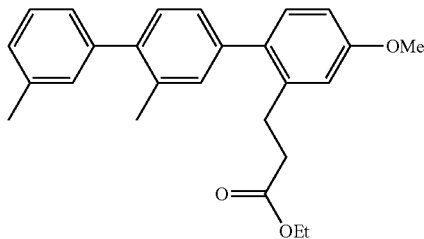

Yield 75% (hexane/AcOEt 10:1). $^1$H NMR (300 MHz, CDCl$_3$) δ ppm: 7.25 (t, J=7.5 Hz, 1H), 7.20-7.04 (m, 7H), 6.78 (d, J=2.7 Hz, 1H), 6.74 (dd, $J_1$=8.1 Hz, $J_2$=2.7 Hz, 1H), 4.02 (q, J=7.1 Hz, 2H), 3.78 (s, 3H), 2.91 (t, J=8.0 Hz, 2H), 2.42 (t, J=8.0 Hz, 2H), 2.34 (s, 3H), 2.24 (s, 3H), 1.14 (t, J=7.2 Hz, 3H); $^{13}$C RMN (75 MHz, CDCl$_3$) δ ppm: 172.9, 158.9, 141.6, 140.4, 140.0, 139.4, 137.6, 135.0, 134.4, 131.3, 131.3, 130.0, 129.6, 127.9, 127.5, 126.7, 126.3, 114.5, 111.5, 60.4, 55.3, 35.5, 28.6, 21.5, 20.6, 14.2; HRMS (EI) m/z: calcd for C$_{26}$H$_{28}$O$_3$: 388.2038, found: 388.2042.

Example 47: ethyl 3-[2'-(fluoromethyl)-4"-methoxy-3-methyl-(1,1';4',1")terphenyl-2"-yl]propionate (21c)

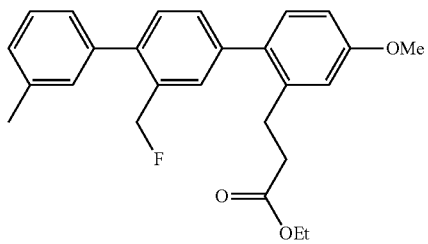 [SMILES: CCOC(=O)CCc1cc(OC)ccc1-c1ccc(-c2cccc(C)c2)c(CF)c1]

Yield 70% (hexane/AcOEt 20:1). $^1$H NMR (300 MHz, CDCl$_3$) δ ppm: 7.40 (s, 1H), 7.31-7.23 (m, 3H), 7.15 (s, 2H), 7.11 (d, J=8.2 Hz, 2H), 6.79 (d, J=2.6 Hz, 1H), 6.75 (dd, $J_1$=8.3 Hz, $J_2$=2.6 Hz, 1H), 5.25 (d, J=48.0 Hz, 2H), 4.00 (q, J=7.1 Hz, 2H), 3.76 (s, 3H), 2.89 (t, J=8.0 Hz, 2H), 2.41 (t, J=8.0 Hz, 2H), 2.34 (s, 3H), 1.13 (t, J=7.1 Hz, 3H); $^{19}$F NMR (282 MHz, CDCl$_3$) δ ppm: −201.04 (t, J=48.0 Hz, 1F); $^{13}$C NMR (75 MHz, CDCl$_3$) δ ppm: 172.8, 159.1, 140.6 (d, $^3J$=4.5 Hz), 140.5, 139.7, 139.4, 137.9, 133.7, 133.2 (d, $^2J$=15.9 Hz), 131.3, 130.5, 130.4, 130.0, 129.9, 129.8, 128.1 (d, $^3J$=3.4 Hz), 126.3, 114.5, 111.6, 82.8 (d, $^1J$=164.1), 60.4, 55.3, 35.4, 28.5, 21.5, 14.1; HRMS (EI) m/z: calcd for C$_{26}$H$_{27}$FO$_3$: 406.1944, found: 406.1921.

Example 48: ethyl 3-[2'-(difluoromethyl)-4"-methoxy-3-methyl-(1,1';4',1")terphenyl-2"-yl]propionate (21 d)

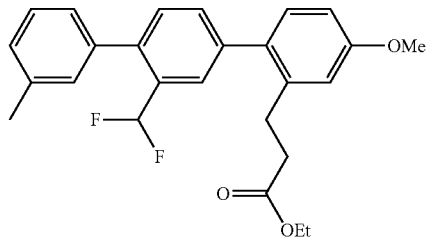 [SMILES: CCOC(=O)CCc1cc(OC)ccc1-c1ccc(-c2cccc(C)c2)c(C(F)F)c1]

Yield 68% (hexane/AcOEt 20:1). $^1$H NMR (300 MHz, CDCl$_3$) δ ppm: 7.62 (s, 1H), 7.36 (d, J=8.0 Hz, 1H), 7.31 (s, 1H), 7.27 (d, J=7.4 Hz, 1H), 7.15 (t, J=8.7 Hz, 3H), 7.12 (d, J=8.3 Hz, 1H), 6.80 (d, J=2.6 Hz, 1H), 6.77 (dd, $J_1$=8.3 Hz, $J_2$=2.6 Hz, 1H), 6.52 (t, J=54.9 Hz, 1H), 4.01 (q, J=7.1 Hz, 2H), 3.78 (s, 3H), 2.89 (t, J=7.9 Hz, 2H), 2.43 (t, J=7.9 Hz, 2H), 2.36 (s, 3H), 1.13 (t, J=7.1 Hz, 3H); $^{19}$F NMR (282 MHz, CDCl$_3$) δ ppm: −107.87 (d, J=55.0 Hz, 2F); $^{13}$C NMR (75 MHz, CDCl$_3$) δ ppm: 172.7, 159.3, 140.8, 139.9 (t, $^3J$=6.6 Hz), 139.4, 138.3, 138.1, 133.3, 131.5 (t, $^2J$=21.5 Hz), 131.3, 130.2, 130.1, 128.6, 128.3, 126.6, 126.4 (t, $^3J$=5.0 Hz), 114.6, 113.1 (t, $^1J$=234.6 Hz), 111.7, 60.4, 55.3, 35.4, 28.4, 21.4, 14.1; HRMS (EI) m/z: calcd for C$_{26}$H$_{26}$F$_2$O$_3$: 424.1850, found: 424.1820.

Example 49: ethyl 3-[2'-(hydroxymethyl)-4"-methoxy-3-(trifluoromethyl)-(1,1';4',1")terphenyl-2"-yl]propionate (21e)

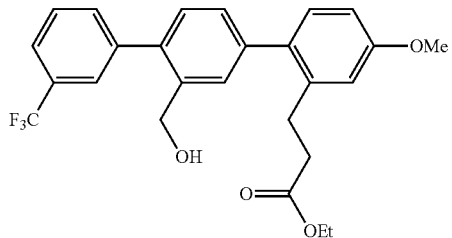 [SMILES: CCOC(=O)CCc1cc(OC)ccc1-c1ccc(-c2cccc(C(F)(F)F)c2)c(CO)c1]

Yield 76% (hexane/AcOEt 10:1). $^1$H NMR (300 MHz, CDCl$_3$) δ ppm: 7.73 (s, 1H), 7.65 (t, J=6.5 Hz, 2H), 7.56 (d, J=7.4 Hz, 1H), 7.53 (s, 1H), 7.29 (d, J=1.8 Hz, 2H), 7.20 (d, J=8.2 Hz, 1H), 6.86 (d, J=2.6 Hz, 1H), 6.83 (dd, $J_1$=8.2 Hz, $J_2$=2.6 Hz, 1H), 4.61 (s, 2H), 4.08 (q, J=7.1 Hz, 2H), 3.84

(s, 3H), 2.97 (t, J=8.0 Hz, 2H), 2.52 (t, J=8.0 Hz, 2H), 1.21 (t, J=7.1 Hz, 3H); $^{19}$F NMR (282 MHz, CDCl$_3$) δ ppm: −63.02 (s, 3F); $^{13}$C NMR (75 MHz, CDCl$_3$) δ ppm: 173.1, 159.1, 141.2, 141.1, 139.3, 138.2, 137.9, 133.8, 132.6, 131.2, 130.6 (q, $^2$J=32.0 Hz), 129.9, 129.7, 128.7, 128.6, 126.0 (q, $^3$J=3.7 Hz), 124.1 (q, $^1$J=270.7 Hz), 124.0 (q, $^3$J=3.7 Hz), 114.6, 111.7, 62.9, 60.5, 55.2, 35.5, 28.6, 14.1; HRMS (EI) m/z: calcd for C$_{26}$H$_{25}$F$_3$O$_4$: 458.1705, found: 458.1685.

Example 50: ethyl 3-[2'-methyl-4"-methoxy-3-(trifluoromethyl)-(1,1';4',1")terphenyl-2"-yl]propionate (21f)

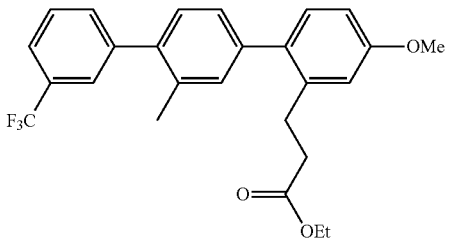

Yield 74% (hexane/AcOEt 20:1). $^1$H NMR (300 MHz, CDCl$_3$) δ ppm: 7.63–7.46 (m, 4H), 7.23–7.11 (m, 4H), 6.83 (d, J=2.5 Hz, 1H), 6.78 (dd, J$_1$=8.3 Hz, J$_2$=2.7 Hz, 1H), 4.05 (q, J=7.1 Hz, 2H), 3.80 (s, 3H), 2.94 (t, J=8.0 Hz, 2H), 2.46 (t, J=8.1 Hz, 2H), 2.26 (s, 3H), 1.17 (t, J=7.1 Hz, 3H); $^{19}$F NMR (282 MHz, CDCl$_3$) δ ppm: −63.01 (s, 3F); $^{13}$C NMR (75 MHz, CDCl$_3$) δ ppm: 172.8, 159.0, 142.4, 140.9, 139.3, 138.8, 135.0, 134.1, 132.6, 132.6, 131.5, 131.2, 130.5 (q, $^2$J=32.2 Hz), 129.5, 128.5, 127.0, 126.0 (q, $^3$J=3.7 Hz), 124.2 (q, $^1$J=270.8 Hz), 123.6 (q, $^3$J=3.7 Hz), 114.5, 111.6, 60.3, 55.2, 35.4, 28.5, 20.4, 14.1; HRMS (EI) m/z: calcd for C$_{26}$H$_{25}$F$_3$O$_3$: 465.1653 (M+Na), found: 465.1664.

Example 51: ethyl 3-[2'-(fluoromethyl)-4"-methoxy-3-(trifluoromethyl)-(1,1';4',1")terphenyl-2"-yl]propionate (21 g)

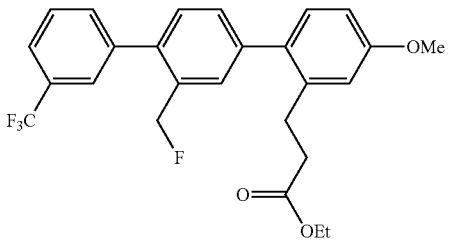 [SMILES: CCOC(=O)CCc1cc(OC)ccc1-c1ccc(-c2cccc(C(F)(F)F)c2)c(CF)c1]

Yield 71% (hexane/AcOEt 20:1). $^1$H NMR (300 MHz, CDCl$_3$) δ ppm: 7.62 (s, 1H), 7.57 (d, J=7.7 Hz, 2H), 7.51 (d, J=7.5 Hz, 1H), 7.43 (s, 1H), 7.31 (s, 2H), 7.11 (d, J=8.3 Hz, 1H), 6.80 (d, J=2.6 Hz, 1H), 6.76 (dd, J$_1$=8.3 Hz, J$_2$=2.6 Hz, 1H), 5.21 (d, J=48.0 Hz, 2H), 4.01 (q, J=7.1 Hz, 2H), 3.77 (s, 3H), 2.89 (t, J=7.9 Hz, 2H), 2.42 (t, J=7.9 Hz, 2H), 1.13 (t, J=7.1 Hz, 3H); $^{19}$F NMR (282 MHz, CDCl$_3$) δ ppm: −63.12 (s, 3H), −199.34 (t, J=48.0 Hz, 1F); $^{13}$C NMR (75 MHz, CDCl$_3$) δ ppm: 172.7, 159.3, 141.5, 140.6, 139.4, 139.2 (d, $^3$J=4.1 Hz), 133.4, 133.2 (d, $^2$J=15.8 Hz), 131.3, 131.2, 131.1, 130.7 (q, $^2$J=32.1 Hz), 130.3 (d, $^3$J=3.5 Hz), 130.0, 128.8, 126.1 (q, $^3$J=3.8 Hz), 124.3 (q, $^3$J=3.8 Hz), 124.1 (q, $^1$J=270.7 Hz), 114.6, 111.7, 82.6 (d, $^1$J=164.9 Hz), 60.4, 55.3, 35.4, 28.5, 14.1; HRMS (EI) m/z: calcd for C$_{26}$H$_{24}$F$_4$O$_3$: 460.1662, found: 460.1690.

Example 52: ethyl 3-[2'-(difluoromethyl)-4"-methoxy-3-(trifluoromethyl)-(1,1';4',1")terphenyl-2"-yl]propionate (21 h)

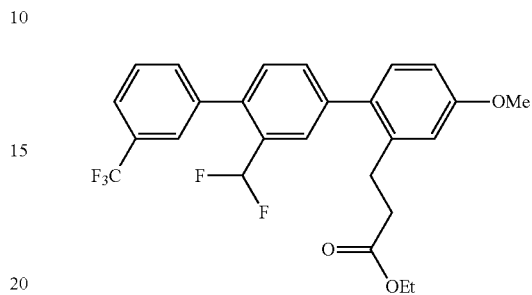

Yield 73% (hexane/AcOEt 20:1). $^1$H NMR (300 MHz, CDCl$_3$) δ ppm: 7.64 (s, 1H), 7.62 (d, J=2.4 Hz, 2H), 7.54 (t, J=2.4 Hz, 2H), 7.41 (d, J=7.8 Hz, 1H), 7.31 (d, J=7.8 Hz, 1H), 7.12 (d, J=8.1 Hz, 1H), 6.81 (d, J=2.6 Hz, 1H), 6.78 (dd, J$_1$=8.1 Hz, J$_2$=2.6 Hz, 1H), 6.44 (t, J=54.8 Hz, 1H), 4.01 (q, J=7.1 Hz, 2H), 3.78 (s, 3H), 2.88 (t, J=8.0 Hz, 2H), 2.43 (t, J=8.0 Hz, 2H), 1.13 (t, J=7.1 Hz, 3H); $^{19}$F NMR (282 MHz, CDCl$_3$) δ ppm: −63.16 (s, 3F), −108.04 (d, J=54.7 Hz, 2F); $^{13}$C NMR (75 MHz, CDCl$_3$) δ ppm: 172.7, 159.4, 141.8, 139.4, 139.3, 138.1 (t, $^3$J=6.3 Hz), 133.0, 132.8, 131.7, 131.6 (t, $^2$J=21.8 Hz), 131.3, 131.0 (q, $^2$J=32.2 Hz), 130.2, 128.9, 126.8 (t, $^3$J=5.4 Hz), 126.2 (q, $^3$J=3.8 Hz), 124.7 (q, $^3$J=3.8 Hz), 124.1 (q, $^1$J=270.8 Hz), 114.7, 112.9 (t, $^1$J=235.6 Hz), 111.8, 60.5, 55.3, 35.4, 28.4, 14.1; HRMS (EI) m/z: calcd for C$_{26}$H$_{23}$F$_5$O$_3$: 478.1567, found: 478.1513.

Example 53: ethyl 3-[3'-(hydroxymethyl)-4-methoxy-4'-(pyridin-3-yl)biphenyl-2-yl]propionate (21i)

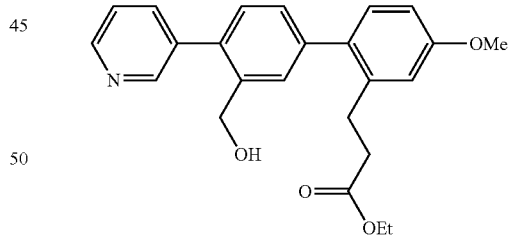

Terphenyl 28 (102 mg, 0.26 mmol) was dissolved in dry ethanol (10 mL) and the resulting solution cooled with an ice bath. Then, sodium borohydride (1.5 equiv) was slowly added and the reaction mixture was stirred for 30 min at room temperature. The reaction was hydrolyzed with water (1 mL), and ethanol was removed under reduced pressure. The aqueous layer was extracted with AcOEt, and the combined organic layers were dried over Na$_2$SO$_4$, filtered and removed in vacuo under reduced pressure. The crude reaction product was purified by means of chromatography on silica gel (CH$_2$Cl$_2$/AcOEt 1:1) to obtain 74 mg of 21i. Yield 72%. $^1$H NMR (300 MHz, CDCl$_3$) δ ppm: 8.56 (d, J=1.8 Hz, 1H), 8.48 (dd, J$_1$=4.8 Hz, J$_2$=1.8 Hz, 1H), 7.75 (dt, $J_1$=7.8 Hz, $J_2$=1.8 Hz, 1H), 7.47 (br s, 1H), 7.28 (dd, $J_1$=7.5 Hz, $J_2$=4.2 Hz, 1H), 7.22 (br s, 2H), 7.11 (d, J=8.4 Hz, 1H), 6.78 (d, J=2.4 Hz, 1H), 6.75 (dd, $J_1$=8.1 Hz, $J_2$=2.7 Hz, 1H), 4.54 (br s, 2H), 3.99 (q, J=7.2 Hz, 2H), 3.76 (s, 3H), 2.88 (t, J=8.1 Hz, 2H), 2.43 (t, J=8.0 Hz, 2H), 1.12 (t, J=7.2 Hz, 3H); $^{13}$C NMR (75 MHz, CDCl$_3$) δ ppm: 173.0, 159.0, 149.6, 148.2, 141.4, 139.3, 138.4, 136.8, 136.2, 135.8, 133.7, 131.2, 130.0, 129.9, 128.7, 123.1, 114.6, 111.6, 62.6, 60.5, 55.2, 35.5, 28.5, 14.1; HRMS (EI) m/z: calcd for C$_{24}$H$_{25}$NO$_4$: 391.1784, found: 391.1768.

Example 54: ethyl 3-[4-methoxy-3'-methyl-4'-(pyridin-3-yl)biphenyl-2-yl]propionate (21j)

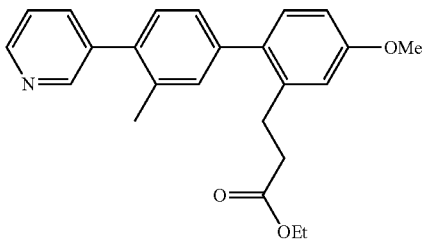 [SMILES: CCOC(=O)CCc1cc(OC)ccc1-c1ccc(-c2cccnc2)c(C)c1]

Yield 30% (CH$_2$Cl$_2$/AcOEt 20:1). $^1$H NMR (300 MHz, CDCl$_3$) δ ppm: 8.66 (d, J=1.5 Hz, 1H), 8.61 (dd, $J_1$=4.8 Hz, $J_2$=1.4 Hz, 1H), 7.71 (ddd, $J_1$=7.8 Hz, $J_2$=2.2 Hz, $J_3$=1.7 Hz, 1H), 7.37 (ddd, $J_1$=7.8 Hz, $J_2$=4.8 Hz, $J_3$=0.8 Hz, 1H), 7.24-7.17 (m, 3H), 7.17 (d, J=8.4 Hz, 1H), 6.86 (d, J=2.4 Hz, 1H), 6.82 (dd, $J_1$=8.3 Hz, $J_2$=2.7 Hz, 1H), 4.09 (q, J=7.1 Hz, 2H), 3.84 (s, 3H), 2.97 (t, J=8.0 Hz, 2H), 2.49 (t, J=8.0 Hz, 2H), 2.31 (s, 3H), 1.21 (t, J=7.1 Hz, 3H); $^{13}$C NMR (75 MHz, CDCl$_3$) δ ppm: 172.8, 159.0, 150.0, 148.1, 141.1, 139.3, 137.2, 136.5, 135.4, 134.0, 131.6, 131.3, 129.7, 127.1, 123.0, 114.5, 111.6, 60.4, 55.3, 35.4, 28.5, 20.4, 14.2.

Example 55: ethyl 3-[3'-(fluoromethyl)-4-methoxy-4'-(pyridin-3-yl)biphenyl-2-yl]propionate (21k)

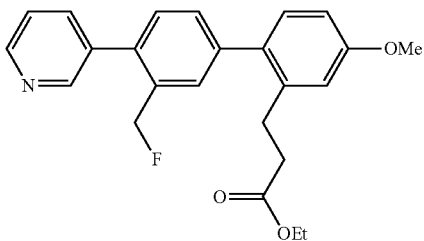

Yield 46% (CH$_2$Cl$_2$/AcOEt 5:1). $^1$H NMR (300 MHz, CDCl$_3$) δ ppm: 8.69 (d, J=1.8 Hz, 1H), 8.66 (dd, $J_1$=4.8 Hz, $J_2$=1.2 Hz, 1H), 7.80 (dt, $J_1$=7.8 Hz, $J_2$=2.0 Hz, 1H), 7.51 (s, 1H), 7.35-7.43 (m, 3H), 7.18 (d, J=8.1 Hz, 1H), 6.87 (d, J=2.4 Hz, 1H), 6.84 (dd, $J_1$=8.4 Hz, $J_2$=2.7 Hz, 1H), 5.29 (d, J=48.0 Hz, 2H), 4.08 (q, J=7.1 Hz, 2H), 3.84 (s, 3H), 2.96 (t, J=8.0 Hz, 2H), 2.49 (t, J=8.0 Hz, 2H), 1.20 (t, J=7.1 Hz, 3H); $^{19}$F NMR (282 MHz, CDCl$_3$) δ ppm: −198.37 (t, J=48.8 Hz, 1F); $^{13}$C NMR (75 MHz, CDCl$_3$) δ ppm: 172.7, 159.2, 149.8, 148.8, 141.6, 139.3, 137.0 (d, $^3$J=3.8 Hz), 136.7, 136.6, 135.4, 133.3 (d, $^2$J=15.8 Hz), 131.4, 131.3, 130.4 (d, $^3$J=3.5 Hz), 130.1, 123.1, 114.5, 111.7, 85.1 (d, $^1$J=164.9 Hz), 60.4, 55.3, 35.4, 28.4, 14.1; HRMS (EI) m/z: calcd for C$_{24}$H$_{24}$FNO$_3$: 393.1740, found: 393.1713.

Example 56: ethyl 3-[3'-(difluoromethyl)-4-methoxy-4'-(pyridin-3-yl)biphenyl-2-yl]propionate (21l)

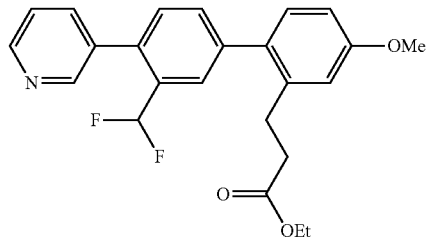 [SMILES: CCOC(=O)CCc1cc(OC)ccc1-c1ccc(-c2cccnc2)c(C(F)F)c1]

Yield 43% (CH$_2$Cl$_2$/AcOEt 10:1). $^1$H NMR (300 MHz, CDCl$_3$) δ ppm: 8.69 (dd, $J_1$=4.7 Hz, $J_2$=1.7 Hz, 2H), 7.76 (dt, $J_1$=7.8 Hz, $J_2$=2.0 Hz, 1H), 7.72 (br s, 1H), 7.50 (d, J=7.8 Hz, 1H), 7.42 (dd, $J_1$=8.0 Hz, $J_2$=5.6 Hz, 1H), 7.38 (d, J=7.8 Hz, 1H), 7.19 (d, J=8.4 Hz, 1H), 6.88 (d, J=2.7 Hz, 1H), 6.85 (dd, $J_1$=8.3 Hz, $J_2$=2.6 Hz, 1H), 6.53 (t, J=54.9 Hz, 1H), 4.08 (q, J=7.2 Hz, 2H), 3.85 (s, 3H), 2.96 (t, J=8.0 Hz, 2H), 2.50 (t, J=7.8 Hz, 2H), 1.20 (t, J=7.1 Hz, 3H); $^{19}$F NMR (282 MHz, CDCl$_3$) δ ppm: −107.88 (d, J=56.1 Hz, 2F); $^{13}$C NMR (75 MHz, CDCl$_3$) δ ppm: 172.6, 159.4, 149.9, 149.2, 141.9, 139.3, 136.8, 135.8 (t, $^3$J=5.8 Hz), 134.3, 132.9, 131.9 (t, $^2$J=21.9 Hz), 131.8, 131.3, 130.4, 126.9 (t, $^3$J=5.4 Hz), 123.1, 114.6, 112.9 (t, $^1$J=235.8 Hz), 111.8, 60.4, 55.3, 35.4, 28.4, 14.1; HRMS (EI) m/z: calcd for C$_{24}$H$_{23}$F$_2$NO$_3$: 411.1646, found: 411.1658.

Example 57: 3-[2'-(hydroxymethyl)-4''-methoxy-3-methyl-(1,1';4',1'')terphenyl-2''-yl]propionic acid (22a)

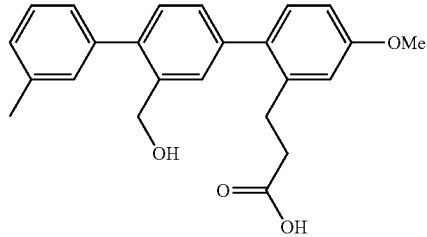

Yield 97%. $^1$H NMR (300 MHz, CDCl$_3$) δ ppm: 7.39 (d, J=1.5 Hz, 1H), 7.28-7.14 (m, 5H), 7.12 (t, J=3.1 Hz, 2H), 6.80-6.72 (m, 2H), 4.58 (s, 2H), 3.77 (s, 3H), 2.89 (t, J=7.9 Hz, 2H), 2.47 (t, J=7.9 Hz, 2H), 2.33 (s, 3H); $^{13}$C NMR (75 MHz, CDCl$_3$) δ ppm: 177.5, 159.0, 140.3, 140.3, 139.8, 139.0, 137.9, 137.7, 134.1, 131.3, 129.9, 129.3, 128.5, 128.1, 128.0, 126.2, 114.6, 111.7, 63.1, 55.3, 35.2, 28.4, 21.5; HRMS (EI) m/z: calcd for C$_{24}$H$_{24}$O$_4$: 376.1674, found: 376.1657.

Example 58: 3-[4"-methoxy-3,2'-dimethyl-(1,1';4',1")terphenyl-2"-yl]propionic acid (22b)

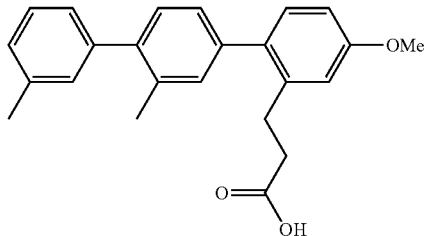 [SMILES: COc1ccc(-c2ccc(-c3cccc(C)c3)c(C)c2)c(CCC(=O)O)c1]

Yield 99%. $^1$H RMN (300 MHz, CDCl$_3$) δ ppm: 7.24 (t, J=7.5 Hz, 1H), 7.19-7.02 (m, 7H), 6.80-6.70 (m, 2H), 3.76 (s, 3H), 2.90 (t, J=7.8 Hz, 2H), 2.45 (t, J=7.8 Hz, 2H), 2.34 (s, 3H), 2.23 (s, 3H); $^{13}$C RMN (75 MHz, CDCl$_3$) δ ppm: 178.5, 158.9, 141.6, 140.5, 139.9, 139.0, 137.6, 135.1, 134.4, 131.4, 131.2, 130.0, 129.6, 127.9, 127.5, 126.7, 126.3, 114.5, 111.6, 55.3, 35.1, 28.3, 21.5, 20.6; HRMS (EI) m/z: calcd for C$_{24}$H$_{24}$O$_3$: 360.1725; found: 360.1727.

Example 59: 3-[2'-(fluoromethyl)-4"-methoxy-3-methyl-(1,1';4',1")terphenyl-2"-yl]propionic acid (22c)

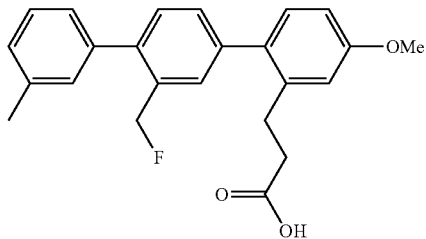 [SMILES: COc1ccc(-c2ccc(-c3cccc(C)c3)c(CF)c2)c(CCC(=O)O)c1]

Yield 99%. $^1$H NMR (300 MHz, CDCl$_3$) δ ppm: 7.47 (s, 1H), 7.39-7.30 (m, 3H), 7.25-7.18 (m, 4H), 6.79 (d, J=2.6 Hz, 1H), 6.76 (dd, J$_1$=8.2 Hz, J$_2$=2.6 Hz, 1H), 5.25 (d, J=48.0 Hz, 2H), 3.76 (s, 3H), 2.90 (t, J=7.9 Hz, 2H), 2.46 (t, J=7.9 Hz, 2H), 2.34 (s, 3H); $^{19}$F NMR (282 MHz, CDCl$_3$) δ ppm: −201.25 (t, J=47.9 Hz, 1F); $^{13}$C NMR (75 MHz, CDCl$_3$) δ ppm: 178.1, 159.2, 140.7 (d, $^3$J=4.4 Hz), 140.5, 139.7, 139.0, 138.0, 133.8, 133.3 (d, $^2$J=15.9 Hz), 131.4, 130.5, 130.4, 130.0, 129.9, 129.8, 128.2 (d, $^3$J=4.9 Hz), 126.4, 114.6, 111.8, 82.8 (d, $^1$J=164.3 Hz), 55.3, 35.0, 28.3, 21.5; HRMS (EI) m/z: calcd for C$_{24}$H$_{23}$FO$_3$: 378.1631, found: 378.1637.

Example 60: 3-[2'-(difluoromethyl)-4"-methoxy-3-methyl-(1,1';4',1")terphenyl-2"-yl]propionic acid (22d)

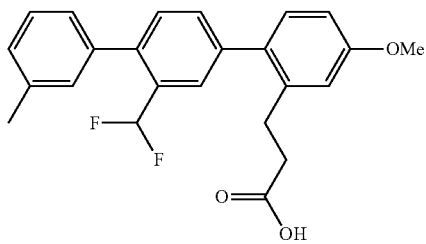 [SMILES: COc1ccc(-c2ccc(-c3cccc(C)c3)c(C(F)F)c2)c(CCC(=O)O)c1]

Yield 98%. $^1$H NMR (300 MHz, CDCl$_3$) δ ppm: 7.64 (s, 1H), 7.37 (d, J=7.8 Hz, 1H), 7.30 (t, J=7.8 Hz, 2H), 7.19 (d, J=8.4 Hz, 2H), 7.15 (d, J=8.4 Hz, 2H), 6.82 (d, J=2.4 Hz, 1H), 6.80 (dd, J$_1$=8.1 Hz, J$_2$=2.4 Hz, 1H), 6.54 (t, J=54.9 Hz, 1H), 3.79 (s, 3H), 2.91 (t, J=7.8 Hz, 2H), 2.49 (t, J=7.8 Hz, 2H), 2.38 (s, 3H); $^{19}$F NMR (282 MHz, CDCl$_3$) δ ppm: −107.88 (d, J=55.9 Hz, 2F); $^{13}$C NMR (75 MHz, CDCl$_3$) δ ppm: 178.7, 159.3, 140.7, 140.0 (t, $^3$J=6.3 Hz), 139.0, 138.3, 138.1, 133.4, 131.6 (t, $^2$J=20.4 Hz), 131.4, 131.3 (2×), 130.2, 130.1, 128.6, 128.3, 126.6, 126.4 (t, $^3$J=4.8 Hz), 114.6, 113.1 (t, $^1$J=234.7 Hz), 111.8, 55.3, 35.0, 28.1, 21.4; HRMS (EI) m/z: calcd for C$_{24}$H$_{22}$F$_2$O$_3$: 396.1537, found: 396.1527.

Example 61: 3-[2'-(hydroxymethyl)-4"-methoxy-3-(trifluoromethyl)-(1,1';4',1")terphenyl-2"-yl]propionic acid (22e)

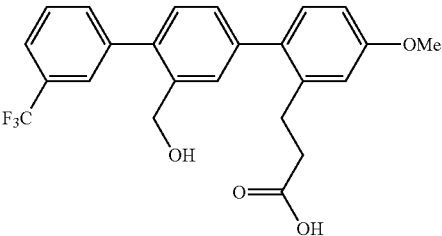

Yield 98%. $^1$H NMR (300 MHz, CDCl$_3$) δ ppm: 7.63 (s, 1H), 7.57 (d, J=7.5 Hz, 2H), 7.47 (t, J=7.6 Hz, 1H), 7.42 (s, 1H), 7.26-7.19 (m, 2H), 7.12 (d, J=7.9 Hz, 1H), 6.78 (d, J=2.6 Hz, 1H), 6.76 (dd, J$_1$=8.0 Hz, J$_2$=2.6 Hz, 1H), 4.53 (s, 2H), 3.77 (s, 3H), 2.89 (t, J=7.9 Hz, 2H), 2.47 (t, J=7.9 Hz, 2H); $^{19}$F NMR (282 MHz, CDCl$_3$) δ ppm: −63.05 (s, 3F); $^{13}$C NMR (75 MHz, CDCl$_3$) δ ppm: 177.5, 159.2, 141.3, 141.2, 139.0, 138.3, 137.7, 133.8, 132.6, 131.3, 130.7 (q, $^2$J=32.1 Hz), 130.0, 129.8, 128.9, 128.7, 126.0 (q, $^3$J=3.8 Hz), 124.1 (q, $^1$J=270.6 Hz), 124.0 (q, $^3$J=3.8 Hz), 114.7, 111.8, 62.9, 55.3, 35.2, 28.4; HRMS (EI) m/z: calcd for C$_{24}$H$_{21}$F$_3$O$_4$: 430.1392, found: 430.1314.

Example 62: 3-[2'-methyl-4"-methoxy-3-(trifluoromethyl)-(1,1';4',1")terphenyl-2"-yl]propionic acid (22f)

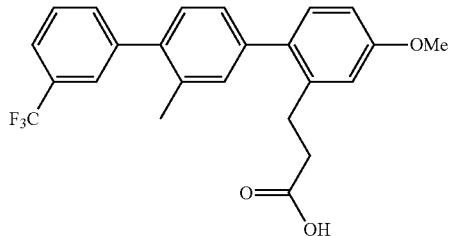 [SMILES: COc1ccc(-c2ccc(-c3cccc(C(F)(F)F)c3)c(C)c2)c(CCC(=O)O)c1]

Yield 99%. $^1$H RMN (300 MHz, CDCl$_3$) δ ppm: 7.70-7.52 (m, 4H), 7.28-7.16 (m, 4H), 6.88 (d, J=2.4 Hz, 1H), 6.85 (dd, J$_1$=8.2 Hz, J$_2$=2.7 Hz, 1H), 3.85 (s, 3H), 3.00 (t, J=8.0 Hz, 2H) 2.55 (t, J=8.0 Hz, 2H), 2.31 (s, 3H); $^{19}$F NMR (282 MHz, CDCl$_3$) δ ppm: −63.02 (s, 3F); $^{13}$C RMN (75 MHz, CDCl$_3$) δ ppm: 178.9, 159.0, 142.4, 140.8, 138.9, 138.9, 135.1, 134.1, 132.6, 131.5, 131.4, 130.5 (q, $^2$J=32.1 Hz), 129.6, 128.5, 127.0, 126.0 (q, $^3$J=3.8 Hz), 124.2 (q, $^1$J=270.8 Hz), 123.6 (q, $^3$J=3.5 Hz), 114.6, 111.7, 55.3, 35.1, 28.2, 20.4; HRMS (EI) m/z: calcd for $C_{24}H_{21}F_3O_3$: 413.1365 (M−1); found: 413.1366.

Example 63: 3-[2'-(fluoromethyl)-4"-methoxy-3-(trifluoromethyl)-(1,1';4',1")terphenyl-2"-yl]propionic acid (22g)

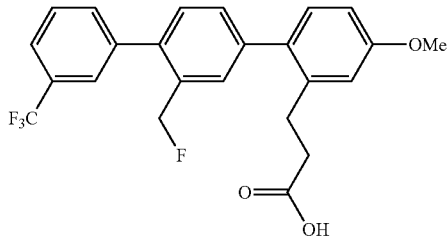 [SMILES: COc1ccc(-c2ccc(-c3cccc(C(F)(F)F)c3)c(CF)c2)c(CCC(=O)O)c1]

Yield 99%. $^1$H NMR (300 MHz, CDCl$_3$) δ ppm: 7.71 (s, 1H), 7.66 (s, 1H), 7.63 (s, 1H), 7.58 (t, J=7.4 Hz, 1H), 7.50 (s, 1H), 7.38 (s, 2H), 7.19 (d, J=8.2 Hz, 1H), 6.88 (d, J=2.5 Hz, 1H), 6.85 (dd, J$_1$=8.2 Hz, J$_2$=2.5 Hz, 1H), 5.29 (d, J=47.9 Hz, 2H), 3.85 (s, 3H), 2.97 (t, J=7.9 Hz, 2H), 2.55 (t, J=7.9 Hz, 2H); $^{19}$F NMR (282 MHz, CDCl$_3$) δ ppm: −63.09 (s, 3F), −199.50 (t, J=47.9 Hz, 1F); $^{13}$C NMR (75 MHz, CDCl$_3$) δ ppm: 178.2, 159.3, 141.4, 140.6, 139.3 (d, $^3$J=4.2 Hz), 139.0, 133.4, 133.2 (d, $^2$J=15.8 Hz), 131.4, 131.1, 131.0, 130.8 (q, $^2$J=32.1 Hz), 130.2 (d, $^3$J=3.3 Hz), 130.0, 128.8, 126.1 (q, $^3$J=3.8 Hz), 124.3 (q, $^3$J=3.8 Hz), 124.1 (q, $^1$J=270.8 Hz), 114.7, 111.8, 82.6 (d, $^1$J=165.1 Hz), 55.3, 35.0, 28.2; HRMS (EI) m/z: calcd for $C_{24}H_{20}F_4O_3$: 432.1349, found: 432.1337.

Example 64: 3-[2'-(difluoromethyl)-4"-methoxy-3-(trifluoromethyl)-(1,1';4',1")terphenyl-2"-yl]propionic acid (22h)

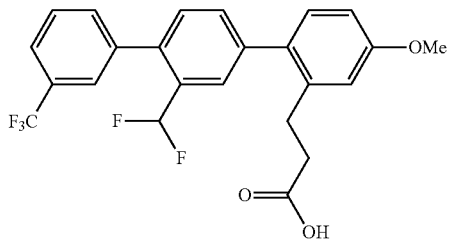

Yield 98%. $^1$H NMR (300 MHz, CDCl$_3$) δ ppm: 7.60 (d, J=5.1 Hz, 3H), 7.49 (d, J=5.4 Hz, 2H), 7.36 (d, J=7.8 Hz, 1H), 7.25 (d, J=7.8 Hz, 1H), 7.08 (d, J=8.1 Hz, 1H), 6.79-6.71 (m, 2H), 6.40 (t, J=54.8 Hz, 1H), 3.72 (s, 3H), 2.83 (t, J=7.2 Hz, 2H), 2.41 (t, J=7.2 Hz, 2H); $^{19}$F NMR (282 MHz, CDCl$_3$) δ ppm: −63.15 (s, 3F), −108.02 (d, J=54.7 Hz, 2F); $^{13}$C NMR (75 MHz, CDCl$_3$) δ ppm: 159.4, 141.7, 139.3, 138.1 (t, $^3$J=6.0 Hz), 133.0, 132.8, 131.7, 131.7 (t, $^2$J=19.5 Hz), 131.3, 131.0 (q, $^2$J=32.4 Hz), 130.2, 128.9, 126.8 (t, $^3$J=5.4 Hz), 126.2 (q, 3J=3.4 Hz), 124.7 (q, $^3$J=3.9 Hz), 124.0 (q, $^1$J=270.8 Hz), 114.7, 112.9 (t, $^1$J=235.6 Hz), 111.7, 55.3, 29.7, 28.3; HRMS (EI) m/z: calcd for $C_{24}H_{19}F_5O_3$: 450.1254, found: 450.1260.

Example 65: 3-[3'-(hydroxymethyl)-4-methoxy-4'-(pyridin-3-yl)biphenyl-2-yl]propionic acid (22i)

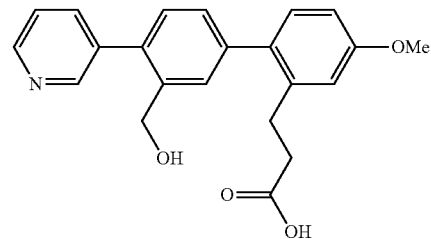

Yield 76%. $^1$H NMR (300 MHz, DMSO-d$_6$) δ ppm: 8.66 (d, J=1.8 Hz, 1H), 8.59 (dd, J$_1$=4.8 Hz, J$_2$=1.8 Hz, 1H), 7.91 (dt, J$_1$=7.8 Hz, J$_2$=2.0 Hz, 1H), 7.50 (br s, 1H), 7.48 (dd, J$_1$=7.8 Hz, J$_2$=4.8 Hz, 1H), 7.33 (d, J=7.8 Hz, 1H), 7.29 (dd, J$_1$=7.8 Hz, J$_2$=1.5 Hz, 1H), 7.14 (d, J=8.4 Hz, 1H), 6.94 (d, J=2.7 Hz, 1H), 6.86 (dd, J$_1$=8.4 Hz, J$_2$=2.7 Hz, 1H), 4.44 (br s, 2H), 3.78 (s, 3H), 2.82 (t, J=7.7 Hz, 2H), 2.43 (t, J=8.0 Hz, 2H); $^{13}$C NMR (75 MHz, DMSO-d$_6$) (ppm: 173.7, 158.6, 149.3, 148.1, 140.6, 139.6, 139.4, 136.4, 135.6, 134.9, 133.4, 130.8, 129.4, 129.2, 127.8, 123.1, 114.3, 111.4, 60.7, 55.0, 34.7, 27.8; HRMS (EI) m/z: calcd for $C_{22}H_{21}NO_4$: 363.1471, found: 363.1420; yellowish oil, mp: 174-176° C.

Example 66: 3-[4-methoxy-3'-methyl-4'-(pyridin-3-yl)biphenyl-2-yl]propionic acid (22j)

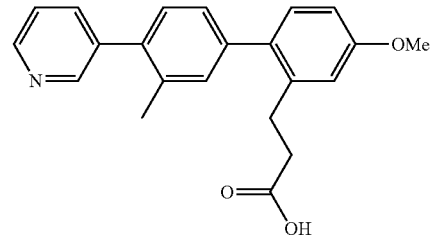

Yield 96%. $^1$H NMR (300 MHz, CDCl$_3$) δ ppm: 8.67 (s, 1H), 8.57 (d, J=3.7 Hz, 1H), 7.77 (dd, J=7.8 Hz, 1.5 Hz, 1H), 7.42 (dd, J$_1$=7.8 Hz, J$_2$=4.9 Hz, 1H), 7.24-7.16 (m, 3H), 7.16 (d, J=8.4 Hz, 1H), 6.88 (d, J=2.5 Hz, 1H), 6.82 (dd, J$_1$=8.4 Hz, J$_2$=2.6 Hz, 1H), 3.84 (s, 3H), 2.97 (t, J=8.3 Hz, 2H), 2.54 (t, J=8.3 Hz, 2H), 2.27 (s, 3H); $^{13}$C NMR (75 MHz, CDCl$_3$) δ ppm: 177.5, 159.1, 148.9, 146.6, 141.4, 139.6, 137.9, 137.6, 135.9, 135.4, 134.0, 131.6, 131.1, 129.7, 127.2, 123.4, 114.5, 111.5, 55.3, 35.7, 28.7, 20.4; HRMS (EI) m/z: calcd for $C_{22}H_{21}NO_3$: 348.1600 (M+1), found: 348.1595; white solid, mp: 153-155° C.

Example 67: 3-[3'-(fluoromethyl)-4-methoxy-4'-(pyridin-3-yl)biphenyl-2-yl]propionic acid (22k)

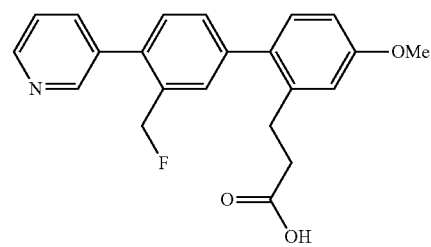

Yield 89%. $^1$H NMR (300 MHz, CDCl$_3$) δ ppm: 8.72 (s, 1H), 8.65 (s, 1H), 7.87 (d, J=7.5 Hz, 1H), 7.45 (s, 1H), 7.33-7.47 (m, 3H), 7.19 (d, J=7.8 Hz, 1H), 6.88 (d, J=2.4 Hz, 1H), 6.84 (dd, J$_1$=7.8 Hz, J$_2$=2.4 Hz, 1H), 5.26 (d, J=48.3 Hz, 2H), 3.85 (s, 3H), 2.96 (t, J=7.5 Hz, 2H), 2.55 (t, J=7.2 Hz, 2H); $^{19}$F NMR (282 MHz, CDCl$_3$) δ ppm: −197.91 (t, J=48.1 Hz, 1F); $^{13}$C NMR (75 MHz, CDCl$_3$) δ ppm: 159.3, 148.8, 147.6, 141.9, 139.6, 137.7, 136.6, 136.0, 133.3 (d, $^2$J=17.6 Hz), 133.2, 131.5 (d, $^3$J=5.7 Hz), 131.2, 130.5, 130.2, 123.5, 114.6, 111.5, 82.5 (d, $^1$J=164.5 Hz), 55.2, 35.8, 28.6; HRMS (EI) m/z: calcd for C$_{22}$H$_{20}$FNO$_3$: 365.1427, found: 365.1400; yellowish solid.

Example 68: 3-[3'-(difluoromethyl)-4-methoxy-4'-(pyridin-3-yl)biphenyl-2-yl]propionic acid (22l)

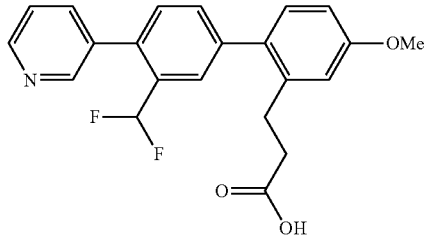

Yield 86%. $^1$H NMR (300 MHz, CDCl$_3$) δ ppm: 8.71 (s, 1H), 8.66 (d, J=4.5 Hz, 1H), 7.81 (d, J=7.8 Hz, 1H), 7.69 (s, 1H), 7.48 (d, J=7.8 Hz, 1H), 7.50 (dd, J$_1$=7.8 Hz, J$_2$=5.0 Hz, 1H), 7.34 (d, J=7.8 Hz, 1H), 7.18 (d, J=8.4 Hz, 1H), 6.89 (d, J=2.1 Hz, 1H), 6.83 (dd, J$_1$=8.4 Hz, J$_2$=2.4 Hz, 1H), 6.49 (t, J=54.8 Hz, 1H), 3.84 (s, 3H), 2.94 (t, J=8.0 Hz, 2H), 2.54 (t, J=8.1 Hz, 2H); $^{19}$F NMR (282 MHz, CDCl$_3$) δ ppm: −107.94 (d, J=54.7 Hz, 2F); $^{13}$C NMR (75 MHz, CDCl$_3$) δ ppm: 176.6, 159.4, 148.9, 147.9, 142.1, 139.5, 137.8, 135.3 (t, $^3$J=5.6 Hz), 134.9, 132.9, 131.9 (t, $^2$J=21.7 Hz), 131.2, 130.5, 127.0 (t, $^3$J=5.2 Hz), 123.5, 114.6, 113.0 (t, $^1$J=236.1 Hz), 111.7, 55.3, 35.5, 28.5; HRMS (EI) m/z: calcd for C$_{22}$H$_{19}$F$_2$NO$_3$: 383.1333, found: 383.1313; white solid.

Example 69: ethyl 3-[3,2'-dimethyl-4"-propoxy-(1,1';4',1")terphenyl-2"-yl]propionate (23a)

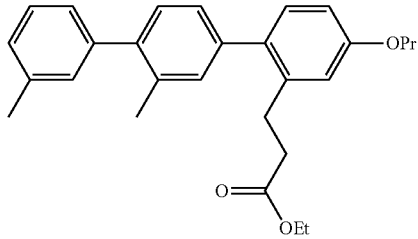

Yield 78% (hexane/AcOEt 10:1). $^1$H NMR (300 MHz, CDCl$_3$) δ ppm: 7.28 (t, J=7.6 Hz, 1H), 7.21 (d, J=7.7 Hz, 1H), 7.18-7.08 (m, 6H), 6.82 (d, J=2.5 Hz, 1H), 6.77 (dd, J$_1$=8.4 Hz, J$_2$=2.6 Hz, 1H), 4.05 (q, J=7.1 Hz, 2H), 3.92 (t, J=6.6 Hz, 2H), 2.95 (t, J=8.0 Hz, 2H), 2.46 (t, J=8.0 Hz, 2H), 2.38 (s, 3H), 2.28 (s, 3H), 1.80 (sex, J=7.1 Hz, 2H), 1.18 (t, J=7.1 Hz, 3H), 1.03 (t, J=7.4 Hz, 3H); $^{13}$C RMN (75 MHz, CDCl$_3$) δ ppm: 172.9, 158.4, 141.7, 140.3, 140.1, 139.3, 137.6, 135.0, 134.2, 131.3, 130.0, 129.5, 127.9, 127.4, 126.7, 126.3, 115.1, 112.1, 69.5, 60.3, 35.5, 28.6, 22.6, 21.5, 20.5, 14.2, 10.5; HRMS (EI) m/z: calcd for C$_{28}$H$_{32}$O$_3$: 439.2249 (M+Na), found: 439.2245.

Example 70: ethyl 3-[4"-(ethoxycarbonylmethoxy)-3,2'-dimethyl-(1,1';4',1")terphenyl-2"-yl]propionate (23b)

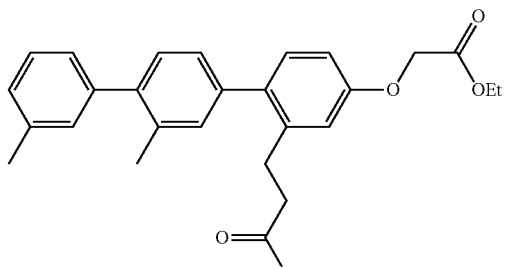

Yield 73% (hexane/AcOEt 7:1). $^1$H NMR (300 MHz, CDCl$_3$) δ ppm: 7.32 (t, J=7.7 Hz, 1H), 7.27-7.11 (m, 7H), 6.88 (d, J=2.6 Hz, 1H), 6.80 (dd, J$_1$=8.4 Hz, J$_2$=2.7 Hz, 1H), 4.65 (s, 2H), 4.31 (q, J=7.1 Hz, 2H), 4.09 (q, J=7.1 Hz, 2H), 2.97 (t, J=8.0 Hz, 2H), 2.48 (t, J=8.0 Hz, 2H), 2.42 (s, 3H), 2.31 (s, 3H), 1.33 (t, J=7.1 Hz, 3H), 1.21 (t, J=7.1 Hz, 3H); $^{13}$C NMR (75 MHz, CDCl$_3$) δ ppm: 172.8, 168.9, 157.1, 141.6, 140.5, 139.8, 139.6, 137.6, 135.5, 135.1, 131.4, 131.2, 130.0, 129.6, 127.9, 127.5, 126.7, 126.3, 115.4, 112.0, 65.5, 61.4, 60.4, 35.4, 28.5, 21.5, 20.5, 14.2; HRMS (EI) m/z: calcd for C$_{29}$H$_{32}$O$_5$: 483.2147 (M+Na), found: 483.2140.

Example 71: ethyl 3-[2'-methyl-4"-propoxy-3-(trifluoromethyl)-(1,1';4',1")terphenyl-2"-yl]propionate (23c)

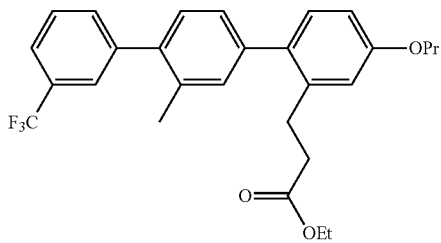

Yield 75% (hexane/AcOEt 20:1). $^1$H NMR (300 MHz, CDCl$_3$) δ ppm: 7.68-7.51 (m, 4H), 7.25-7.17 (m, 3H), 7.16 (d, J=8.2 Hz, 1H), 6.86 (d, J=2.5 Hz, 1H), 6.82 (dd, J$_1$=8.3 Hz, J$_2$=2.6 Hz, 1H), 4.09 (q, J=7.1 Hz, 2H), 3.96 (t, J=6.6 Hz, 2H), 2.97 (t, J=8.1 Hz, 2H), 2.49 (t, J=8.1 Hz, 2H), 2.30 (s, 3H), 1.84 (sex, J=7.1 Hz, 2H), 1.21 (t, J=7.1 Hz, 3H), 1.06 (t, J=7.4 Hz, 3H); $^{19}$F NMR (282 MHz, CDCl$_3$) δ ppm: −63.05 (s, 3F); $^{13}$C NMR (75 MHz, CDCl$_3$) δ ppm: 172.9, 158.6, 142.4, 141.0, 139.3, 138.7, 135.0, 133.9, 132.6, 131.5, 131.2, 130.6 (q, $^2$J=31.9 Hz), 129.5, 128.6, 127.0, 126.0 (q, $^3$J=3.8 Hz), 124.2 (q, $^1$J=270.5 Hz), 123.6 (q, $^3$J=4.0 Hz), 115.1, 112.1, 69.5, 60.4, 35.5, 29.7, 28.5, 22.6, 20.4, 14.2, 10.6.

Example 72: 3-[3,2'-dimethyl-4"-propoxy-(1,1';4',1")terphenyl-2"-yl]propionic acid (24a)

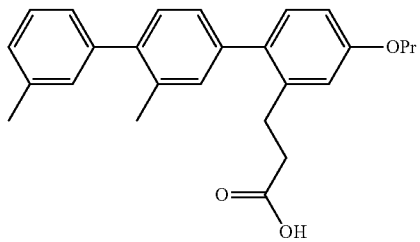

Yield 99%. ¹H NMR (300 MHz, CDCl₃) δ ppm: 7.35 (t, J=7.5 Hz, 1H), 7.28 (d, J=7.7 Hz, 1H), 7.25-7.15 (m, 6H), 6.90 (d, J=2.5 Hz, 1H), 6.86 (dd, $J_1$=8.3 Hz, $J_2$=2.6 Hz, 1H), 3.99 (t, J=6.6 Hz, 2H), 3.02 (t, J=8.0 Hz, 2H), 2.58 (t, J=8.0 Hz, 2H), 2.45 (s, 3H), 2.35 (s, 3H), 1.87 (sex, J=7.1 Hz, 2H), 1.10 (t, J=7.4 Hz, 3H); ¹³C NMR (75 MHz, CDCl₃) δ ppm: 179.1, 158.5, 141.6, 140.4, 140.0, 138.8, 137.6, 135.1, 134.2, 131.3, 131.2, 130.0, 129.6, 127.9, 127.4, 126.7, 126.3, 115.1, 112.2, 69.5, 35.2, 28.2, 22.6, 21.4, 20.5, 10.5; HRMS (EI) m/z: calcd for C₂₆H₂₈O₃: 387.1960 (M−1), found: 387.1955.

Example 73: 3-[4"-(carboxymethoxy)-3,2'-dimethyl-(1,1';4,1")terphenyl-2"-yl]propionic acid (24b)

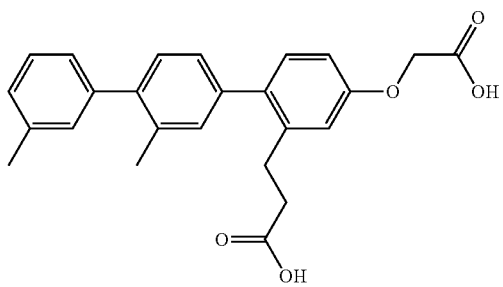 [SMILES: Cc1cccc(-c2ccc(-c3ccc(OCC(=O)O)cc3CCC(=O)O)cc2C)c1]

Yield 99%. ¹H NMR (300 MHz, CDCl₃) δ ppm: 7.35 (t, J=7.5 Hz, 1H), 7.28 (d, J=7.7 Hz, 1H), 7.25-7.13 (m, 6H), 6.94 (d, J=2.6 Hz, 1H), 6.86 (dd, $J_1$=8.4 Hz, $J_2$=2.6 Hz, 1H), 4.74 (s, 2H), 3.02 (t, J=7.7 Hz, 2H), 2.58 (t, J=7.7 Hz, 2H), 2.45 (s, 3H), 2.34 (s, 3H); ¹³C NMR (75 MHz, CDCl₃) δ ppm: 179.4, 174.8, 156.7, 141.5, 140.6, 139.5, 139.2, 137.6, 135.7, 135.2, 131.5, 131.1, 130.0, 129.6, 127.9, 127.5, 126.6, 126.3, 115.2, 112.3, 64.8, 34.9, 28.1, 21.4, 20.5; HRMS (EI) m/z: calcd for C₂₅H₂₄O₅: 403.1545 (M−1), found: 403.1543; white solid, mp: 130-132° C.

Example 74: 3-[2'-methyl-4"-propoxy-3-(trifluoromethyl)-(1,1';4',1")terphenyl-2"-yl]propionic acid (24c)

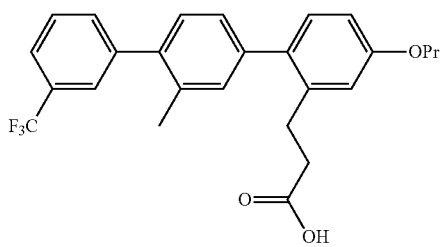

Yield 99%. ¹H NMR (300 MHz, CDCl₃) δ ppm: 7.69-7.50 (m, 4H), 7.24-7.12 (m, 4H), 6.86 (d, J=2.4 Hz, 1H), 6.82 (dd, $J_1$=8.3 Hz, $J_2$=2.6 Hz, 1H), 3.96 (t, J=6.6 Hz, 2H), 2.97 (t, J=8.1 Hz, 2H), 2.54 (t, J=8.1 Hz, 2H), 2.29 (s, 3H), 1.83 (sex, J=7.1 Hz, 2H), 1.06 (t, J=7.4 Hz, 3H); ¹⁹F NMR (282 MHz, CDCl₃) b ppm: −63.03 (s, 3F); ¹³C NMR (75 MHz, CDCl₃) δ ppm: 177.9, 158.6, 142.4, 140.9, 139.3, 138.8, 135.1, 133.9, 132.6, 131.5, 131.3, 130.6 (q, ²J=31.8 Hz), 129.6, 128.5, 127.0, 126.1 (q, ³J=3.8 Hz), 124.2 (q, ¹J=270.5 Hz), 123.6 (q, ³J=3.8 Hz), 115.1, 112.2, 69.6, 35.0, 28.3, 22.6, 20.4, 10.5.

Example 75: ethyl 3-(3-methoxyphenyl)propionate (25)

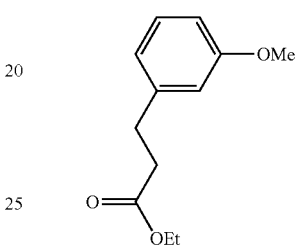

A solution of 3-methoxyphenylsuccinic acid (1.500 g, 8.32 mmol) in dry ethanol (15 mL) with a small quantity of DOWEX™ strong acid ion exchange resin was refluxed for 22 h. The reaction mixture was filtered and the solvent evaporated in vacuo to give 1.618 g of ester 25. Yield 93%. ¹H NMR (300 MHz, CDCl₃) b ppm: 7.15 (q, J=8.6 Hz, 1H), 6.72 (d, J=7.8 Hz, 1H), 6.65-6.70 (m, 2H), 4.06 (q, J=7.1 Hz, 2H), 3.72 (s, 3H), 2.86 (t, J=7.9 Hz, 2H), 2.54 (t, J=7.9 Hz, 2H), 1.17 (t, J=7.1 Hz, 3H); ¹³C NMR (75 MHz, CDCl₃) δ ppm: 172.9, 159.7, 142.2, 129.4, 120.6, 114.0, 111.6, 60.4, 55.1, 35.8, 31.0, 14.2; HRMS (EI) m/z: calcd for C₁₂H₁₆O₃: 208.1099, found: 208.1104.

Example 76: ethyl 3-(2-iodo-5-methoxyphenyl)propionate (26)

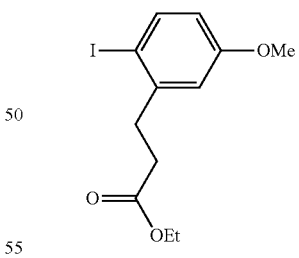

To a solution of n-butyltriphenylphosphonium bromide (7.188 g, 18.00 mmol) in water/acetone (10:1, 200 mL) was added a solution of potassium peroxodisulfate (2.433 g, 9.00 mmol) in water (50 mL), and the mixture was stirred at room temperature for 15 min. The resulting white solid was filtered, washed with cold distilled water and dried in a desiccator over calcium chloride.

To a solution of ester 25 (1.618 g, 7.77 mmol) in acetonitrile (100 mL), iodine (1.972 g, 7.77 mmol) and n-butyltriphenylphosphonium peroxodisulfate (6.455 g, 7.77 mmol) were added and refluxed for 45 min. The reaction mixture was cooled to room temperature and the excess of iodine was removed by dropwise addition of 1M $Na_2S_2O_3$ solution. The colourless solution was transferred to a separatory funnel and the organic layer was separated and dried over $Na_2SO_4$. Evaporation of the solvent followed by means of column chromatography on silica gel (hexane/isopropyl-ether 10:1) gave 1.982 mg of iodinated ester 26 as a yellowish oil. Yield 76%. $^1$H NMR (300 MHz, CDCl$_3$) δ ppm: 7.65 (d, J=8.7 Hz, 1H), 6.82 (d, J=3.0 Hz, 1H), 6.51 (dd, $J_1$=8.7 Hz, $J_2$=3.0 Hz, 1H), 4.14 (q, J=7.1 Hz, 2H), 3.76 (s, 3H), 3.00 (t, J=7.9 Hz, 2H), 2.60 (t, J=7.9 Hz, 2H), 1.25 (t, J=7.1 Hz, 3H); $^{13}$C NMR (75 MHz, CDCl$_3$) δ ppm: 172.4, 160.0, 144.0, 139.9, 115.5, 114.1, 88.6, 60.5, 55.3, 35.9, 34.4, 14.2; HRMS (EI) m/z: calcd for $C_{12}H_{15}IO_3$: 334.0065, found: 334.0082.

Example 77: ethyl 3-[5-methoxy-2-(4,4,5,5-tetramethyl-1,3,2-dioxaborolan-2-yl)phenyl]propionate (27)

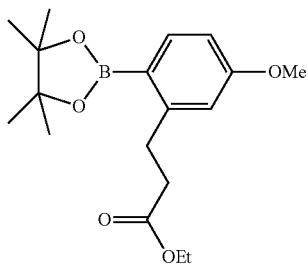 [SMILES: CCOC(=O)CCc1cc(OC)ccc1B1OC(C)(C)C(C)(C)O1]

Yield 60% (hexane/AcOEt 10:1). $^1$H NMR (300 MHz, CDCl$_3$) δ ppm: 7.75 (d, J=8.2 Hz, 1H), 6.74 (d, J=7.8 Hz, 2H), 4.13 (q, J=7.1 Hz, 2H), 3.80 (s, 3H), 3.18 (t, J=8.0 Hz, 2H), 2.57 (t, J=8.0 Hz, 2H), 1.32 (s, 12H), 1.25 (t, J=7.1 Hz, 3H); $^{13}$C NMR (75 MHz, CDCl$_3$) (ppm: 173.3, 161.8, 150.0, 138.2, 115.1, 110.8, 83.2, 60.1, 55.0, 37.3, 31.4, 24.8, 14.3; HRMS (EI) m/z: calcd for $C_{18}H_{27}BO_5$: 333.1987, found: 333.1967.

Example 78: ethyl 3-[3'-formyl-4-methoxy-4'-(pyridin-3-yl)biphenyl-2-yl]propionate (28)

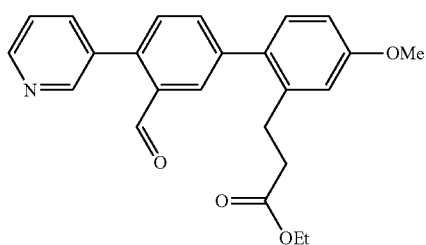 [SMILES: CCOC(=O)CCc1cc(OC)ccc1-c1ccc(-c2cccnc2)c(C=O)c1]

Yield 62% (CH$_2$Cl$_2$/AcOEt 10:1). $^1$H NMR (300 MHz, CDCl$_3$) δ ppm: 10.03 (s, 1H), 8.72 (d, J=4.5 Hz, 2H), 7.98 (d, J=1.5 Hz, 1H), 7.77 (dt, $J_1$=8.1 Hz, $J_2$=2.0 Hz, 1H), 7.63 (dd, $J_1$=8.1 Hz, $J_2$=1.8 Hz, 1H), 7.47 (d, J=8.1 Hz, 1H), 7.45 (dd, $J_1$=8.1 Hz, $J_2$=4.8 Hz, 1H), 7.17 (d, J=8.4 Hz, 1H), 6.88 (d, J=3.0 Hz, 1H), 6.84 (dd, $J_1$=8.1 Hz, $J_2$=3.0 Hz, 1H), 4.07 (q, J=7.1 Hz, 2H), 3.85 (s, 3H), 2.94 (t, J=7.8 Hz, 2H), 2.49 (t, J=8.0 Hz, 2H), 1.19 (t, J=7.2 Hz, 3H); $^{13}$C NMR (75 MHz, CDCl$_3$) δ ppm: 191.2, 172.6, 159.5, 150.2, 149.4, 142.0, 140.1, 139.3, 137.2, 134.8, 133.7, 132.6, 131.3, 131.0, 129.3, 123.2, 114.7, 111.8, 60.4, 55.3, 35.3, 28.4, 14.1; HRMS (EI) m/z: calcd for $C_{24}H_{23}NO_4$: 389.1627, found: 389.1580; yellowish oil.

Example 79: 3-methyl-4-(pyridin-3-yl)phenol (29a)

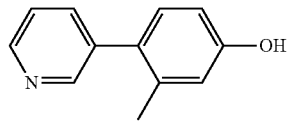

Yield 75% (CH$_2$Cl$_2$/AcOEt 5:1). $^1$H NMR (300 MHz, CDCl$_3$) δ ppm: 8.57 (dd, $J_1$=2.3 Hz, $J_2$=0.7 Hz, 1H), 8.55 (dd, $J_1$=5.0 Hz, $J_2$=1.7 Hz, 1H), 7.73-7.66 (m, 1H), 7.38 (ddd, $J_1$=7.8 Hz, $J_2$=4.9 Hz, $J_3$=0.8 Hz, 1H), 7.06 (d, J=8.1 Hz, 1H), 6.86 (d, J=2.6 Hz, 1H), 6.83 (dd, $J_1$=8.1 Hz, $J_2$=2.6 Hz, 1H), 2.21 (s, 3H); $^{13}$C NMR (75 MHz, CDCl$_3$) δ ppm: 157.1, 149.4, 146.7, 138.0, 137.5, 137.0, 131.0, 129.2, 123.4, 117.6, 113.4, 20.5; HRMS (EI) m/z: calcd for $C_{12}H_{11}NO$: 186.0919 (M+1), found: 186.0920.

Example 80: 4'-methoxy-2,3'-dimethylbiphenyl-4-ol (29b)

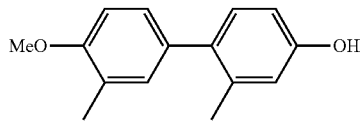 [SMILES: COc1ccc(-c2ccc(O)cc2C)cc1C]

Yield 63% (hexane/AcOEt 10:1). $^1$H NMR (300 MHz, CDCl$_3$) δ ppm: 7.11 (d, J=8.0 Hz, 3H), 6.89 (dd, $J_1$=6.9, $J_2$=2.1 Hz, 1H), 6.73 (ddd, $J_1$=8.1 Hz, $J_2$=2.7 Hz, $J_3$=0.5 Hz, 1H), 6.77 (dd, $J_1$=2.2 Hz, 0.5 Hz, 1H), 5.42 (s, 1H), 3.90 (s, 3H), 2.29 (s, 3H), 2.26 (s, 3H); 13C NMR (75 MHz, CDCl$_3$) δ ppm: 156.4, 154.3, 137.1, 134.5, 133.6, 131.7, 131.0, 127.6, 126.1, 116.8, 112.6, 109.6, 55.4, 20.6, 16.2; HRMS (EI) m/z: calcd for $C_{15}H_{16}O_2$: 227.1072 (M−1), found: 227.1068.

Example 81: 3-methyl-4-(pyridin-3-yl)phenyl trifluoromethanesulfonate (30a)

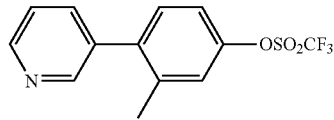

Yield 55% (CH$_2$Cl$_2$/AcOEt 5:1). $^1$H NMR (300 MHz, CDCl$_3$) δ ppm: 8.63 (dd, $J_1$=4.9 Hz, $J_2$=1.7 Hz, 1H), 8.56 (dd, $J_1$=2.3 Hz, $J_2$=0.9 Hz, 1H), 7.62 (ddd, $J_1$=7.8 Hz, $J_2$=2.3 Hz, $J_3$=1.7 Hz, 1H), 7.37 (ddd, $J_1$=7.8 Hz, $J_2$=4.9 Hz, $J_3$=0.9 Hz, 1H), 7.28 (d, J=8.3 Hz, 1H), 7.21 (d, J=2.6 Hz, 1H), 7.18 (dd, $J_1$=8.3 Hz, $J_2$=2.6 Hz, 1H), 2.29 (s, 3H); $^{19}$F NMR (282 MHz, CDCl$_3$) δ ppm: −72.9 (s, 3F); $^{13}$C NMR (75 MHz, CDCl$_3$) δ ppm: 149.6, 149.0, 148.8, 138.6, 138.5, 136.3, 135.6, 131.5, 123.1, 123.0, 118.8, 118.7 (q, $^1J$=320.7 Hz), 20.5; HRMS (EI) m/z: calcd for $C_{13}H_{10}F_3NO_3S$: 318.0412 (M+1), found: 318.0419.

Example 82: 4'-methoxy-2-methylbiphenyl-4-yl trifluoromethanesulfonate (30b)

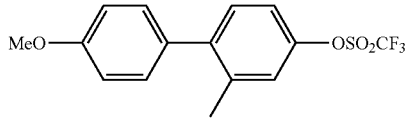

Yield 97% (hexane/AcOEt 50:1). $^1H$ NMR (300 MHz, $CDCl_3$) δ ppm: 7.27 (d, J=8.4 Hz, 1H), 7.17 (d, J=2.6 Hz, 1H), 7.15-7.05 (m, 3H), 6.89 (d, J=8.5 Hz, 1H), 3.89 (s, 3H), 2.32 (s, 3H), 2.82 (s, 3H); $^{19}F$ NMR (282 MHz, $CDCl_3$) δ ppm: −72.96 (s, 3F). −73.15 (s, 3H); $^{13}C$ NMR (75 MHz, $CDCl_3$) δ ppm: 157.2, 148.2, 142.2, 138.3, 132.0, 131.4, 131.3, 127.4, 126.5, 122.6, 118.8 (q, $^1J$=318.7 Hz), 118.3, 109.6, 55.3, 20.7, 16.2.

Example 83: ethyl 3-[4,4''-dimethoxy-3,2'-dimethyl-(1,1';4'',1''')terphenyl-2''-yl]propionate (31)

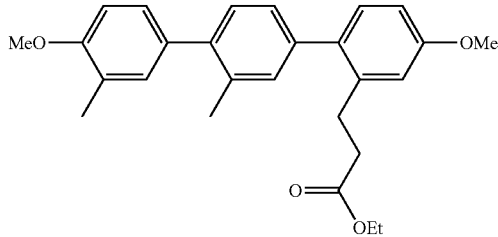 [SMILES: COc1ccc(-c2ccc(-c3ccc(OC)c(C)c3)c(C)c2)c(CCC(=O)O)c1]

Yield 25% (hexane/AcOEt 20:1). $^1H$ NMR (300 MHz, $CDCl_3$) δ ppm: 7.26-7.11 (m, 6H), 6.93-6.88 (m, 1H), 6.86 (d, J=2.5 Hz, 1H), 6.82 (dd, $J_1$=8.3 Hz, $J_2$=2.7 Hz, 1H), 4.10 (q, J=7.1 Hz, 2H), 3.89 (s, 3H), 3.85 (s, 3H), 2.99 (t, J=8.0 Hz, 2H), 2.50 (t, J=8.0 Hz, 2H), 2.33 (s, 3H), 2.29 (s, 3H), 1.22 (t, J=7.1 Hz, 3H); $^{13}C$ NMR (75 MHz, $CDCl_3$) δ ppm: 172.9, 158.8, 156.7, 140.1, 139.7, 139.4, 135.1, 134.5, 133.7, 131.6, 131.3, 131.3, 129.7, 127.5, 126.7, 126.1, 114.5, 111.5, 109.5, 60.3, 55.3, 55.3, 35.5, 28.6, 20.7, 16.3, 14.2; HRMS (EI) m/z: calcd for $C_{27}H_{30}O_4$: 441.2042 (M+Na), found: 441.2047.

Example 84: 3-[4,4''-dimethoxy-3,2'-dimethyl-(1,1'; 4',1''')terphenyl-2''-yl]propionic acid (32)

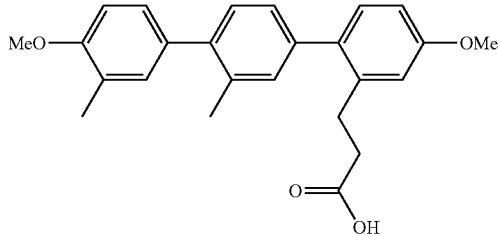

Yield 97%. $^1H$ NMR (300 MHz, $CDCl_3$) δ ppm: 7.25-7.09 (m, 6H), 6.91-6.87 (m, 1H), 6.86 (d, J=2.3 Hz, 1H), 6.83 (dd, $J_1$=8.2 Hz, $J_2$=2.7 Hz, 1H), 3.89 (s, 3H), 3.84 (s, 3H), 2.99 (t, J=8.0 Hz, 2H), 2.54 (t, J=8.0 Hz, 2H), 2.32 (s, 3H), 2.29 (s, 3H); $^{13}C$ NMR (75 MHz, $CDCl_3$) δ ppm: 178.5, 158.9, 156.7, 140.2, 139.6, 139.0, 135.2, 134.5, 133.6, 131.7, 131.4, 131.2, 129.7, 127.5, 126.6, 126.1, 114.5, 111.6, 109.5, 55.3, 55.3, 35.1, 29.7, 28.3, 20.7, 16.3; HRMS (EI) m/z: calcd for $C_{25}H_{26}O_4$: 389.1753 (M−1), found: 389.1760.

Example 85: 1-(benzyloxy)-3-isopropylbenzene (33)

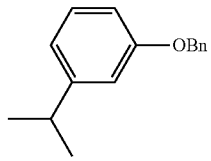 [SMILES: CC(C)c1cccc(OCc2ccccc2)c1]

To a solution of 3-isopropylphenol (953 mg, 7.00 mmol) in anhydrous DMF (20 mL) were added potassium carbonate (1.934 g, 14.00 mmol) and benzyl bromide (1.316 g, 7.70 mmol). The reaction mixture was stirred overnight at room temperature, filtered and the solvent was removed under reduced pressure. The resulting crude reaction product was suspended in water and extracted with AcOEt. The combined organic layers were dried over $Na_2SO_4$, filtered and the volatiles were removed in vacuo to give 1.583 g of 9. Yield 99%. $^1H$ NMR (300 MHz, $CDCl_3$) δ ppm: 7.32-7.51 (m, 5H), 7.25 (t, J=7.8 Hz, 1H), 6.80-6.94 (m, 3H), 5.09 (s, 2H), 2.92 (sep, J=6.9 Hz, 1H), 1.28 (d, J=6.9 Hz, 6H); $^{13}C$ NMR (75 MHz, $CDCl_3$) δ ppm: 158.9, 150.6, 137.2, 129.2, 128.5, 127.9, 127.5, 119.2, 113.4, 111.6, 69.9, 34.1, 23.9; HRMS (EI) m/z: calcd for $C_{16}H_{18}O$: 226.1358, found: 226.1350.

Example 86: 4-(benzyloxy)-1-bromo-2-isopropylbenzene (34)

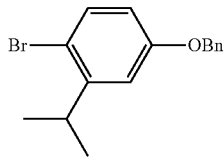

To a solution of 33 (452 mg, 2.00 mmol) in $CCl_4$ (20 mL) were added N-bromosuccinimide (373 mg, 2.10 mmol) and silica gel (1 g) and the mixture was stirred in the dark at room temperature for 36 hours. Then, the mixture was filtered and the filtrates were washed with saturated solution of sodium thiosulphate (10 mL). The organic phase were dried over $Na_2SO_4$, filtered and concentrated on vacuo to give 564 mg of bromoaryl 34. Yield 93%. $^1H$ NMR (300 MHz, $CDCl_3$) δ ppm: 7.32-7.51 (m, 6H), 6.92 (d, J=3.0 Hz, 1H), 6.68 (dd, $J_1$=8.7 Hz, $J_2$=3.0 Hz, 1H), 5.04 (s, 2H), 3.31 (sep, J=6.9 Hz, 1H), 1.22 (d, J=6.9 Hz, 6H); $^{13}C$ NMR (75 MHz, $CDCl_3$) δ ppm: 158.4, 148.5, 136.7, 133.2, 128.6, 128.1, 127.5, 115.0, 114.0, 113.3, 70.2, 33.0, 22.7; HRMS (EI) m/z: calcd for $C_{16}H_{17}BrO$: 304.0463, found: 304.0465.

Example 87: 2-[4-(benzyloxy)-2-isopropylphenyl]-4,4,5,5-tetramethyl-1,3,2-dioxaborolane (35)

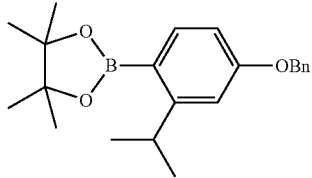 [SMILES: CC(C)c1cc(OCc2ccccc2)ccc1B1OC(C)(C)C(C)(C)O1]

Yield 45% (hexane/AcOEt 50:1). $^1$H NMR (300 MHz, CDCl$_3$) δ ppm: 7.75 (d, J=8.1 Hz, 1H), 7.33-7.48 (m, 5H), 6.96 (d, J=2.4 Hz, 1H), 6.79 (dd, J$_1$=8.4 Hz, J$_2$=2.4 Hz, 1H), 5.10 (s, 2H), 3.75 (sep, J=6.9 Hz, 1H), 1.35 (s, 12H), 1.23 (d, J=6.9 Hz, 6H); $^{13}$C NMR (75 MHz, CDCl$_3$) δ ppm: 161.2, 158.1, 137.9, 137.0, 128.5, 127.9, 127.5, 112.0, 110.5, 83.1, 69.7, 31.3, 24.8, 24.3; HRMS (EI) m/z: calcd for C$_{22}$H$_{30}$BO$_3$: 352.2324, found: 352.2281.

Example 88: ethyl (E)-3-[3'-formyl-4-(hydroxybiphenyl)-2-yl]acrylate (36)

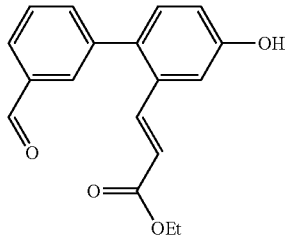 [SMILES: CCOC(=O)/C=C/c1cc(O)ccc1-c1cccc(C=O)c1]

Yield 58% (hexane/AcOEt 10:1). $^1$H NMR (300 MHz, CDCl$_3$) δ ppm: 9.99 (s, 1H), 7.82 (dt, J$_1$=7.2 Hz, J$_2$=1.6 Hz, 1H), 7.74 (t, J=1.5 Hz, 1H), 7.52-7.55 (m, 1H), 7.45-7.51 (m, 2H), 7.19 (d, J=8.3 Hz, 1H), 7.10 (d, J=2.6 Hz, 1H), 6.89 (dd, J$_1$=8.3 Hz, J$_2$=2.6 Hz, 1H), 6.30 (d, J=15.9 Hz, 1H), 5.29 (br s, 1H), 4.13 (q, J=7.1 Hz, 2H), 1.20 (t, J=7.1 Hz, 3H); $^{13}$C NMR (75 MHz, CDCl$_3$) b ppm: 192.2, 166.7, 155.6, 142.7, 140.7, 136.5, 135.9, 134.2, 133.9, 131.8, 130.9, 129.0, 128.6, 120.1, 117.5, 113.2, 60.6, 14.2; HRMS (EI) m/z: calcd for C$_{18}$H$_{16}$O$_4$: 296.1049, found: 296.1043; white solid, mp: 148-149° C.

Example 89: ethyl (E)-3-[3'-formyl-4-(trifluoromethanosulfonyloxy)biphenyl-2-yl]acrylate (37)

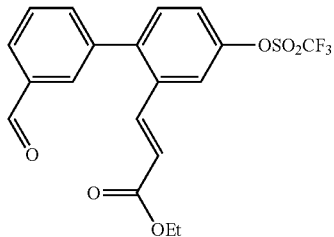

Yield 85% (hexane/AcOEt 10:1). $^1$H NMR (300 MHz, CDCl$_3$) δ ppm: 10.07 (d, 1H), 7.96 (dt, J$_1$=7.6 Hz, J$_2$=1.4 Hz, 1H), 7.83 (t, J=1.4 Hz, 1H), 7.65 (t, J=7.6 Hz, 1H), 7.59 (d, J=2.5 Hz, 1H), 7.56 (dt, J$_1$=8.1 Hz, J$_2$=1.6 Hz, 1H), 7.54 (d, J=15.9 Hz, 1H), 7.47 (d, J=8.5 Hz, 1H), 7.37 (dd, J$_1$=8.5 Hz, J$_2$=2.5 Hz, 1H), 6.43 (d, J=15.9 Hz, 1H), 4.21 (q, J=7.1 Hz, 2H), 1.28 (t, J=7.1 Hz, 3H); $^{19}$F NMR (282 MHz, CDCl$_3$) δ ppm: −73.17 (s, 3F); $^{13}$C NMR (75 MHz, CDCl$_3$) δ ppm: 191.6, 165.9, 149.2, 141.2, 140.7, 139.1, 136.7, 135.4, 135.2, 132.3, 130.4, 129.6, 129.3, 122.4, 122.2, 119.6, 118.7 (q, $^1$J=318.8 Hz), 60.8, 14.2; HRMS (EI) m/z: calcd for C$_{19}$H$_{15}$F$_3$O$_6$S: 428.0541, found: 428.0546; white solid, mp: 77-78° C.

Example 90: ethyl (E)-3-[4"-(benzyloxy)-3-formyl-2"-isopropyl-(1,1';4',1")terphenyl-2'-yl]acrylate (38)

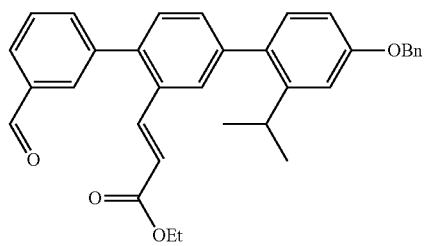 [SMILES: CCOC(=O)/C=C/c1cc(-c2ccc(OCc3ccccc3)cc2C(C)C)ccc1-c1cccc(C=O)c1]

Yield 15% (hexane/AcOEt 5:1). $^1$H NMR (300 MHz, CDCl$_3$) δ ppm: 10.09 (s, 1H), 7.88-7.96 (m, 2H), 7.61-7.72 (m, 5H), 7.33-7.55 (m, 8H), 7.15 (d, J=8.4 Hz, 1H), 7.04 (d, J=2.4 Hz, 1H), 6.88 (dd, J$_1$=8.4 Hz, J$_2$=2.4 Hz, 1H), 6.40 (d, J=15.6 Hz, 1H), 5.12 (s, 2H), 4.19 (q, J=7.1 Hz, 2H), 3.07 (sep, J=6.9 Hz, 1H), 2.26 (t, J=7.1 Hz, 2H), 1.19 (d, J=6.9 Hz, 6H); $^{13}$C NMR (75 MHz, CDCl$_3$) δ ppm: 192.0, 177.4, 166.6, 158.8, 148.0, 142.9, 142.0, 140.8, 139.5, 137.0, 136.6, 135.7, 132.4, 131.2, 130.9, 130.9, 130.1, 129.0, 128.7, 128.6, 128.0, 128.0, 127.6, 120.1, 112.7, 111.5, 70.1, 60.5, 29.5, 24.2, 14.2; HRMS (EI) m/z: calcd for C$_{34}$H$_{32}$O$_4$: 504.2301, found: 504.2318.

Example 91: ethyl 3-[4"-hydroxy-2"-isopropyl-3-methyl-(1,1';4',1")terphenyl-2'-yl]propionate (39)

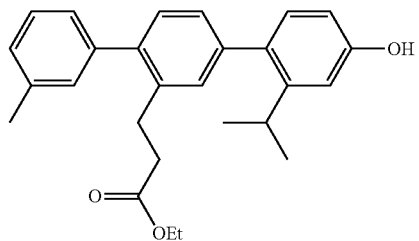 [SMILES: CCOC(=O)CCc1cc(-c2ccc(O)cc2C(C)C)ccc1-c1cccc(C)c1]

Yield 82% (hexane/AcOEt 10:1). $^1$H NMR (300 MHz, CDCl$_3$) δ ppm: 7.27-7.36 (m, 1H), 7.12-7.24 (m, 6H), 7.08 (d, J=8.4 Hz, 1H), 6.86 (d, J=2.7 Hz, 1H), 6.69 (dd, J$_1$=8.4 Hz, J$_2$=2.7 Hz, 1H), 5.06 (s, 1H), 4.06 (q, J=7.1 Hz, 2H), 3.10 (sep, J=6.9 Hz, 1H), 2.99 (t, J=8.0 Hz, 2H), 2.47 (t, J=8.0 Hz, 2H), 2.42 (s, 3H), 1.18 (t, J=7.2 Hz, 3H), 1.17 (d, J=6.9 Hz, 6H); $^{13}$C NMR (75 MHz, CDCl$_3$) δ ppm: 173.0, 155.2, 148.2, 141.3, 140.9, 140.3, 137.8, 137.4, 133.6, 131.2, 130.1, 130.0, 129.8, 128.1, 127.7, 127.4, 126.2, 112.5, 112.3, 60.3, 35.5, 29.5, 28.4, 24.2, 21.5, 14.1; HRMS (EI) m/z: calcd for C$_{27}$H$_{30}$O$_3$: 402.2195, found: 402.2197.

Biological Activity of Q₂ Peptidomimetics

Example 92

Goodpasture antigen-binding protein (GPBP) is a non-conventional Ser/Thr kinase which targets and phosphorylates the non-collagenous (NC1) domain of α3 chain of human type IV collagen [α3(IV)NC1], known as Goodpasture antigen. GPBP expression has been associated with antibody-mediated glomerulonephritis, rheumatoid arthritis and drug-resistance cancer. We have reported that GPBP self-interacts, that aggregation and autophosphorylation regulate kinase activity, and that the Q₂ peptide inhibits autophosphorylation and GPBP kinase activity (WO 00/50607). The GPBP kinase inhibitory activity of a number of terphenylic compounds mimicking Q₂, a peptide representing a critical GPBP motif which is relevant for GPBP quaternary structure stabilization, have been tested on GPBP autophosphorylation ability The autophosphorylation ability of GPBP has been used to test the GPBP kinase inhibitor activity of several terphenylic compounds (Scheme 18) derived from the chemical structure of Q₂ peptide, which in turn represents GPBP peptidic sequence relevant for self-interaction.

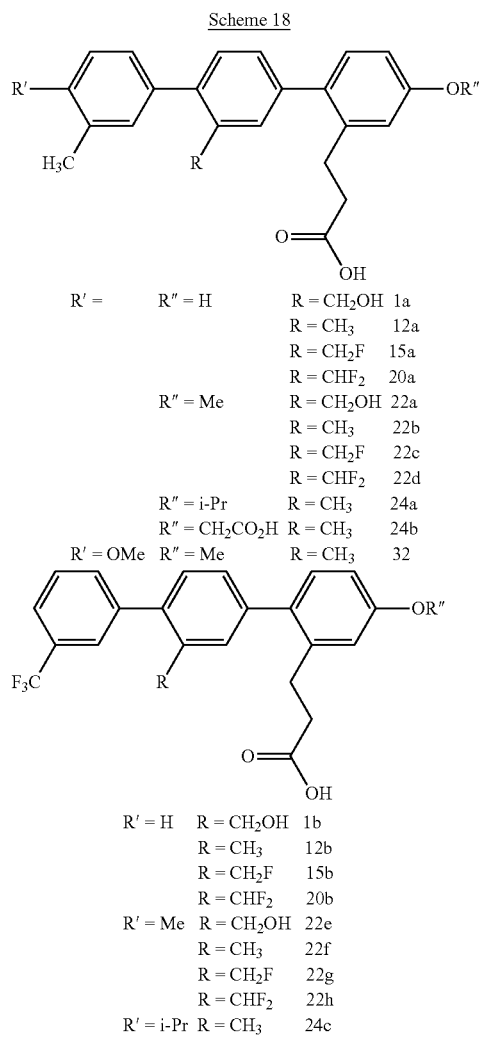

Scheme 18

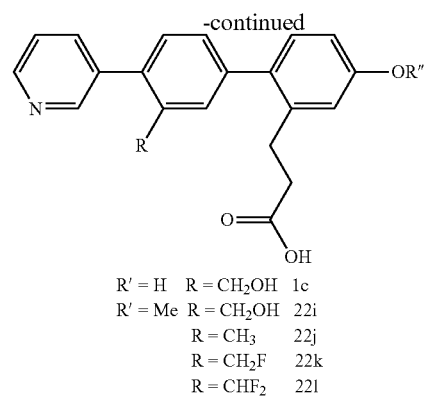

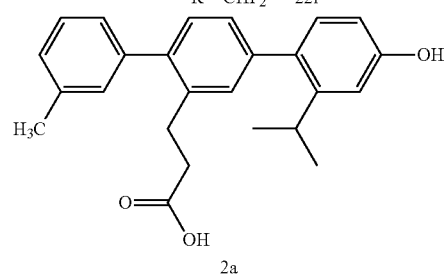

Two hundred nanograms of yeast recombinant FLAG-GPBP were subjected to phosphorylation assays in absence (vehicle) or presence of a 10 μM concentration of each of the indicated Q₂-peptidomimetic compounds or an intermediate of synthesis used as negative control (C), during 5 min at 30° C. Reactions were subjected to SDS-PAGE, Western blot and autoradiography. The bands in the autoradiography were quantified using Image-Quant TL software. The kinase activity of GPBP in the presence of the indicated compounds was referred to the sample containing the vehicle, which was given a value of 100. Table 1 shows the outcome of FLAG-GPBP auto-phosphorylation assays performed in presence or absence of the different Q₂-peptidomimetics compounds represented in Scheme 18.

TABLE 1

| Compound | Relative kinase activity (% referred to vehicle) |
|---|---|
| vehicle | 100 |
| 1a | 34 |
| 1b | 131 |
| 1c | 58 |
| 2a | 90 |
| 12a | 53 |
| 12b | 49 |
| 15a | 79 |
| 15b | 21 |
| 20a | 61 |
| 20b | 77 |
| 22a | 118 |
| 22b | 44 |
| 22c | 123 |
| 22d | 79 |
| 22e | 129 |
| 22f | 41 |
| 22g | 103 |
| 22h | 49 |
| 22i | 132 |
| 22j | 50 |
| 22k | 135 |
| 22l | 136 |
| 24a | 73 |
| 24b | 64 |

TABLE 1-continued

| Compound | Relative kinase activity (% referred to vehicle) |
|---|---|
| 24c | 36 |
| 32 | 28 |
| C | 96 |

Example 93: Additional Materials and Methods

Yeast recombinant FLAG-GPBP production and purification were also performed. GPBP autophosphorylation assay times were limited to 10 min at 30° C.

It is understood that the examples and embodiments described herein are for illustrative purposes only. Unless clearly excluded by the context, all embodiments disclosed for one aspect of the invention can be combined with embodiments disclosed for other aspects of the invention, in any suitable combination. It will be apparent to those skilled in the art that various modifications and variations can be made to the present invention without departing from the scope of the invention. Thus, it is intended that the present invention cover the modifications and variations of this invention provided they come within the scope of the appended claims and their equivalents. All publications, patents, and patent applications cited herein are hereby incorporated herein by reference for all purposes.

or a pharmaceutically acceptable salt thereof, wherein:
R is $CR_5$;
$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), ($C_1$-$C_6$ alkyl)sulfanyl($C_1$-$C_6$ alkyl), —$(CH_2)_{1-5}$—C(O)($C_1$-$C_6$ alkoxy), —$(CH_2)_{1-5}$—$C(O)NH_2$, (aryl)$C_2$-$C_6$ alkyl, and (heteroaryl)$C_1$-$C_6$ alkyl;
$R_1$ is hydrogen, halogen, hydroxy, $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), or ($C_1$-$C_6$ alkyl) sulfanyl($C_1$-$C_6$ alkyl);
$R_2$ is $C_1$-$C_6$ alkyl, $C_1$-$C_6$ alkoxy, hydroxy($C_1$-$C_6$ alkyl), ($C_1$-$C_6$ alkoxy)$C_1$-$C_6$ alkyl, or formyl($C_0$-$C_6$ alkyl);
$R_3$ is —CH=CH—C(O)OH or —CH=CH—C(O)($C_1$-$C_6$ alkoxy); and
$R_4$ is hydroxy, halogen, $C_1$-$C_6$ alkyl, $C_1$-$C_6$ alkoxy, halo($C_1$-$C_6$ alkoxy), benzyloxy, —$(CH_2)_{1-5}$—C(O)OH, —$(CH_2)_{1-5}$—C(O)($C_1$-$C_6$ alkoxy), —$(CH_2)_{1-5}$—$C(O)NH_2$, —$(CH_2)_{1-5}$—C(O)NH($C_1$-$C_6$ alkyl), —$(CH_2)_{1-5}$—C(O)N($C_1$-$C_6$ alkyl)$_2$, —CH=CH—C(O)OH, —CH=CH—C(O)($C_1$-$C_6$ alkoxy), —O($CH_2)_{1-5}$—C(O)OH, —O($CH_2)_{1-5}$—C(O)($C_1$-$C_6$ alkoxy), (aryl)$C_1$-$C_6$ alkyl, or (heteroaryl)$C_1$-$C_6$ alkyl.

What is claimed is:

1. A compound of formula:

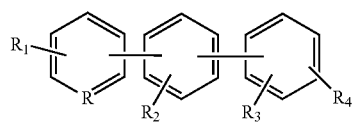

2. A compound according to claim 1 having the formula:

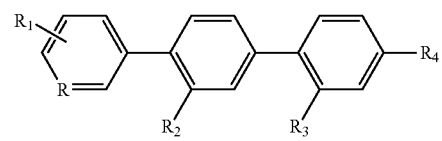

wherein:
R is $CR_5$;
  $R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), ($C_1$-$C_6$ alkyl)sulfanyl($C_1$-$C_6$ alkyl), —$(CH_2)_{1-5}$—C(O)($C_1$-$C_6$ alkoxy), and —$(CH_2)_{1-5}$—C(O)$NH_2$;
$R_1$ is hydrogen, halogen, hydroxy, $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), or ($C_1$-$C_6$ alkyl)sulfanyl($C_1$-$C_6$ alkyl);
$R_2$ is $C_1$-$C_6$ alkyl, halo($C_1$-$C_6$ alkyl), $C_1$-$C_6$ alkoxy, hydroxy($C_1$-$C_6$ alkyl), ($C_1$-$C_6$ alkoxy)$C_1$-$C_6$ alkyl, or formyl($C_0$-$C_6$ alkyl);
$R_3$ is —CH=CH—C(O)OH, or —CH=CH—C(O)($C_1$-$C_6$ alkoxy); and
$R_4$ is hydroxy, halogen, $C_1$-$C_6$ alkyl, $C_1$-$C_6$ alkoxy, halo($C_1$-$C_6$ alkoxy), benzyloxy, —$(CH_2)_{1-5}$—C(O)OH, —$(CH_2)_{1-5}$—C(O)($C_1$-$C_6$ alkoxy), —$(CH_2)_{1-5}$—C(O)$NH_2$, —$(CH_2)_{1-5}$—C(O)NH($C_1$-$C_6$ alkyl), —$(CH_2)_{1-5}$—C(O)N($C_1$-$C_6$ alkyl)$_2$, —CH=CH—C(O)OH, —CH=CH—C(O)($C_1$-$C_6$ alkoxy), —O$(CH_2)_{1-5}$—C(O)OH, or —O$(CH_2)_{1-5}$—C(O)($C_1$-$C_6$ alkoxy).

3. A compound according to claim 1, wherein
R is $CR_5$;
  $R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);
$R_1$ is hydrogen, halogen, hydroxy, $C_1$-$C_6$ alkyl, halo($C_1$-$C_6$ alkyl), $C_1$-$C_6$ alkoxy, or halo($C_1$-$C_6$ alkoxy);
$R_2$ is $C_1$-$C_6$ alkyl, hydroxy($C_1$-$C_6$ alkyl), ($C_1$-$C_6$ alkoxy)$C_1$-$C_6$ alkyl, or formyl($C_0$-$C_6$ alkyl);
$R_3$ is CH=CH—C(O)OH, or —CH=CH—C(O)($C_1$-$C_6$ alkoxy); and
$R_4$ is hydroxy, halogen, $C_1$-$C_6$ alkyl, $C_1$-$C_6$ alkoxy, halo($C_1$-$C_6$ alkoxy), benzyloxy, —$(CH_2)_{1-5}$—C(O)OH, —$(CH_2)_{1-5}$—C(O)($C_1$-$C_6$ alkoxy), —$(CH_2)_{1-5}$—C(O)$NH_2$, —$(CH_2)_{1-5}$—C(O)NH($C_1$-$C_6$ alkyl), —$(CH_2)_{1-5}$—C(O)N($C_1$-$C_6$ alkyl)$_2$, —CH=CH—C(O)OH, —CH=CH—C(O)($C_1$-$C_6$ alkoxy), —O$(CH_2)_{1-5}$—C(O)OH, or —O$(CH_2)_{1-5}$—C(O)($C_1$-$C_6$ alkoxy).

4. A compound according to claim 1, having the formula:

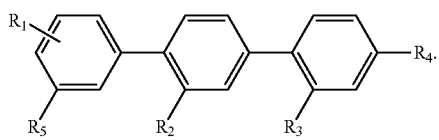

5. A compound according to claim 1, wherein
$R_1$ is hydrogen.

6. A compound according to claim 1, wherein
$R_2$ is $C_1$-$C_6$ alkyl, hydroxy($C_1$-$C_6$ alkyl), or formyl($C_0$-$C_6$ alkyl).

7. A compound according to claim 6, wherein $R_2$ is hydroxy($C_1$-$C_6$ alkyl).

8. A compound according to claim 1, wherein
$R_3$ is CH=CH—C(O)OH.

9. A compound according to claim 1, wherein
$R_4$ is hydroxy, halogen, $C_1$-$C_6$ alkyl, $C_1$-$C_6$ alkoxy, halo($C_1$-$C_6$ alkoxy), or benzyloxy.

10. A compound according to claim 9, wherein $R_4$ is hydroxy or $C_1$-$C_6$ alkoxy.

11. A compound according to claim 1, wherein
$R_5$ is $C_1$-$C_6$ alkyl, halo($C_1$-$C_6$ alkyl), $C_1$-$C_6$ alkoxy, or halo($C_1$-$C_6$ alkoxy).

12. A compound according to claim 1, wherein
$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);
$R_1$ is hydrogen, halogen, hydroxy, $C_1$-$C_6$ alkyl, halo($C_1$-$C_6$ alkyl), $C_1$-$C_6$ alkoxy, or halo($C_1$-$C_6$ alkoxy);
$R_2$ is $C_1$-$C_6$ alkyl or hydroxy($C_1$-$C_6$ alkyl);
$R_3$ is —CH=CH—C(O)OH, or —CH=CH—C(O)($C_1$-$C_6$ alkoxy); and
$R_4$ is hydroxy, $C_1$-$C_6$ alkoxy, halo($C_1$-$C_6$ alkoxy), or benzyloxy.

13. A compound according to claim 1, wherein
$R_1$ is hydrogen;
$R_2$ is $C_1$-$C_6$ alkyl, hydroxy($C_1$-$C_6$ alkyl), or formyl($C_1$-$C_6$ alkyl);
$R_3$ is —CH=CH—C(O)OH, or —CH=CH—C(O)($C_1$-$C_6$ alkoxy);
$R_4$ is hydroxy or $C_1$-$C_6$ alkoxy; and
$R_5$ is $C_1$-$C_6$ alkyl, halo($C_1$-$C_6$ alkyl), $C_1$-$C_6$ alkoxy, or halo($C_1$-$C_6$ alkoxy).

14. A compound according to claim 1, wherein
R is $CR_5$;
  $R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);
$R_1$ is hydrogen;
$R_2$ is $C_1$-$C_6$ alkyl or hydroxy($C_1$-$C_6$ alkyl);
$R_3$ is —C(O)OH CH=CH—C(O)OH; and
$R_4$ is $C_1$-$C_6$ alkoxy.

15. A compound according to claim 1, wherein
R is $CR_5$;
  $R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);
$R_1$ is hydrogen;
$R_2$ is methyl or hydroxymethyl;
$R_3$ is —CH=CH—C(O)OH; and
$R_4$ is methoxy.

16. A compound according to claim 1, which is:
ethyl (E)-3-[4"-(benzyloxy)-2'-formyl-3-methyl-(1,1';4',1")terphenyl-2"-yl]acrylate;
ethyl (E)-3-[4"-(benzyloxy)-2'-formyl-3-(trifluoromethyl)-(1,1';4',1")terphenyl-2"-yl]acrylate;
ethyl (E)-3-[4"-(benzyloxy)-2'-(difluoromethyl)-3-methyl-(1,1';4',1")terphenyl-2"-yl]acrylate;
ethyl (E)-3-[4"-(benzyloxy)-2'-(difluoromethyl)-3-(trifluoromethyl)-(1,1';4',1")terphenyl-2"-yl]acrylate;
or a pharmaceutically acceptable salt thereof.

17. A pharmaceutical composition comprising a compound according to claim 1 and at least one pharmaceutically acceptable carrier, solvent, adjuvant or diluent.

18. A compound according to claim 1, wherein
$R_1$ is hydrogen or $C_1$-$C_6$ alkoxy;
$R_2$ is hydroxy($C_1$-$C_6$ alkyl);
$R_3$ is -CH=CH—C(O)OH;
$R_4$ is $C_1$-$C_6$ alkoxy; and
$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl).

19. A compound according to claim 1, wherein
$R_1$ is hydrogen;
$R_2$ is hydroxy($C_1$-$C_6$ alkyl);
$R_3$ is —CH=CH—C(O)OH;
$R_4$ is $C_1$-$C_6$ alkoxy; and
$R_5$ is $C_1$-$C_6$ alkyl.

* * * * *